US010806778B2

(12) United States Patent
Cranenburgh et al.

(10) Patent No.: US 10,806,778 B2
(45) Date of Patent: Oct. 20, 2020

(54) **MODIFIED STRAIN OF *SALMONELLA ENTERICA* TYPHI**

(71) Applicant: PROKARIUM LIMITED, London (GB)

(72) Inventors: Rocky Marc Cranenburgh, London (GB); Annelise Juliette Soulier, London (GB)

(73) Assignee: PROKARIUM LIMITED, London (GB)

( * ) Notice: Subject to any disclaimer, the term of this patent is extended or adjusted under 35 U.S.C. 154(b) by 0 days.

(21) Appl. No.: 16/776,429

(22) Filed: Jan. 29, 2020

(65) Prior Publication Data

US 2020/0237887 A1 Jul. 30, 2020

(30) Foreign Application Priority Data

Jan. 30, 2019 (EP) .................................... 19154550

(51) Int. Cl.

| | |
|---|---|
| *A61K 39/02* | (2006.01) |
| *C12N 1/20* | (2006.01) |
| *C12N 1/36* | (2006.01) |
| *A61K 39/112* | (2006.01) |
| *A61K 39/00* | (2006.01) |

(52) U.S. Cl.
CPC ............ *A61K 39/0275* (2013.01); *C12N 1/20* (2013.01); *C12N 1/36* (2013.01); *A61K 2039/522* (2013.01); *C12N 2510/00* (2013.01)

(58) Field of Classification Search
None
See application file for complete search history.

(56) References Cited

U.S. PATENT DOCUMENTS 6,130,082 A 10/2000 Majarian et al.

FOREIGN PATENT DOCUMENTS

| | | |
|---|---|---|
| WO | 97/14782 | 4/1997 |
| WO | 98/26799 A1 | 6/1998 |
| WO | 2005/052167 A2 | 6/2005 |
| WO | 2007/053489 A2 | 5/2007 |
| WO | 2012/001352 A1 | 1/2012 |

OTHER PUBLICATIONS

Pfitzner, Gabriele, Invitation to Pay Fees and Partial International Search Report, European Patent Office, PCT/EP2020/052298, dated May 19, 2020.
Degryse, Eric, "Development of stable, genetically well-defined conditionally viable *Escherichia coli* strains," Mol. Gen. Genet., vol. 227, pp. 49-51, 1991.
Fangtham et al., "Emergence of *Slmonella* paratyphi A as a Major Cause fo Enteric Fever: Need for Early Detection, Preventive Measures, and Effective Vaccines," J. of Travel Med., vol. 15, Issue 5, pp. 344-350, 2008.
Love et al., "Stable high-copy-number bacteriophage [lambda] promoter vectors for overproduction of proteins in *Escherichia coli*," Gene, vol. 176, pp. 49-53, 1996.
Martin, Laura B., "Vaccines for typhoid fever and other salmonelloses," Curr. Opin. Infect. Dis., vol. 25, No. 5, pp. 489-499, 2012.
McClelland et al., "Comparison of genome degradation in Paratyphi A and Typhi, human-restricted serovars of *Salmonella enterica* that cause typhoid," Nature Genetics, vol. 36, No. 12, pp. 1268-1274, 2004.
Roland et al., "Reactogenicity and immunogenicity of live attenuated *Salmonella enterica* serovar Paratyphi A enteric fever vaccine candidates," Vaccine, vol. 28, pp. 3679-3687, 2010.
Baker et al., "A Novel Linear Plasmid Mediates Flagellar Variation in *Salmonella* Typhi," PLoS Pathog, 3(5):e59, 2007.
Bloor et al., "An Efficient Method of Selectable Marker Gene Excision by Xer Recombination for Gene Replacement in Bacterial Chromosomes," Applied Environ. Microbiol., 72(4): 2520-2525, 2006.
Bonifield et al., "Flagellar Phase Variation in *Salmonella enterica* Is Mediated by a Posttranscriptional Control Mechanism," J. of Bact., 185(12): 3567-3574, 2003.
Dharmasena et al., "Stabel Chromosomal Expression of Shigella Flexneri 2a and 3a O-Antigens in the Live *Salmonella* Oral Vaccine Vector Ty21a," Clin. Vaccine Immunol., 24(12):300181-17, 2017.
Dunstan et al, "Use of In Vivo-Regulated Promoters To Deliver Antigens from Attenuated *Salmonella enterica* var. *typhimurium*," Infect. Immun., 67(10):5133-5141, 1999.
Edwards et al., "Protection of live bacteria from bile acid toxicity using bile acid adsorbing resins," Vaccine, 27:3897-3903, 2009.
Frankel et al., "Intragenic recombination in a flagellin gene: Characterization of the H1-j gene of *Salmonella* typhi," EMBO J., 8(10):3149-3152, 1989.
Garmory et al., "Antibiotic-Free Plasmid Stabilization by Operator-Repressor Titration for Vaccine Delivery by Using Live *Salmonella enterica* Serovar Typhimurium," Infection and Immunity, 73(4):2005-2011, 2005.
Grimont & Weill, "Antigenic formulae of the *Salmonella* serovars," 9th Edition, 2007.
Haiko et al., "The Role of the Bacterial Flagellum in Adhesion and Virulence," Biology, 2:1242-1267, 2013.
Janis et al., "In Vivo Regulation of the Vi Antigen in *Salmonella* and Induction of Immune Responses with an In Vivo-Inducible Promoter," Infection & Immunity, 79(6):2481-2488, 2011.
Kroger et al., "An Infection-Relevant Transcriptomic Compendium for *Salmonella enterica* Serovar Typhimurium," Cell Host & Microbe, 14:683-695, 2013.

(Continued)

*Primary Examiner* — Padmavathi Baskar
(74) *Attorney, Agent, or Firm* — Gavrilovich, Dodd & Lindsey LLP

(57) ABSTRACT

The present invention relates to the modification of a live attenuated strain of *Salmonella enterica* serovar *Typhi*, wherein its natural surface-exposed polysaccharide and flagellin antigens may be converted to, or augmented by, those from other strains of *Salmonella*, including *S. enterica* serovars *Paratyphi, Typhimurium* and *Enteritidis*. The present invention also relates to modified strains of *Salmonella enterica* serovar *Typhi* being suitable for use as components of a vaccine for enteric fever and *salmonellosis*.

9 Claims, 13 Drawing Sheets

Specification includes a Sequence Listing.

(56) References Cited

OTHER PUBLICATIONS

Levine et al., "Ty21a Live Oral Typhoid Vaccine and Prevention of Paratyphoid Fever Caused by *Salmonella enterica* Serovar Partyphi B," Clinical Infections Disease, 45(Suppl. 1): S24-8, 2007.
Martin et al., "Status of paratyphoid fever vaccine research and development," 34:2900-2902, 2016.
Paterson et al., "Recent advances in the field of *Salmonella* Typhi vaccines," Human Vaccines, 6(5):379-384, 2010.
Schreiber et al., "The Hd, Hj, and Hz66 flagella variants of *Salmonella enterica* serovar Typhi modify host responses and cellular interactions," Scientific Reports, 5:7947, Jan. 22, 2015.
Tennant et al., "Live attenuated vaccines for invasive *Salmonella* infection," Vaccine, 33(03):C36-C41, 2015.
Terpe, Kay, "Overview of bacterial expression systems for heterologous protein production: from molecular and biochemical fundamentals to commercial systems," Appl. Microbiol. Biotechnol., 72:211-222, 2006.
Wahid et al., "Live Oral Typhoid Vaccine Ty21a Induces Cross-Reactive Humoral Immune Responses against *Salmonella enterica* Serovar Partyphi A and *S.* Paratyphi B in Humans," Clinical and Vaccine Immunol., 19(6), 825-834, 2012.
Xu et al., "Efficacy of Intracellular Activated Promoters for Generation of *Salmonella*-Based Vaccines," Infect. and Immun., 78(11):4828-4838, 2010.

Figure 12A-B

MODIFIED STRAIN OF *SALMONELLA ENTERICA* TYPHI

CROSS REFERENCE TO RELATED APPLICATIONS

This application claims priority to European Application No. 19154550.8, filed Jan. 30, 2019, the disclosure of which is incorporated herein by reference in its entirety.

FIELD OF INVENTION

The present invention relates to the modification of an attenuated strain of *Salmonella enterica* serovar *Typhi*, such that its natural surface-exposed polysaccharide and flagellin antigens are converted to, or augmented by, those from other strains of *Salmonella*, including *S. enterica* serovars *Paratyphi*, *Typhimurium* and *Enteritidis*. Such a modification utilises the long history of safe use of strains of *S. Typhi* in humans as a typhoid vaccine, to deliver homologous antigens from other members of the genus *Salmonella* as components of vaccines for enteric fever and *Salmonellosis*.

INCORPORATION BY REFERENCE OF SEQUENCE LISTING

Accompanying this filing is a Sequence Listing entitled "Sequence-Listing_ST25.txt", created on Feb. 25, 2020 and having 72,899 bytes of data, machine formatted on IBM-PC, MS-Windows operating system. The sequence listing is hereby incorporated herein by reference in its entirety for all purposes.

BACKGROUND

Enteric fever is exclusive to humans and is caused by two serovars of *Salmonella enterica*: *Typhi* and *Paratyphi*, the latter comprising serovars A, B and C. Typhoid fever is estimated to have caused 21.7 million illnesses leading to 217,000 deaths in 2000, with 5.4 million cases of paratyphoid fever annually (Crump et al. 2004, Bull. World Health Organ. 82: 346-353). Typhoid and paratyphoid fevers are very similar infections of the reticuloendothelial system, intestinal lymphoid tissue and gallbladder, leading to acute febrile illnesses. Blood culture or serological tests are required to differentiate them. Outbreaks of typhoid fever are frequent in sub-Saharan Africa and Asia, with *S. Paratyphi* A responsible for up to 50% of enteric fever cases in Asia; enteric fever is also endemic in Latin America (Crump & Mintz 2010, Clin. Infectious Dis. 50: 241-246). *S. Paratyphi* A is the most abundant strain causing paratyphoid fever globally, with several reports showing it causing an increasing number of the total enteric fever cases (Fangtham & Wilde 2008, Int. J. Travel Med. 15: 344-350).

All licensed injected typhoid vaccines use the Vi capsular polysaccharide antigen purified from *S. Typhi*, and are single-dose with boosting recommended every 2-3 years (Martin 2012, Curr. Opin. Infect. Dis. 25: 489-499). The main adverse event is pain at the injection site. The only live attenuated typhoid vaccine is *S. Typhi* Ty21a (Vivotif®), developed by chemical mutagenesis of *S. Typhi* Ty2 and administered orally in 3-4 doses, with boosting required after 5-7 years (Martin 2012, Curr. Opin. Infect. Dis. 25: 489-499). Ty21a is very safe and well tolerated. In a comparative clinical study of injected vaccine Typherix® versus Vivotif®, only the latter was found to generate immune responses that mimic the natural infection (Kantele et al. 2013, Plos One 8: e60583).

The Vi antigen is not present in *S. Paratyphi* A or B (but is expressed by *S. Paratyphi* C), so injected Vi vaccines are ineffective against the two most prevalent *S. Paratyphi* strains. Ty21a has been proven to confer cross-protection against *S. Paratyphi* B in field studies (Levine et al. 2007, Clin. Infectious Dis. 45: S24-S28). However, field studies using Ty21a showed little or no cross-protection against *S. Paratyphi* A, despite the generation of cross-reactive antibody responses (Wahid et al. 2012, Clin. & Vaccine Immunol. 19: 825-834).

To try to address the short duration of protection and lack of memory response of Vi vaccines, Vi polysaccharide has been conjugated to carrier proteins in a new generation of Vi glycoconjugate vaccines. Carrier proteins include *Pseudomonas aeruginosa* exotoxin, tetanus and diphtheria toxoids (Martin 2012, Curr. Opin. Infect. Dis. 25: 489-499). Injectable conjugates of O-antigens purified from *S. Paratyphi* A have also been developed, primarily O2 conjugated to tetanus toxoid (O2-TT), to diphtheria toxoid (O2-DT) and to a detoxified mutant of the diphtheria toxin (O2-CRM$_{197}$), co-administered with Vi conjugated to the same carrier protein as enteric fever vaccines targeting *S. Typhi* and *S. Paratyphi* A (Martin et al. 2016, Vaccine 34: 2900-2902).

The live attenuated approach to enteric fever vaccine development has significant advantages over injectable Vi vaccines: longer duration of protection, generation of immunological memory, closer immunological profile to the natural infection and elimination of needles. In addition to the licensed chemically mutagenised typhoid vaccine strain Ty21a, other specifically mutated live vaccine strains of *S. Typhi* have been evaluated in clinical trials: CVD 906 and CVD 908 (ΔaroC, ΔaroD); CVD 906-htrA and CVD 908-htrA (ΔaroC, ΔaroD, ΔhtrA); CVD 909 (ΔaroC, ΔaroD, ΔhtrA and constitutive expression of Vi); M01ZH09 (ΔaroC, ΔssaV); Ty800 (ΔphoP, ΔphoQ); χ3927 (Δcya, Δcrp) (Tennant & Levine 2015, Vaccine 33: C36-C41) and χ4073 (Δcya, Δcrp, Δcdt) (Paterson & Maskell 2010, Hum. Vaccines 6: 379-384). It is reasonable to expect a degree of cross-protection from these specifically mutated *S. Typhi* strains to *S. Paratyphi* B as is the case for Ty21a.

Attenuated strains of *S. Paratyphi* A have also been produced, including ΔphoPQ mutants tested pre-clinically (Roland et al. 2010, Vaccine 28: 3679-3687), and CVD 1902 (ΔguaBA, ΔclpX) which has been evaluated in a clinical trial (Tennant & Levine 2015, Vaccine 33: C36-C41). A combination of CVD 909 and CVD 1902 is in clinical development as a vaccine targeting *S. Typhi* and *S. Paratyphi* A (Martin et al. 2016, Vaccine 34: 2900-2902). However, this strategy requires the clinical evaluation of *S. Paratyphi* A, which does not have the long history of safe use of *S. Typhi*.

Non-typhoidal *Salmonella* (NTS) cause gastroenteritis, with symptoms including diarrhoea and fever. The increase in cases of an invasive form of non-typhoidal *Salmonella* (iNTS), predominantly in Africa, is an important public health issue. The strains responsible for the vast majority of iNTS cases are *S. enterica* serovars *Typhimurium* and *Enteritidis*, and multidrug resistant isolates are of particular concern (MacLennan & Levine 2013, Expert Rev. Anti Infect. Ther. 11:443-446). iNTS strains cause a significantly more severe form of the disease, with prolonged symptoms and shedding of bacteria lasting for several weeks. There are currently no vaccines for NTS approved for human use.

The benefits of live attenuated vaccines include the induction of mucosal and cell-mediated immune responses, in addition to systemic antibody responses, and the duration of these responses can be longer than those from injected subunit vaccines as descried above for typhoid. Attenuated S. Typhi strains have been administered to millions of people as experimental and licensed vaccines with an excellent record of safety and immunogenicity. This serovar also lacks the ability to persist in environmental reservoirs due to its exclusivity to humans, thus increasing its biosafety. Therefore, there are several reasons why it is advantageous to use live attenuated S. Typhi as a vector for delivery of homologous antigens from other serovars of S. enterica, rather than attenuating the wild-type strains where the effect of the attenuating mutations may not be predictable. For example, the S. Typhi vaccine candidate ZH9 carrying mutations in the genes aroC and ssaV has been shown to be safe and well tolerated in multiple clinical trials (Lyon et al. 2010, Vaccine 28: 3602-3608), whereas the same mutations introduced into S. Typhimurium resulted in prolonged shedding in stools (Hindle et al. 2002, Infect. Immun. 70: 3457-3467).

The three most important surface antigens of the S. enterica serovars for the induction of protective immunity are lipopolysaccharide O-antigens, flagella (H-antigens) and Vi. The table below summarises the antigenic compositions of the principle enteric fever and iNTS strains following the Kauffmann-White-Le Minor scheme classification scheme (Grimont & Weill 2007, Antigenic formulae of the Salmonella serovars, 9th Edition).

| S. enterica serovar | O-antigens | Vi | Flagella (H-antigens) | |
|---|---|---|---|---|
| | | | Phase 1 | Phase 2 |
| Typhi | 9, 12 | Vi | d | — |
| Paratyphi A | 1, 2, 12 | — | a | — |
| Paratyphi B | 1, 4, [5], 12 | — | b | 1, 2 |
| Paratyphi C | 6, 7 | Vi | c | 1, 5 |
| Typhimurium | 1, 4, [5], 12 | — | i | 1, 2 |
| Enteritidis | 1, 9, 12 | — | g, m | — |

[ ] indicates antigens exceptionally found in wild-type strains.

[ ] indicates antigens exceptionally found in wild-type strains.

Salmonella lipopolysaccharides consists of lipid A linked to the KDO (3-deoxy-D-manno-octulosonic acid) terminus of a conserved core region, which is then linked to a variable, repeated O-antigen trisaccharide. In S. Typhi, S. Paratyphi A, S. Paratyphi B, S. Typhimurium and S. Enteritidis this repeated O-antigen is O12, a triglyceride of mannose (Man), rhamnose (Rha) and galactose (Gal). In S. Paratyphi A, a branch of paratose (Par; 3,6-dideoxy-D-ribo-hexose) from the C-3 of Man confers serogroup specificity: O2 (FIG. 1). In S. Paratyphi B and S. Typhimurium the C-3 Man has a diglyceride of abequose (Abe; 3,6-dideoxy-D-xylo-hexose) conferring the specificity O4. S. Typhi and S. Enteritidis have tyvelose (Tyv; 3,6-dideoxy-D-arabino-hexose) on the C-3 Man, conferring the specificity O9. FIG. 2 shows the biosynthetic pathway resulting in either Abe, Par or Tyv and representing the O-antigen differences between the serovars. S. Typhi and S. Paratyphi C additionally express the Vi capsular polysaccharide antigen.

Except for the flagella produced by S. Typhi Ty21a, flagellin is not a component of any current licensed vaccine for an S. enterica infection. Flagellin is an important pathogen-associated molecular pattern (PAMP) that is recognised by toll-like receptor 5 (TLR5) and is highly immunogenic, making it an important component of a live vaccine for S. enterica. The flagella filament of S. enterica is composed of approximately 20,000 flagellin (FliC or FljB) proteins with a terminal cap encoded by fliD (Haiko & Westerlund-VVikstrOm 2013, Biology 2: 1242-1267). S. Typhi and S. Paratyphi A are generally monotypic for flagellin, expressing only FliC.

There is a particular need in the art for improved vaccines directed toward S. enterica serovars Paratyphi A, B, C, Typhimurium and Enteritidis.

SUMMARY OF INVENTION

In a first aspect, the present invention provides a live attenuated strain of Salmonella enterica serovar Typhi wherein said strain is modified to express the lipopolysaccharide O2 O-antigens and the flagella proteins of Salmonella enterica serovar Paratyphi A.

In a second aspect, the present invention provides a live attenuated strain of Salmonella enterica serovar Typhi wherein said strain is modified to express the lipopolysaccharide O4 O-antigens and the flagella proteins of Salmonella enterica serovar Paratyphi B and Salmonella enterica serovar Typhimurium.

In a third aspect, the present invention provides a live attenuated strain of Salmonella enterica serovar Typhi wherein said strain is further modified to contain a functional fepE gene, such that long O-antigen chains are generated, preferably wherein the O-antigen chains are 100 repeated units of the trisaccharide backbone in length.

In a fourth aspect, the present invention provides a live attenuated strain of Salmonella enterica serovar Typhi wherein said strain is modified to either constitutively express the gtrC gene (encoding rhamnose acetyltransferase), or alternatively, wherein said strain is modified to express the gtrC gene in trans.

In a fifth aspect, the present invention provides a live attenuated strain of Salmonella enterica serovar Typhi wherein said strain has its native fliC gene (SEQ ID NO: 1) substituted with the fliC gene of Salmonella enterica serovar Paratyphi A (SEQ ID NO: 2), Salmonella enterica serovar Paratyphi B (SEQ ID NO: 3), Salmonella enterica serovar Paratyphi C (SEQ ID NO: 5), Salmonella enterica serovar Typhimurium (SEQ ID NO: 7) and Salmonella enterica serovar Enteritidis (SEQ ID NO: 9), such that the conferred serotype is altered from an Hd serotype to a Ha, Hb, Hc, Hi and Hg,m serotype respectively.

In a sixth aspect, the present invention provides a live attenuated strain of Salmonella enterica serovar Typhi wherein the fljBA locus, controlling expression of the fljB gene of Salmonella enterica serovar Paratyphi B (SEQ ID NO: 4), Salmonella enterica serovar Paratyphi C (SEQ ID NO: 6) and Salmonella enterica serovar Typhimurium (SEQ ID NO: 8) are inserted into the chromosome of Salmonella enterica serovar Typhi or expressed in trans.

In a seventh aspect, the present invention provides a live attenuated strain of Salmonella enterica serovar Typhi wherein said strain expresses the atypical variants of flagellin of Salmonella enterica serovar Paratyphi A, Salmonella enterica serovar Paratyphi B, Salmonella enterica serovar Paratyphi C, Salmonella enterica serovar Typhimurium and Salmonella enterica serovar Enteritidis.

In an eighth aspect, the present invention provides a live attenuated strain of Salmonella enterica serovar Typhi wherein said strain has inserted a second copy of the tviA gene (SEQ ID NO: 10).

The present invention further includes a vaccine comprising one or more said modified strains for use in enhancing immunogenicity against *Salmonella enterica* serovar *Paratyphi* A, *Paratyphi* B, *Paratyphi* C, *Typhimurium* and *Enteritidis*.

Figure 1:
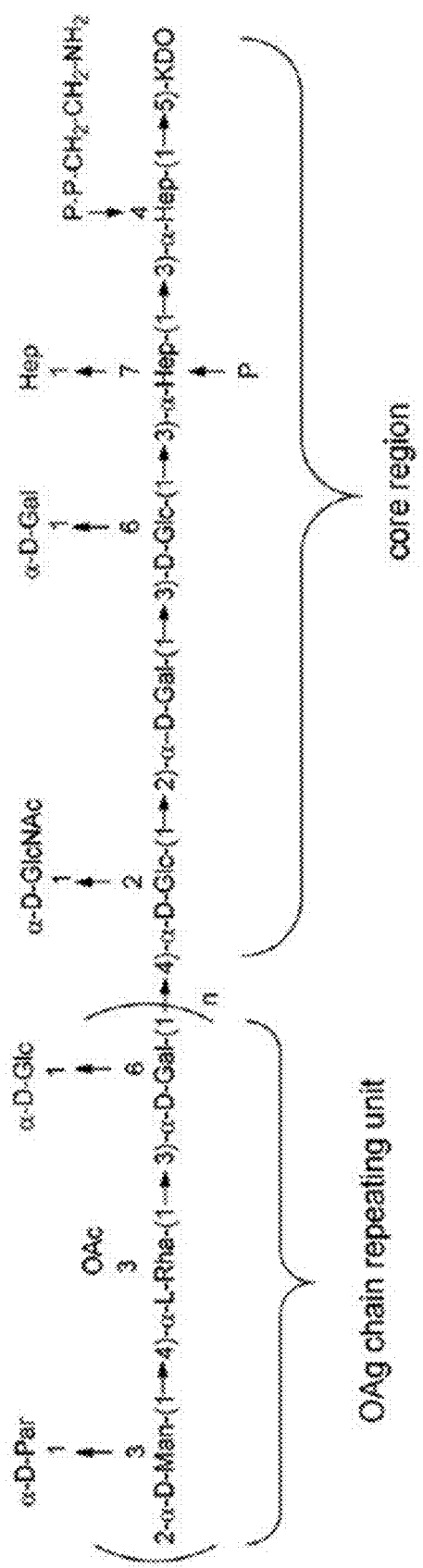
FIG. 1 illustrates the structure of the *S. Paratyphi* O-antigen chain linked to the core region (Micoli et al. 2012, Plos One 7: e47039). Par (α-D-Par) is replaced by Tyv in *S. Typhi* and *S. Enteritidis*, and by Abe in *S. Paratyphi* B and *S. Typhimurium*.

The term 'spacer region of DNA' in the context of the present invention refers to a region of non-coding DNA located between genes. The term 'cistron' refers to a section of DNA which encodes for a specific polypeptide in protein synthesis. The insertion of a spacer region of DNA may involve the transformation of an electrocompetent plasmid with a replacement cassette. See Example 1 for further details.

Where the methods herein described involve the use of a plasmid, said plasmid will ideally have an origin of replication selected from pMB1, ColEl, p15A, pSC101 and RK2. The plasmid may contain an antibiotic resistance gene selected from β-lactamase (bla), kanamycin phosphotransferase (kan), tetracycline efflux protein (tetA) or chloramphenicol acetyltransferase (cat). Ideally the antibiotic resistance gene will be excised prior to or shortly after transformation into the live bacterial vector strain, for example by a mechanism such as 'X-mark' (Cranenburgh & Leckenby 2012, WO2012/001352). A plasmid maintenance system may be required to prevent plasmid loss. These may include mechanisms to place a native chromosomal gene under a heterologous promoter such as the 'Operator-Repressor Titration for Vaccines' (ORT-VAC; Garmory et al. 2005, Infect. Immun. 73: 2005-2011) or 'oriSELECT' (Cranenburgh 2005, WO 2005/052167) systems, neither of which require an additional selectable marker gene to be present on the plasmid. Alternatively, a selectable marker gene will be used that is not an antibiotic resistance gene, such as a gene to complement a host cell mutation (Degryse 1991, Mol. Gen. Genet. 227: 49-51).

Preferably, the spacer region of DNA is the cistron of the *Escherichia coli* gene wbdR. Other non-functional genes of *Salmonella enterica* serovar *Typhi* of approximately the same length as the rfbE cistron may also be used for this purpose. It is preferable that the chosen spacer DNA used for this purpose will be approximately 50-2000 base pairs in length as well as lacking a terminator sequence. The use of this spacer region results in the inactivation of rfbE without causing any downstream effects (SEQ ID NO: 20) and effectively changing *Salmonella enterica* serovar *Typhi* LPS to *Salmonella enterica* serovar *Paratyphi* A.

The inventors have shown that deletion of rfbE whilst maintaining the original reading frame (via the use of a spacer region of DNA) is a crucial requirement of the above process.

Preferably, the resulting lipopolysaccharide O2 O-antigens of *Salmonella enterica* serovar *Paratyphi* A are at least equivalent in length to the lipopolysaccharide O9 O-antigens of *Salmonella enterica* serovar *Typhi*. It is preferable that the resulting lipopolysaccharide will be 16-35 O-antigen repeat units in length, a range which constitutes a 'long' lipopolysaccharide species. A person skilled in the art will understand the desirability of the presence of O-antigen repeat units in triggering an immunogenic reaction.

It is envisaged that the present invention may also include the live attenuated strain, according to above, wherein said strain may have its native fliC gene replaced with the fliC gene of *Salmonella enterica* serovar *Paratyphi* A, such that the conferred serotype is altered from an Hd serotype to a Ha serotype, where 'serotype' refers to a distinct variation within the bacterial species.

The Phase 1 flagellum of *S. Typhi* is essential for motility and invasion, and confers the serotype Hd. The filament consists of the flagellum protein FliC, with a FliD cap. The inventors have discovered that replacing the fliC on the *S. Typhi* chromosome with that of *S. Paratyphi* A results in the conversion from the Hd to the Ha serotype of functional flagella.

Chromosomal replacement may be used to achieve the above substitution. The substitution may be a full or partial replacement. In the context of a partial replacement, it is preferable that the replacement of the amino acids in positions 176-414 is carried out. The latter may involve the transformation of an electrocompetent plasmid with a replacement cassette. See Example 2 for further details. Alternatively, the substituted fliC gene may be expressed in trans from a plasmid or additional chromosomal location.

An additional embodiment of the present invention is the live attenuated strain described above wherein the strain may be further modified to contain a functional fepE gene, such that long O-antigen chains are generated, preferably wherein the O-antigen chains are 100 repeated units of the trisaccharide backbone in length.

The fepE gene encodes the length regulator of very long O-antigen chains, wherein 'very long' is taken to mean more than 100 repeated units of the trisaccharide backbone. *S. Typhi* does not possess these long O-antigen chains due to a mutation introducing a stop codon into the gene (SEQ ID NO: 21). *S. Typhi* may be manipulated into expressing these long O-antigen chains via a number of methods; the natural promoter of fepE may be replaced with an alternative promoter, for example P araBAD, the chromosomal mutation of fepE in *S. Typhi* may be repaired or a functional copy of fepE (SEQ ID NO: 11) may be inserted elsewhere in the *S. Typhi* chromosome. For vaccine applications, an in vivo-induced promoter or a constitutive promoter may be utilised, examples of such promoters include $P_{pagC}$, $P_{nirB}$, $P_{ssaG}$, $P_{sifA}$, $P_{sifB}$, $P_{sseA}$, $P_{sseG}$, $P_{ssej}$, $P_{lac}$, $P_{tac}$, $P_{trc}$ and lambda $P_L/P_R$.

A 'promoter' refers to a DNA regulatory region capable of binding RNA polymerase and initiating transcription of a downstream (3' direction) coding or non-coding sequence. A promoter may also be a regulatory DNA sequence that affects the binding of RNA polymerase at the transcription initiation site. For the purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence may be found a transcription initiation site, as well as protein binding domains responsible for the binding of RNA polymerase.

Promoters can be constitutively active (wherein 'active' means transcription is 'on'), spatially restricted or inducible. As used herein 'spatially restricted' refers to a promoter that is only active in a specific subset of cells or cellular compartment of a multicellular organism. A spatially restricted promoter can thus be used to activate the expression of a nucleic acid in a particular tissue or cell type of a multicellular organism.

As used herein an 'inducible promoter' refers to a promoter that enables the temporal and/or spatial activation of transcription in response to external physical or environmental stimuli. Inducible promoters include those activated by the presence of specific small molecules that alleviate transcriptional repression. For example, transcription from such an inducible promoter may be regulated by a 'repressor protein'. As used herein, 'repressor protein' refers to a polypeptide that binds to and occupies the inducible promoter to prevent transcription initiation. When bound to the promoter, said repressor protein can prevent binding or recruitment of RNA polymerase or associated co-factors to the transcription initiation site to prevent the activation of transcription. However, upon binding its relevant small molecule, or encountering its relevant physical or environmental stimulus, the repressor protein can no longer bind to the promoter sequence, and thus transcriptional repression is relieved. Where the above examples include in vivo-induced promoters for expression of cistrons encoding enzymes involved in O-antigen biosynthesis, or for expression of alternative fliC cistrons or TviA, such promoters include but are not limited to: $P_{pagC}$, $P_{nirB}$ $P_{ssaG}$, $P_{sifA}$ $P_{sifB}$, $P_{sseA}$, $P_{sseG}$ and $P_{sseJ}$ (Dunstan et al. 1999, Infect. Immun. 67: 5133-5141; Xu et al. 2010, Infect. Immun. 78: 4828-4838; Kroger et al. 2013, Cell Host & Microbe 14: 683-695). Other promoters of use include lambda a and $P_R$ the temperature-induced lambda repressor cI including its thermo-labile mutant repressor cI857 (Love et al. 1996, Gene 176:49-53; SEQ ID NO: 24 & 25) and promoters that are constitutive in *Salmonella* in the absence of the LacI repressor such as $P_{lac}$, $P_{tac}$ and $P_{trc}$ (Terpe 2006, Appl. Microbiol. Biotechnol. 72: 211-222). In some embodiments, the functional variants include those having similar or modified sequences to $P_{pagC}$, $P_{nirB}$, $P_{ssaG}$, $P_{sifA}$, $P_{sifB}$, $P_{sseA}$, $P_{sseG}$ $P_{ssej}$ and lambda $P_L/P_R$, and similar or substantially identical promoter activity as the wild-type promoter from which the variant is derived, particularly with respect to its ability to induce expression in vivo. Similar modified sequences may include having at least about 70%, 80%, 85%, 90%, 95%, 96%, 97%, 98% or 99% identity to the wild-type sequence of any of $P_{pagC}$, $P_{nirB}$, $P_{ssaG}$, $P_{sifA}$, $P_{sifB}$, $P_{sseA}$, $P_{sseG}$, $P_{sseJ}$ and lambda $P_L/P_R$.

Preferably, the introduction of these long O-antigen chains may be beneficial in inducing an LPS-specific immune response. There may be an additional benefit where the LPS is naturally very long such as from expression of fepE.

It is further envisaged that the live attenuated strain described above may be modified to constitutively express gtrC or to express gtrC in trans.

Particular *S. enterica* serovars are acetylated on the rhamnose on the O-antigen, a feature which has been demonstrated as important for O2 O-antigen specificity in *S. Paratyphi* A. The family 2 gtr operon (SEQ ID NO: 22) encodes the rhamnose acetyltransferase GtrC in *S. Typhi* and *S. Paratyphi* A. To achieve a greater and more consistent level of rhamnose acetylation it may be desirable to make gtrC constitutively expressed, for example, either on a plasmid or from an additional chromosomal locus. Alternatively, the native family 2 gtr operon promoter responsible for phase variation can be replaced with a constitutive promoter or one that is conditionally expressed in vivo.

It is further envisaged that the live attenuated strain described above may be further modified to contain an additional copy of the tviA gene under the control of a phagosomally induced promoter.

The Vi capsular polysaccharide antigen contributes to the virulence of *S. Typhi* but is naturally down-regulated upon invasion of the liver and spleen (Janis et al. 2011, Infect. Immun. 79: 2481-2488). Regulation of Vi expression is carried out by the positive transcriptional regulator TviA.

Figure 11:
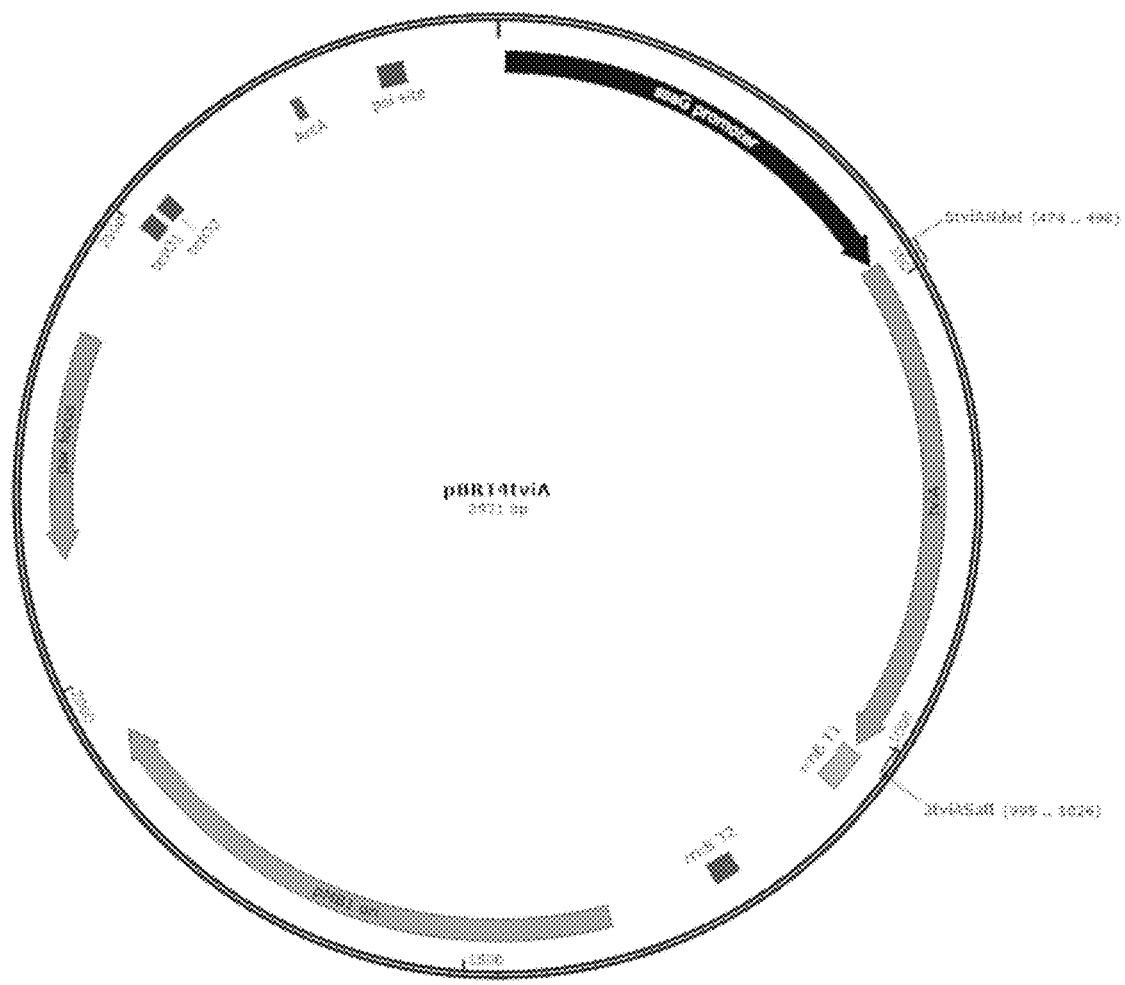

The insertion of a second copy of the tviA gene into *S. Typhi* may induce immune responses against Vi and enhance the anti-flagellin response. The second copy may be inserted into the *S. Typhi* in trans, either on a plasmid (FIG. 11) or integrated into the *S. Typhi* chromosome, such that it is under the control of a phagosomally induced promoter. Examples of appropriate phagosomally induced promoters include; $P_{pagC}$, $P_{nirB}$, $P_{ssaG}$, $P_{sifA}$, $P_{sifB}$, $P_{sseA}$, $P_{sseG}$, $P_{sseJ}$.

A further embodiment of the present invention may be a vaccine comprising the live attenuated strains herein disclosed, for use in enhancing immunogenicity against *S. Paratyphi* A and for use in the treatment or prevention of enteric fever and *salmonellosis*. The vaccine may contain a single live attenuated strain or combine more than one live attenuated strain, for example, the vaccine may contain ZH9 and/or one of its derivative strains; ZH9PA, ZH9PL2, ZH9W or ZH9PF. For example, combinations may include ZH9+ZH9PL2, ZH9+ZH9W, ZH9+ZH9PF, preferably the combination is ZH9+ZH9PA.

The term 'immunogenicity' refers to the ability of a particular substance to provoke an immune response.

The term 'vaccine' may be taken to comprise a number of additional elements in addition to the attenuated live strain herein disclosed. The attenuated live strain may be present in a composition together with any other suitable adjuvant, diluent or excipient. Examples of suitable adjuvants, diluents or excipients include, but are not limited to; disodium hydrogen phosphate, soya peptone, potassium dihydrogen phosphate, ammonium chloride, sodium chloride, magnesium sulphate, calcium chloride, sucrose, sterile saline and sterile water.

The vaccine may be administered by any appropriate route, preferably orally or intranasal routes; however the former is the preferred route of administration. The vaccine strain or strains will preferentially be lyophilised by a process such as freeze-drying and will be stored in sachets for later rehydration and oral administration to young children. Alternatively, they may be dispensed into enterically coated capsules for oral administration to older children and adults. For the encapsulated formulation, the lyophilised *Salmonella* will ideally be mixed with a bile-adsorbing resin such as cholestyramine to enhance survival when released from the capsule into the small intestine (Edwards and Slater 2009, Vaccine 27: 3897-3903).

The skilled person will appreciated that the vaccine may contain the aforementioned live attenuated strains (e.g. ZH9 and ZH9PA) of *Salmonella entertica* serovar *Typhi* at a density of $10^8$, $10^9$, $10^{10}$, $10^{11}$ or $10^{12}$ colony-forming units per dose. The dosing regime may involve a single dose or multiple doses, ideally the vaccine will be administered in 1-3 doses.

In a second aspect, the present invention provides for a live attenuated strain of *Salmonella enterica* serovar *Typhi* wherein said strain is modified to express the lipopolysaccharide O4 O-antigens and the flagella proteins of *Salmonella enterica* serovar *Paratyphi* B and *Salmonella enterica* serovar *Typhimurium*.

Figure 2:
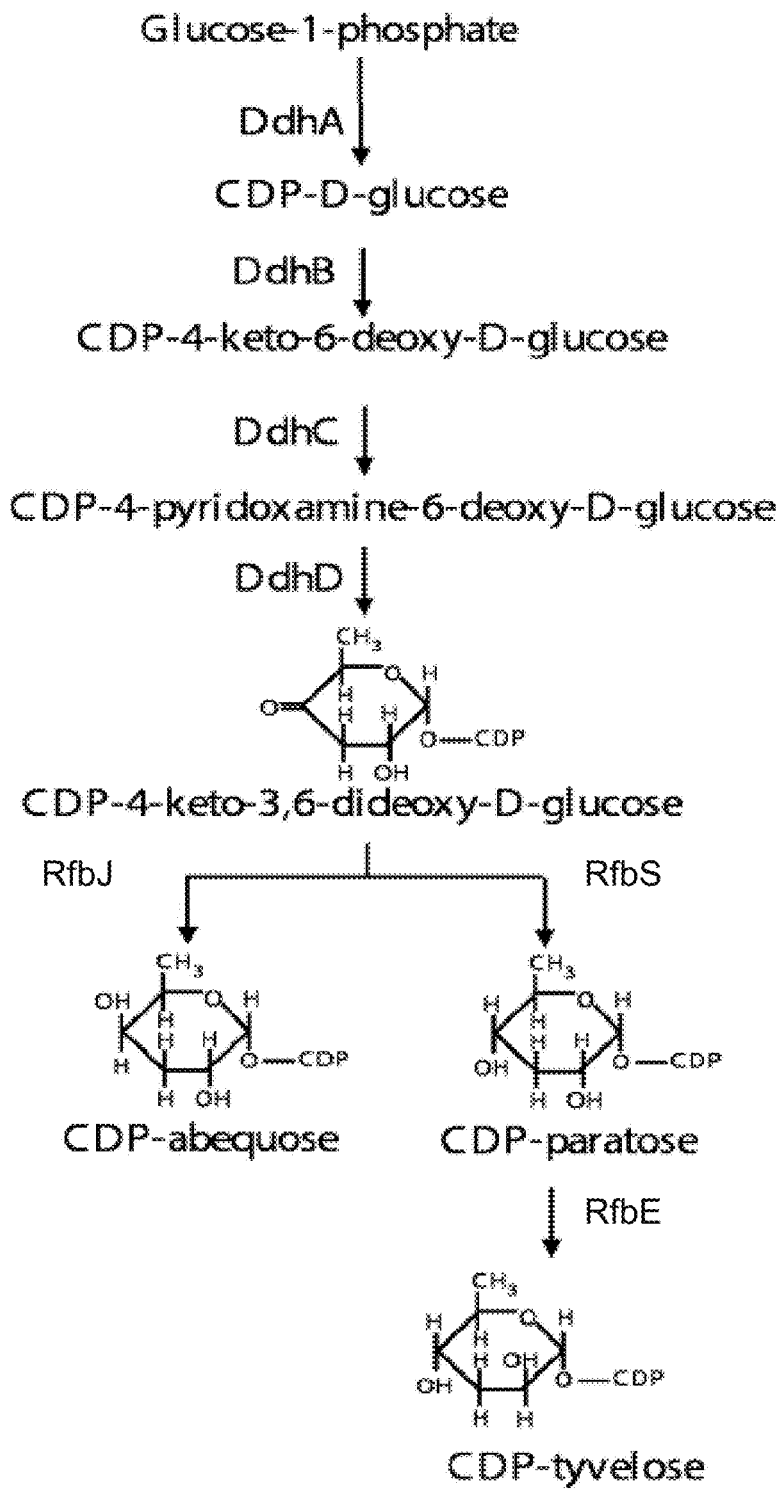
FIG. 2 illustrates the biosynthetic pathways of O-antigen-related CDP-linked sugars in *Salmonella enterica* serovars: *Typhi* and *Enteritidis* (terminating with CDP-tyvelose); *Paratyphi* A (terminating with CDP-paratose); *Paratyphi* B and *Typhimurium* (terminating with CDP-abequose). Enzymes involved at each step are indicated. Adapted from Reeves et al. 2013 Plos One 8: e69306.
Figure 3:
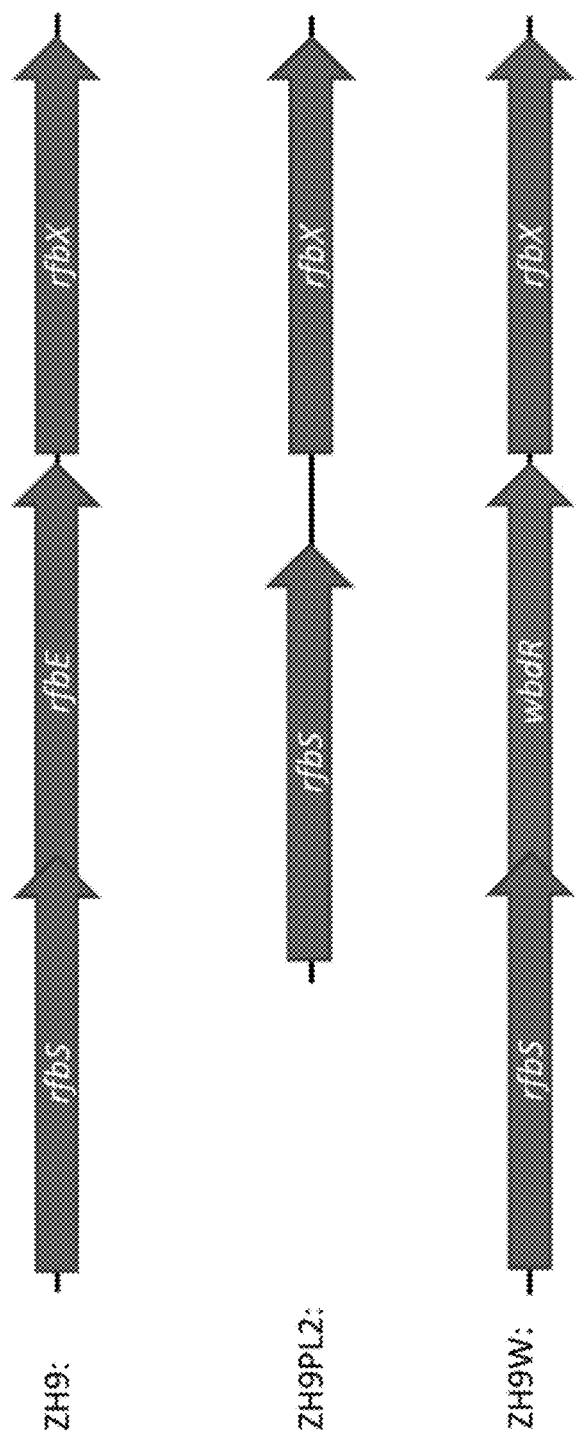
FIG. 3 illustrates part of the wild-type O-antigen locus from *S. Typhi* ZH9 that has been modified by mutation of the wild-type rfbE cistron (SEQ ID NO: 12): either by deletion of the majority of the rfbE cistron to generate *S. Typhi* ZH9PL2 or replacement of the rfbE cistron with spacer DNA comprising the wbdR cistron (SEQ ID NO: 13) maintaining the original reading frame in *S. Typhi* ZH9W.
Figure 6:
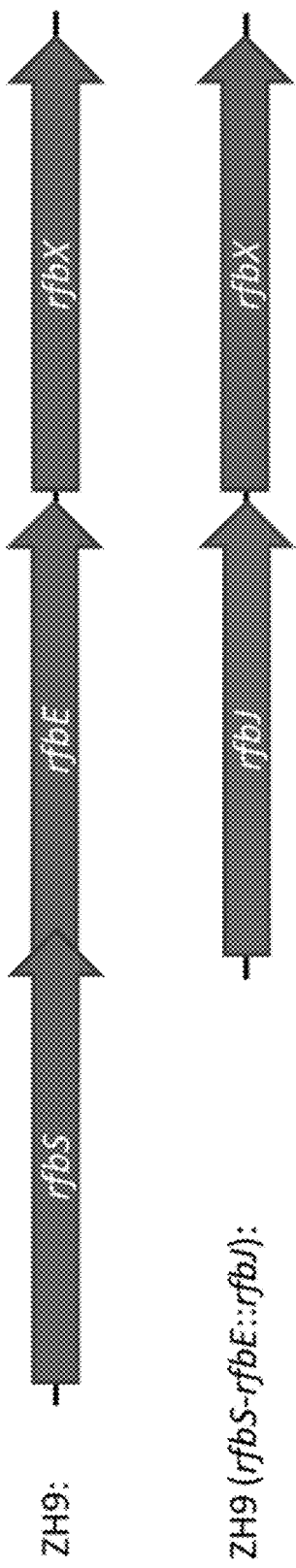
Figure 7:
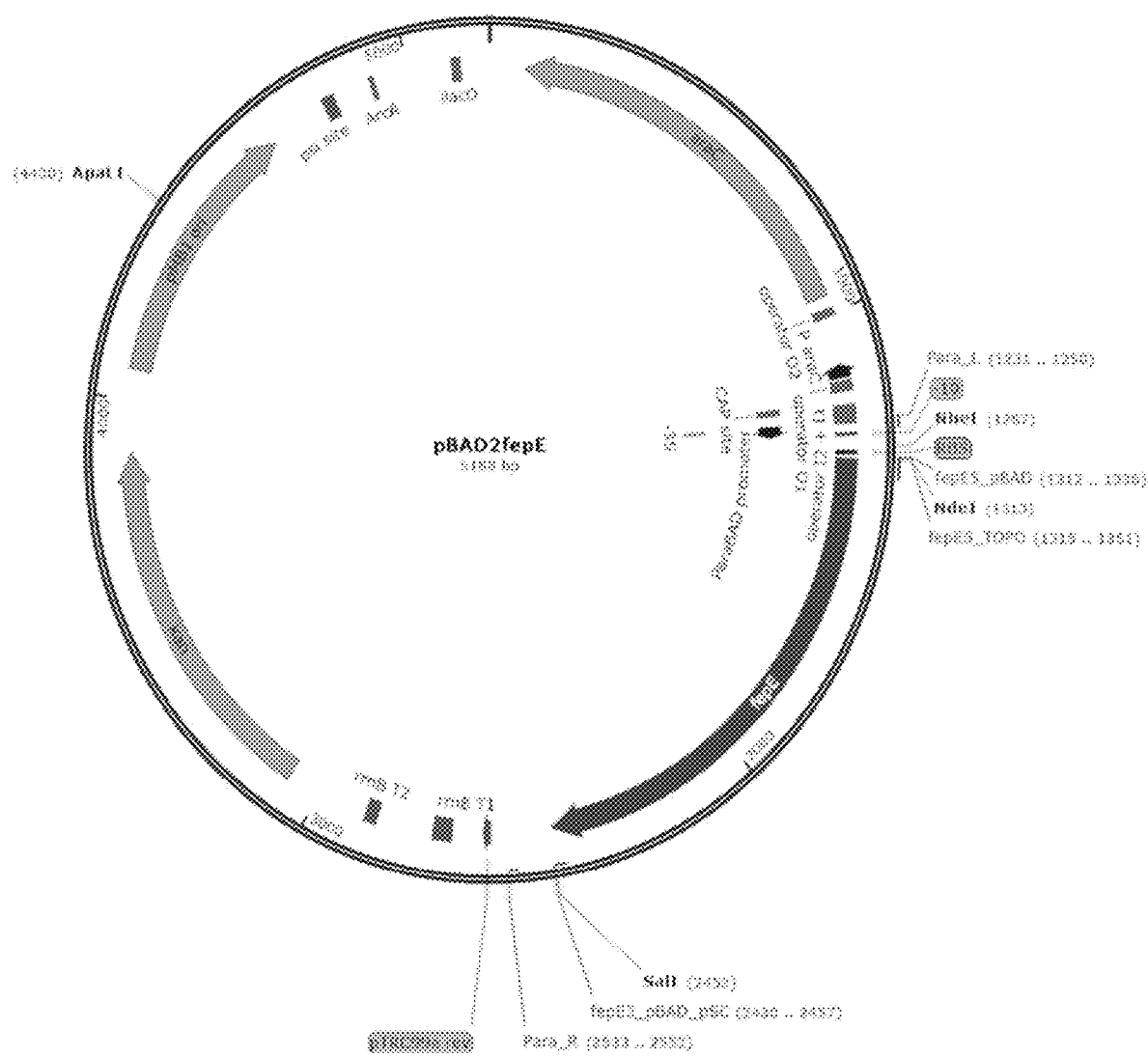

To achieve the above modification, the gene rfbJ (previously called abe), encoding CDP-abequose synthase from *S. Paratyphi* B or *S. Typhimurium*, can be inserted to replace rfbS with or without the simultaneous replacement of rfbE (FIG. 6), as RfbJ is at the equivalent step in the *S. Typhi/Paratyphi* A biosynthetic pathway as CDP-paratose synthase and enables the conversion of CDP-4-keto-3,6-dideoxy-D-glucose to CDP-Abequose (FIG. 2). This would result in the O-antigen repeats containing Abe instead of Tyv, giving the O4 specificity of *S. Paratyphi* B and *S. Typhimurium*. Preferably, rfbS is inactivated via a mutation resulting in a partial or total deletion of the cistron, for example, using Xer-cise wherein a lambda-Red-mediated recombineering approach is used to inactivate the rfbS cistron, followed by Xer recombination to remove the selectable marker gene.

Alternatively to the replacement method described above, and rfbJ may be expressed in trans, either from a plasmid or alternative chromosomal locus, leading to a mixture of 04 and O9 O-antigens, designed to induce antibody responses to *S. Typhi, S. Paratyphi* B and *S. Typhimurium*.

The invention further intends the live attenuated strain, according to the second aspect of the present invention, may have its native fliC gene replaced with the fliC gene of *Salmonella enterica* serovar *Paratyphi* B and/or *Salmonella enterica* serovar *Typhimurium*, such that the conferred serotype is altered from an Hd serotype to a Hb and Hi serotype respectively.

It is further envisaged that the live attenuated strain, according to the second aspect of the present invention, may have the fljBA locus of *Salmonella enterica* serovar *Paratyphi* B and *Salmonella enterica* serovar *Typhimurium* inserted into the chromosome of *Salmonella enterica* serovar *Typhi* or expressed in trans.

Figure 10:
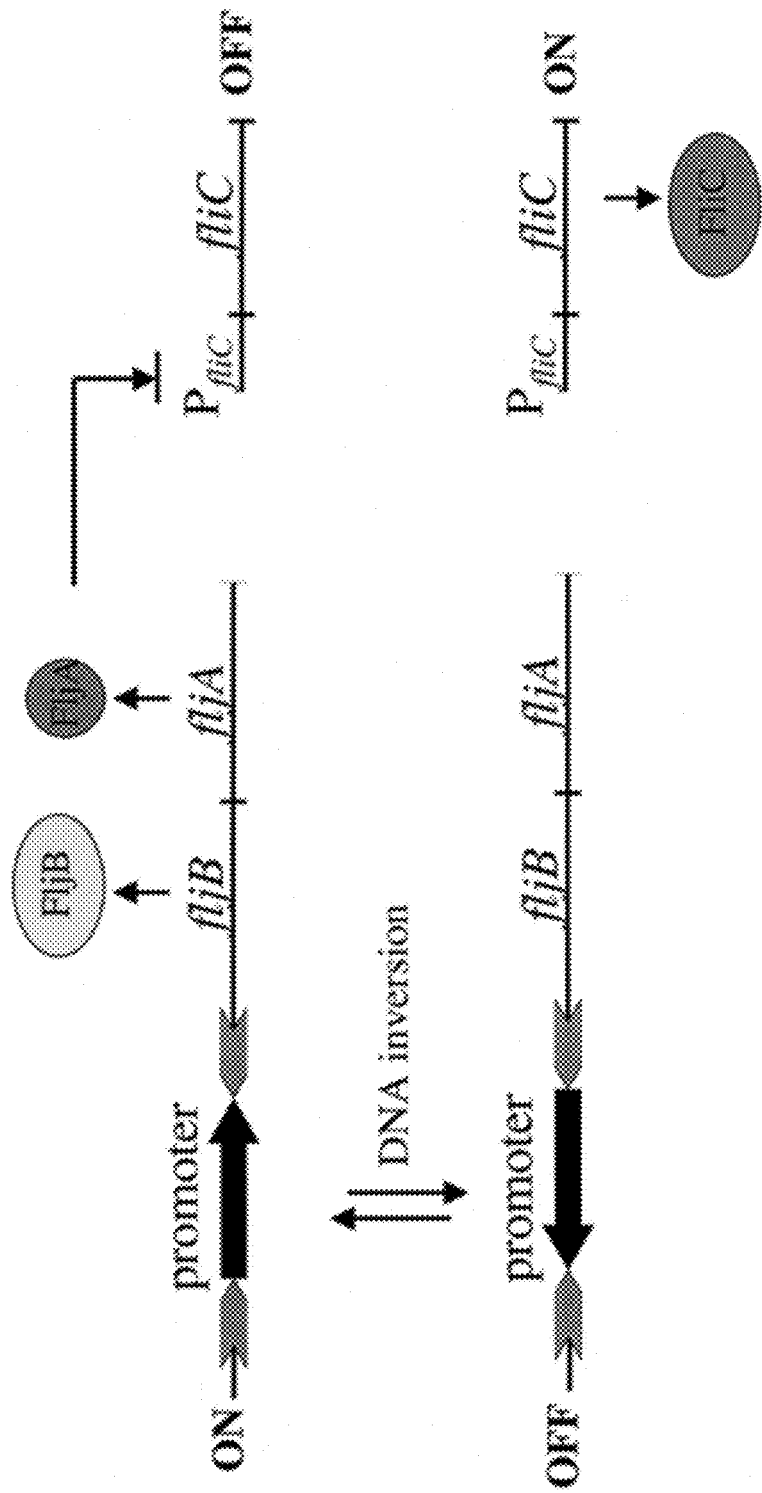

Several serovars of *S. enterica* (including *S. Paratyphi* B and C, and *S. Typhimurium*) have an additional antigenically distinct flagellin gene fljB, which is subject to phase variation such that flagella composed of either FliC or FljB is produced (FIG. 10). Co-transcribed with fljB is fljA, a flagellum-specific sigma factor that represses the fliC gene (Bonifield and Hughes 2003, J. Bacteriol. 185: 567-3574). The fljBA promoter is flanked by the Hin recombinase recognition sites hixL and hixR. Together with enhancer proteins Fis and HU, Hin mediates a reversible DNA inversion between the hix sites such that in one orientation the fljBA promoter transcribes the fljBA operon (SEQ ID NO: 23) producing FIjB flagellin and repressing fliC expression via FIjA, thus generating flagella filaments composed of FIjB. In the opposite orientation there is no expression of the fljBA operon, enabling the production of flagellin consisting of fliC. *S. Typhi* does not express Phase 2 flagella due to deletion of fljB and hin, so has flagella comprised of FliC only (McClelland et al. 2004, Nature Genetics 36: 1268-1274).

It is envisaged that the fljBA locus of *S. Paratyphi* B, *S. Paratyphi* C or *S. Typhimurium* may be inserted into the chromosome of *S. Typhi* or expressed in trans from a plasmid, thus introducing the phase-variable flagella phenotype of the desired serovar. Alternatively, one or both of the hix sites flanking the native promoter of the fljBA operon, or the hin recombinase gene, may be mutated to prevent DNA inversion, leading to constitutive expression such that flagella filaments are comprised of only FIjB. The latter approach may be coupled with the pre-described modification of the *S. Typhi* fliC.

It is further envisaged that the live attenuated strain, according to the second aspect of the present invention, may be further modified to include the additional modifications previously described regarding fepE, gtrC and tviA expression.

A further intended application of the present invention is a vaccine comprising the live attenuated strain, according to the second aspect of the present invention, for use in enhancing immunogenicity against *Salmonella enterica* serovar *Paratyphi* B and/or *Salmonella enterica* serovar *Typhimurium*.

In a third aspect, the present invention provides a live attenuated strain of *Salmonella enterica* serovar *Typhi* wherein said strain is further modified to contain a functional fepE gene, such that long O-antigen chains are generated, preferably wherein the O-antigen chains are 100 repeated units of the trisaccharide backbone in length. The method by which this effect may be achieved, and further details regarding this aspect of the invention, have been previously outlined on pages 12 and 13 of the present application.

In a fourth aspect, the present invention provides a live attenuated strain of *Salmonella enterica* serovar *Typhi* wherein said strain is modified to either constitutively express the gtrC gene, or alternatively, wherein said strain is modified to express the gtrC gene in trans. The method by which this effect may be achieved, and further details regarding this aspect of the invention, have been previously outlined on page 14 and 15 of the present application.

In a fifth aspect, the present invention provides a live attenuated strain of *Salmonella enterica* serovar *Typhi* wherein said strain has its native fliC gene substituted with the fliC gene of *Salmonella enterica* serovar *Paratyphi* A, *Salmonella enterica* serovar *Paratyphi* B, *Salmonella enterica* serovar *Paratyphi* C, *Salmonella enterica* serovar *Typhimurium* and *Salmonella enterica* serovar *Enteritidis*, such that the conferred serotype is altered from an Hd serotype to a Ha, Hb, Hc, Hi and Hg,m serotype respectively. The method by which this effect may be achieved, and further details regarding this aspect of the invention, have been previously outlined on page 12 and 17 of the present application.

In a sixth aspect, the present invention provides a live attenuated strain of *Salmonella enterica* serovar *Typhi* wherein the fljBA locus of *Salmonella enterica* serovar *Paratyphi* B, *Salmonella enterica* serovar *Paratyphi* C and *Salmonella enterica* serovar *Typhimurium* are inserted into the chromosome of *Salmonella enterica* serovar *Typhi* or expressed in trans. The method by which this effect may be achieved, and further details regarding this aspect of the invention, have been previously outlined on pages 17 and 18 of the present application.

In a seventh aspect, the present invention provides a live attenuated strain of *Salmonella enterica* serovar *Typhi* wherein said strain expresses the atypical variants of flagellin of *Salmonella enterica* serovar *Paratyphi* A, *Salmonella enterica* serovar *Paratyphi* B, *Salmonella enterica* serovar *Paratyphi* C, *Salmonella enterica* serovar *Typhimurium* and *Salmonella enterica* serovar *Enteritidis*.

*S. Typhi* isolates are subject to phase variation: one such isolate expresses a variant of FljB called Hz66 from a linear plasmid called pBSSB1 (Baker et al. 2007, Plos Pathogens 3: e59), another flagella variant is Hj which has a 261 bp in-frame deletion of the central region of the Hd fliC gene (Frankel et al. 1989, EMBO J. 8: 3149-3152).

For Hz66 this can be achieved by the inclusion of the pBSSB1 plasmid in the *S. Typhi*-derived vaccine strain. Alternatively, FljB$^{z66}$ or Hj may be expressed from a chromosomal location which may be the location of the deleted fljB gene, the native chromosomal location of fliC (thereby replacing it with a variant), or expressed on a plasmid from its native promoter or from a phagosomally induced promoter such as P$_{ssaG}$ The amino acid sequences of the Hz66 and Hj are described in Schreiber et al. 2015, Nature 5: 7947.

In an eighth aspect, the present invention provides a live attenuated strain of *Salmonella enterica* serovar *Typhi* wherein said strain has inserted a second copy of the tviA gene. The method by which this effect may be achieved, and further details regarding this aspect of the invention, have been previously outlined on page 15 of the present application.

It is envisaged that the live attenuated strains herein disclosed may be administered in isolation or in combination (e.g. ZH9 and ZH9PA), in the form of a vaccine, to give the subject a broad protection against a variety of *S. enterica* serovars, specifically, *Salmonella enterica* serovar *Paratyphi* A and B, and *Salmonella enterica* serovar *Typhimurium*.

The table lists *S. Typhi* ZH9 and its derivative strains altered for LPS and flagellin:

| Strain name | O-antigen | H-antigen |
|---|---|---|
| ZH9 | O9 | Hd |
| ZH9PL2 | O2 (short) | Hd |
| ZH9W | O2 | Hd |
| ZH9PF | O9 | Ha |
| ZH9PA | O2 | Ha |

The invention will now be illustrated in the following examples with reference to the accompanying drawings.

Example 1

To construct *S. Typhi* ZH9 expressing *S. Paratyphi* A LPS, the rfbE gene was deleted in two different ways. In one method of deletion, a spacer cistron wbdR was synthesised flanked with 700 bp of DNA homologous to rfbE upstream gene rfbS and downstream gene rfbX to create a deletion cassette. A NotI restriction site at the 3' end of the spacer cistron was included to clone a dif-flanked antibiotic resistance marker gene cat gene amplified with primers designed with NotI restriction site. The cat gene was amplified from pBRT1N plasmid synthetically generated with 5NotIdifcat and 3NotIdifcat primers designed with dif sequences. *E. coli* TOP10 cells were used for cloning operations to generate the pUCpW_difCAT plasmid. Chromosomal replacement of the rfbE gene with the spacer gene was carried out as described in Bloor and Cranenburgh 2006 (Appl. Environ. Microbiol. 72: 2520-2525). Briefly, *S. Typhi* ZH9 was first transformed with a pLGBEK plasmid coding for λ Red gene functions for integration of linear DNA. Electrocompetent ZH9(pLGBEK) was then transformed with the deletion cassette linearised using SalI and SacI restriction enzymes (SEQ ID NO: 26), and transformants were selected on LB-aro (LB medium containing aromatic amino acids and precursors of aromatic amino acid biosynthesis) agar plates supplemented with 20 μg/ml chloramphenicol. Single colonies were isolated and cultured overnight in LB-aro broth in the absence of antibiotics. Xer recombination deleted the cat gene to generate chloramphenicol-sensitive colonies of ZH9W.

In the other method of deletion, the dif-flanked antibiotic resistance gene cat was amplified with the primers rfbEdelF and rfbEdelR designed with homologous sequences to rfbS and rfbX genes respectively. The difCAT cassette was amplified from the synthetic pMKtetORTDAP plasmid to generate the PL deletion cassette (SEQ ID NO: 27). Electrocompetent ZH9(pLGBEK) were then transformed with the amplified DNA sequence and transformants were selected on LB-aro agar plates supplemented with 20 μg/ml chloramphenicol. Single colonies were isolated and cultured overnight in LB-aro broth in the absence of antibiotics. Xer recombination deleted the cat gene to generate chloramphenicol-sensitive colonies of ZH9PL2.

Example 2

To construct *S. Typhi* ZH9 expressing *S. Paratyphi* A flagellin, the native fliC gene was replaced with the *S. Paratyphi* A fliC. The replacement cassette was synthesised with *S. Paratyphi* A fliC flanked with 700 bp of DNA homologous to the gene fliD upstream of fliC, and a pseudogene downstream of fliC. A NotI restriction site at the 3' end of *S. Paratyphi* A fliC was included to clone a dif-flanked antibiotic resistance marker gene cat gene amplified with primers designed with NotI restriction site. The cat gene was amplified from pBRT1N plasmid synthetically generated with 5NotIdifcat and 3NotIdifcat primers designed with dif sequences. TOP10 *E. coli* cells were used for cloning operations to generate pUCpF_difCAT plasmid. Chromosomal replacement of *S. Typhi* FliC gene with *S. Paratyphi* A FliC was carried out as described in Example 1: electrocompetent ZH9(pLGBEK) was transformed with the pUCpF_difCAT replacement cassette excised using SalI and SacI restriction enzymes (SEQ ID NO: 28), and transformants were selected on LB-aro agar plates supplemented with 20 μg/ml chloramphenicol. Single colonies were isolated and cultured overnight in LB-aro mix broth in the absence of antibiotic. Xer recombination resulted in the deletion of the cat gene to generate chloramphenicol-sensitive colonies of ZH9PF.

To construct *S. Typhi* ZH9 expressing both *S. Paratyphi* A LPS and Flagellin, electrocompetent ZH9PF (pLGBEK) was then transformed with the replacement cassette generated from the pUCpW_difCAT cassette excised using SalI and SacI restriction enzymes, and transformants were selected on LB-aro agar plates supplemented with 20 μg/ml chloramphenicol. Single colonies were isolated and cultured overnight in LB-aro broth in the absence of antibiotic. Xer recombination resulted in the deletion of the cat gene to generate chloramphenicol-sensitive colonies of ZH9PA.

Example 3

To construct the medium copy-number expression plasmid pBRT4tviA (FIG. 11; SEQ ID NO: 29), primers 5tviANdeI and 3tviASalI were used to amplify the tviA gene of *S. Typhi* ZH9 from chromosomal DNA. The PCR product and expression plasmid pBRT4c were digested using NdeI and SalI and ligated to generate the precursor plasmid pBRT4tviAc. An *E. coli* pepA mutant strain was used for cloning operations. The pBRT4tviAc plasmid was transformed into *S. Typhi* ZH9, and transformants were selected on LB-aro agar plates supplemented with 20 μg/ml chloramphenicol. Single colonies were isolated and cultured overnight in LB-aro mix broth in the absence of antibiotic. Xer recombination resulted in the deletion of the cat gene to generate chloramphenicol-sensitive colonies of ZH9 (pBRT4tviA). pBRT4tviA has tviA under the control of the phagosome-induced SPI-2 promoter $P_{ssaG}$, which is not active in nutrient broths such as LB or TB. PCN (Phosphate Carbon Nitrogen minimal medium) with a low concentration of inorganic phosphate was used to induce $P_{ssaG}$.

Example 4

To construct the medium copy number expression plasmid pBAD2fepE (SEQ ID NO: 30), primers fepE5_pBAD and fepE3_pBAD_pSC were used to amplify the fepE gene of *S. Typhimurium* WT05 (aroC, ssaV) from chromosomal DNA. The PCR product and expression plasmid pBAD2 were digested using NdeI and SalI and ligated to generate the plasmid pBAD2fepE. pBAD2fepE has fepE under the control of arabinose promoter, which is not active in nutrient broths such as LB or TB and require the addition of arabinose at 0.02% to induce the expression of the length regulator of very long (VL) O antigen chains. *E. coli* NEB5-alpha was used for cloning operations. The pBAD2fepE plasmid was transformed into S. Typhi ZH9, and transformants were selected on LB-aro agar plates supplemented with 50 μg/ml kanamycin. Single colonies of ZH9 (pBAD2fepE) were isolated and cultured overnight in LB-aro broth supplemented with 50 μg/ml kanamycin and 1:1000 of 20% arabinose to induce expression of LPS with very long (VL) O-antigen chains.

Example 5

Figure 4:
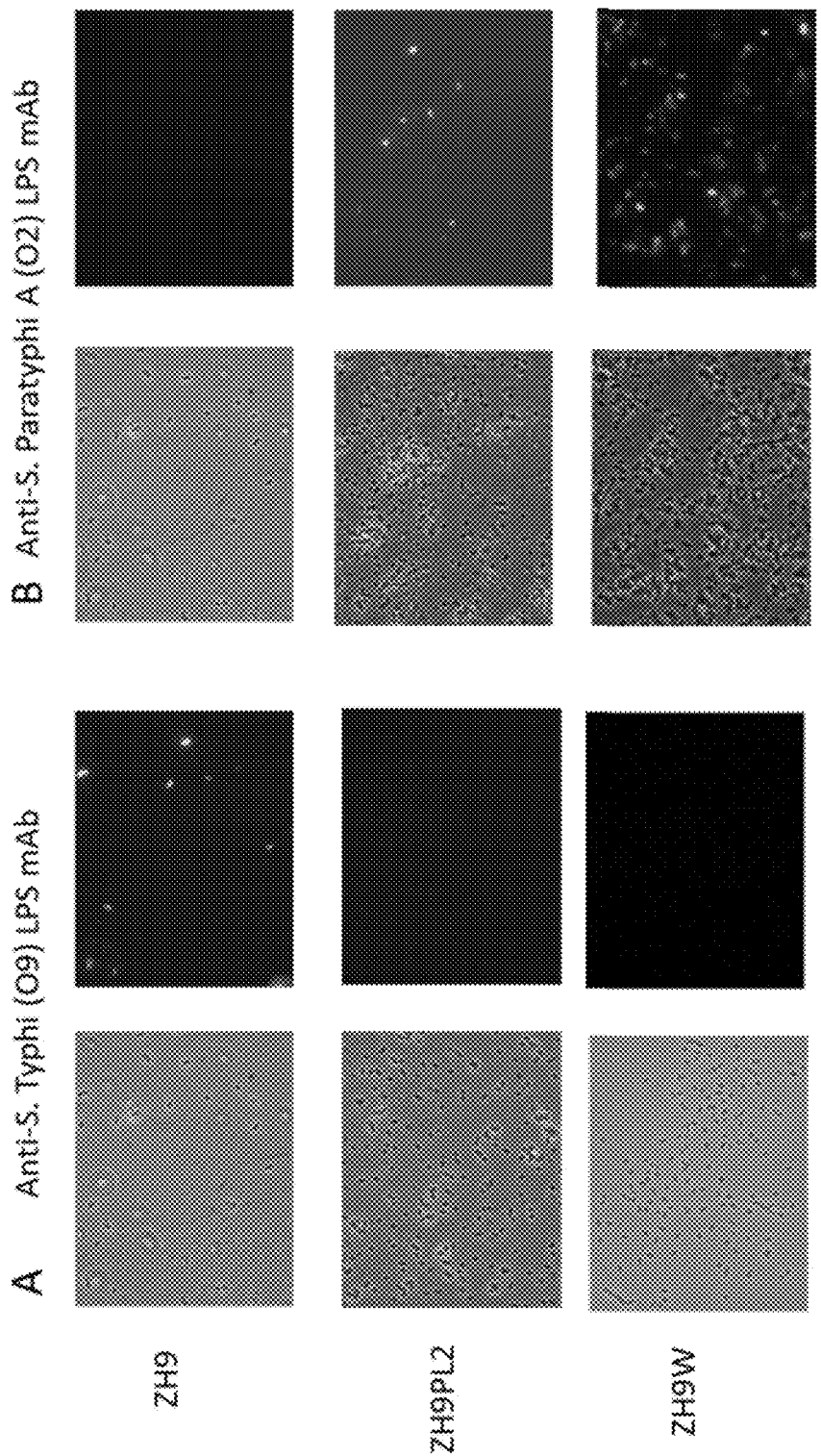
FIG. 4A-B shows mic derivatives thereof, to be produced, offering additional protection against *S. Paratyphi* A. The vaccine therefore has benefits over conventional vaccines which protect only against *S. Typhi*.
Figures 9A, 9B:
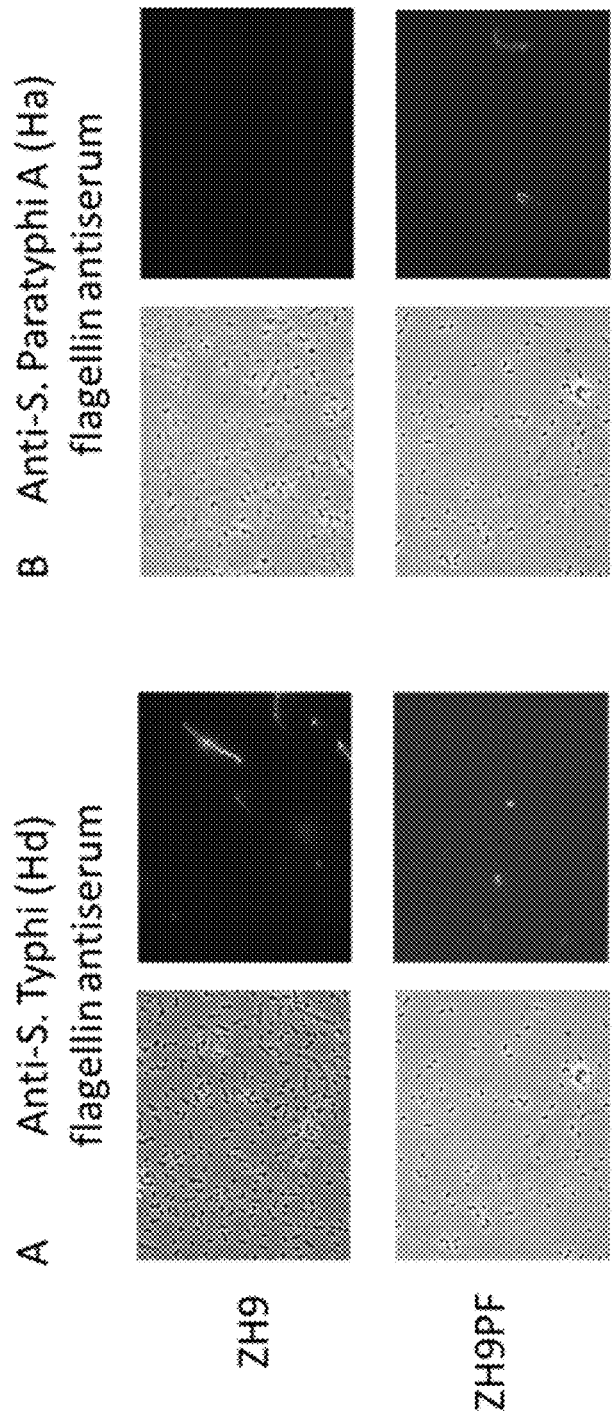
Figure 12:
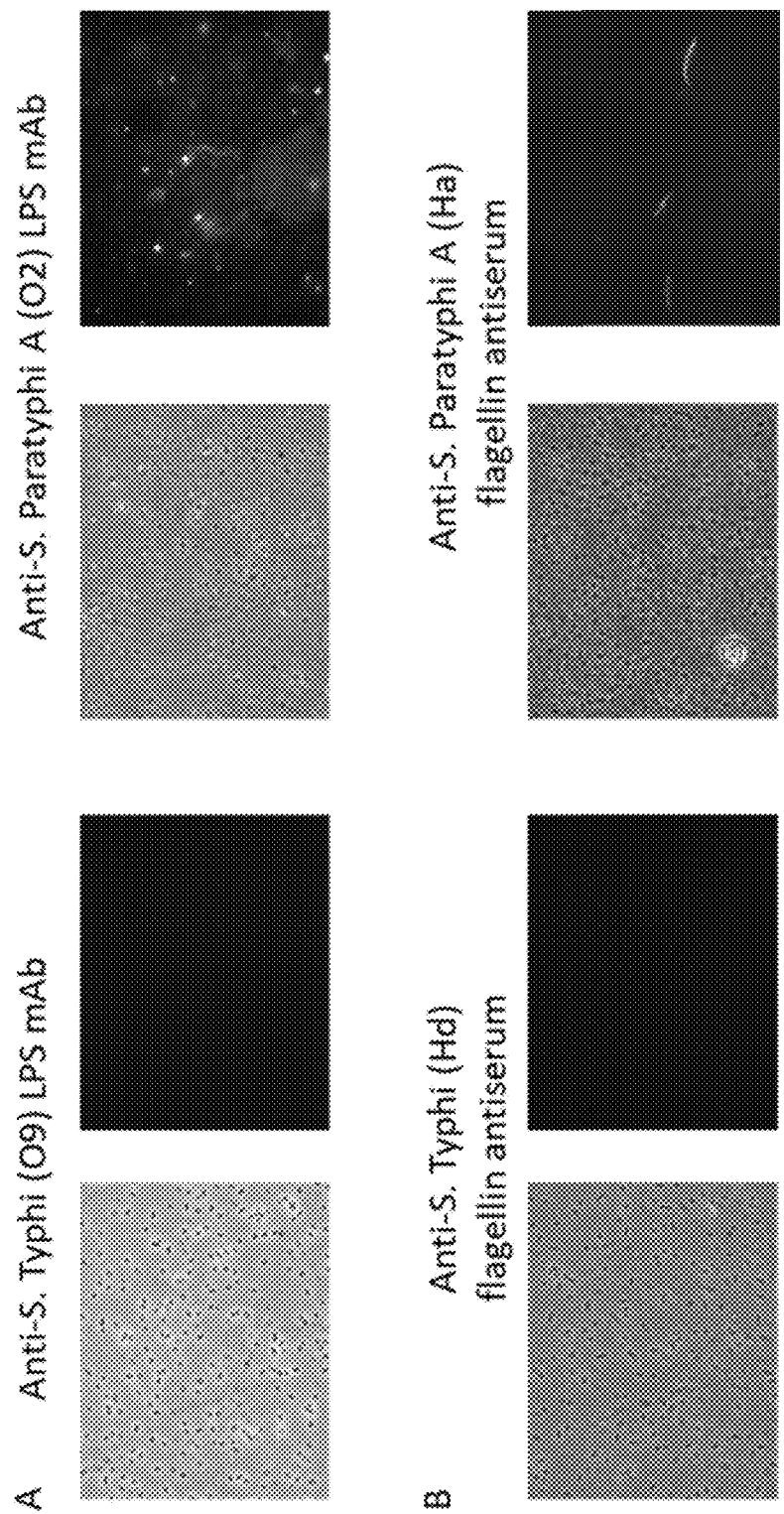
Figure 13:
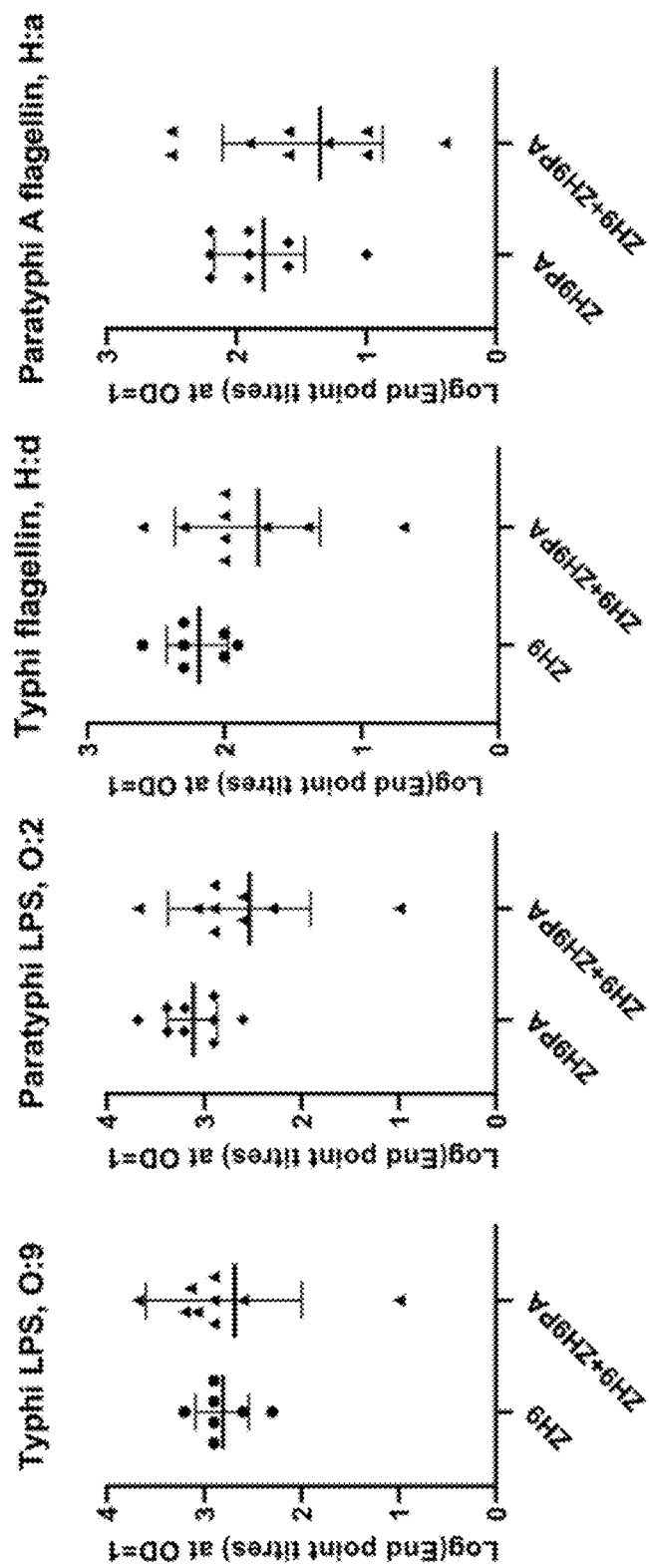

For immunofluorescence microscopy, S. Typhi ZH9 and its derivative strains ZH9W, ZH9PL, ZH9PF and ZH9PA were cultured for 18 hours in LB-aro broth at 37° C. and 200 r.p.m. A volume of each culture equivalent to an optical density of A600=1 was collected and washed in PBS. Pellets were resuspended in 10 μl of PBS with 1 μl of primary antibody and incubated for 10 minutes at ambient temperature. LPS analysis was carried out by staining ZH9, ZH9W, ZH9PL and ZH9PA with one of the following primary antibodies: anti-S. Typhi LPS monoclonal antibody B348M (Genetex), anti-S. Paratyphi A LPS monoclonal antibody (Bio-rad), 0:9 antiserum (SSI) and 0:2 antiserum (SSI). Flagellin analysis was carried out by staining ZH9, ZH9PF and ZH9PA with the following primary antibodies: H:d antiserum (SSI) and H:a antiserum (SSI). Bacterial cells primary stained were then washed in PBS and pellets were resuspended in 10 μl of PBS with 1 μl of secondary antibody conjugated to Dylight 488 fluorochrome. After 10 minutes incubation at room temperature, cells were washed in PBS and a small volume were applied on a microscope slide to be visualised using a fluorescent microscope (Zeiss Axiophot) with attached Zeiss Axiocam camera. Fluorescence imaging demonstrated the conversion of the 09 to the 02 serotype of LPS in ZH9W and ZH9PL (FIG. 4), and the conversion of the Hd flagellin serotype to Ha in ZH9PF (FIG. 9), with both modifications introduced into ZH9PA (FIG. 12).

Figure 5:
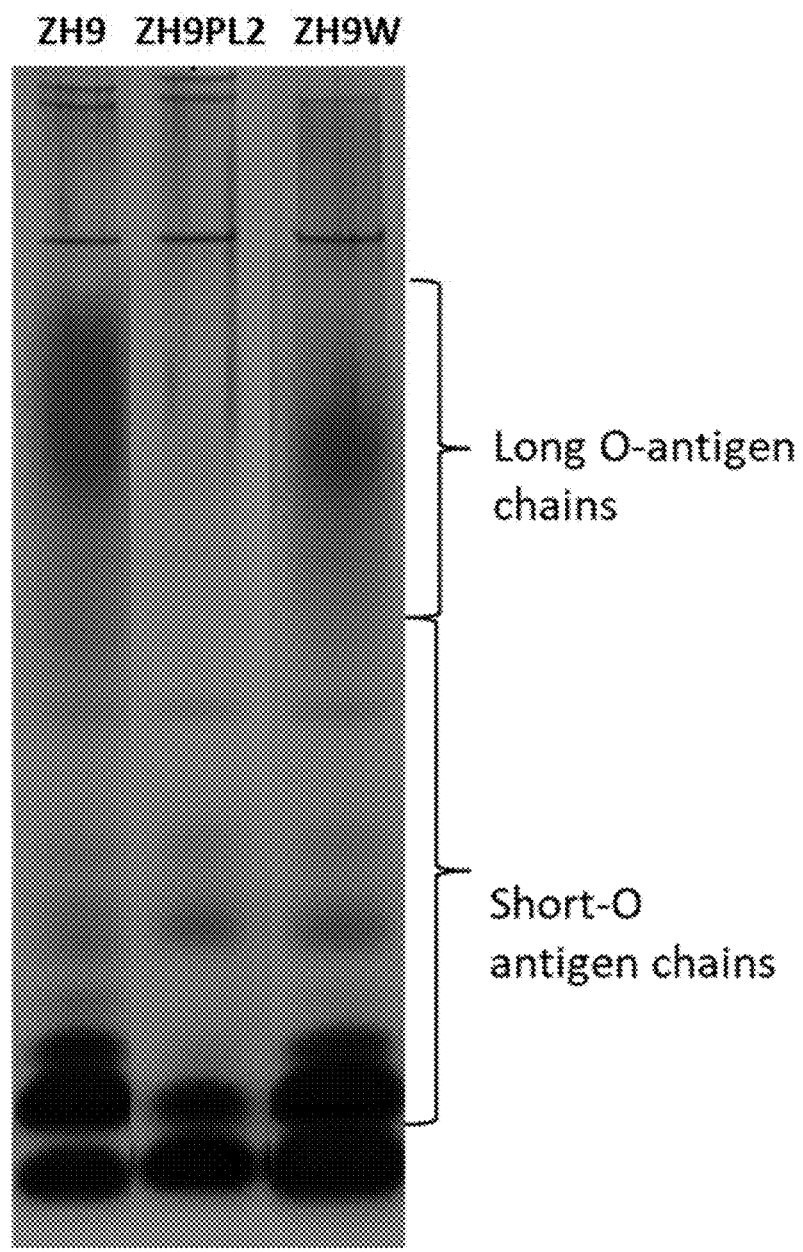
Figure 8:
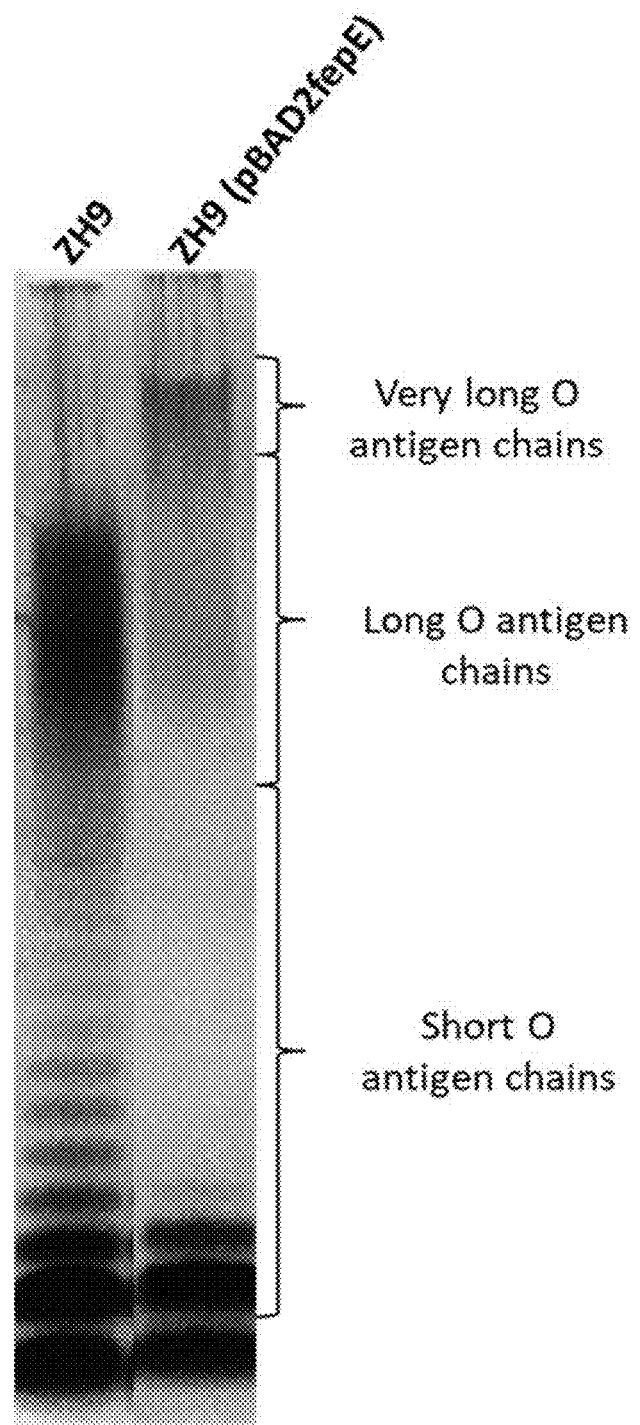

To analyse LPS O-antigen length, ZH9 and ZH9 (pBAD2fepE) pre-cultures were used to inoculate LB-aro broth and grown at 37° C. and 200 r.p.m., with ZH9 (pBAD2fepE) supplemented with 50 μg/ml kanamycin and induced by adding 0.02% arabinose. When exponential phase was reached, 4 mL of each culture was lysed to prepare LPS using an LPS extraction kit (Intron Biotechnology). LPS samples were run on an SDS-PAGE gel and silver-stained. FIG. 5 shows that the replacement of rfbE gene by the spacer gene wbdR is required to express LPS with long O-antigen chains. ZH9(pBAD2fepE) expressed LPS with the very long O-antigen chains not seen in ZH9 (FIG. 8).

Example 6

To assess the immunogenicity of the ZH9PA strain and to confirm retained immunogenicity of both ZH9 and ZH9PA strains when co-administered, an immunogenicity study was conducted in mice. Balb/c animals were immunized via a single subcutaneous immunization with ZH9 alone (1×10⁸ cfu/mouse), ZH9PA alone (1×10⁸ cfu/mouse) or combination of the two ZH9+ZH9PA (0.5×10⁸ cfu ZH9+0.5×10⁸ cfu ZH9PA/mouse). Pre-immune serum samples were collected prior to immunization and terminal serum samples were collected 35 days after immunization. All samples were centrifuged for serum isolation and serum stored at −80° C.

The sera were used to run in house standardized ELISA assays aimed at assessing the titers specific against Salmonella Typhi LPS (O:9) and flagellin (H:d), S. Paratyphi A LPS (O:2) and flagellin (H:a). Briefly, half-area ELISA plates (Corning) were coated with the following specific antigens (all provided by The Native Antigen Company), diluted in 50 mM carbonate/bicarbonate buffer (pH 9.6):

| Antigen | Coating dilution/concentration |
|---|---|
| S. *Typhi* LPS | 1:500 |
| S. *Paratyphi* SLAV LPS | 1:500 |
| S. *Typhi* flagellin | 0.2 μg/mL |
| S. *Paratyphi* SLAV flagellin | 0.5 μg/mL |

Plates were incubated at 4° C. overnight (~16 h). The day after, plates were washed with PBS+0.05% Tween-20 before blocking with Pierce™ Protein-Free (PBS) blocking buffer for 1 hour at 37° C. After washing plates as before, mouse sera from the oral immunogenicity study were added for 1 additional hour at 37° C. A standard curve was also generated for each antigen by using serovar-specific reagents as follows:

| Reagent | Working dilution |
|---|---|
| Monoclonal antibody anti-S. *Typhi* LPS | 1:1000 |
| Monoclonal antibody anti-S. *Paratyphi* A LPS | 1:250 |
| Rabbit antiserum S. *Typhi* flagellin | 1:50 |
| Rabbit antiserum S. *Paratyphi* A flagellin | 1:200 |

Reacting sera and standard curve for *S. Typhi* and *Paratyphi* A LPS were detected using a secondary goat anti-mouse antibody conjugated directly to horse radish peroxidase (HRP), whilst standard curve for *S. Typhi* and *Paratyphi* A flagellin with HRP-conjugated goat anti-rabbit antibody. After washing plates as above, secondary antibodies were added at 1:2000 dilution in Pierce™ Protein-Free (PBS) blocking buffer and incubated at room temperature for 1 hour. Positive sera were revealed using 3,3',5,5'-Tetramethylbenzidine (TMB) substrate and measured using a spectrophotometer at 450 nM. Absorbance (OD) was plotted using a 4 parametric logistic curve of the positive control; then end point titers were determined as logarithm of the dilution value at which the serial dilution curve of each mouse serum met OD equal 1.

FIG. 13 shows that the endpoint titers of antibodies specific for *Typhi* LPS (O:9), *Paratyphi* LPS (O:2), *Typhi* flagellin (H:d) and *Paratyphi* A flagellin (H:a) display no significant differences following immunization with ZH9/ZH9PA alone and the combination of the two. Accordingly, this demonstrates that when the strains are co-administered that immunogenicity is retained.

Sequences Used Throughout the Specification and Forming Part of the Description:

SEQ ID NO: 1 (*S. typhi* fliC Cistron)

```
(S. Typhi fliC cistron)
                                          SEQ ID NO: 1
atggcacaagtcattaatacaaacagcctgtcgctgttgacccagaataac ctgaacaaatcccagtccgcactgggcactgctatcgagcgtttgtcttcc ggtctgcgtatcaacagcgcgaaagacgatgcggcaggacaggcgattgct aaccgttttaccgcgaacatcaaaggtctgactcaggcttcccgtaacgct aacgacggtatctccattgcgcagaccactgaaggcgcgctgaacgaaatc aacaacaacctgcagcgtgtgcgtgaactggcggttcagtctgcgaatggt
```

```
actaactcccagtctgacctcgactccatccaggctgaaatcacccagcgc
ctgaacgaaatcgaccgtgtatccggccagactcagttcaacggcgtgaaa
gtcctggcgcaggacaacaccctgaccatccaggttggtgccaacgacgt
gaaactatcgatattgatttaaaagaaatcagctctaaaacactgggactt
gataagcttaatgtccaagatgcctacaccccgaaagaaactgctgtaacc
gttgataaaactacctataaaatggtacagatcctattacagcccagagc
aatactgatatccaaactgcaattggcggtggtgcaacgggggttactggg
gctgatatcaaatttaaagatggtcaatactatttagatgttaaaggcggt
gcttctgctggtgtttataaagccacttatgatgaaactacaaagaaagtt
aatattgatacgactgataaaactccgttggcaactgcggaagctacagct
attcggggaacggccactataacccacaaccaaattgctgaagtaacaaaa
gagggtgttgatacgaccacagttgcggctcaacttgctgcagcaggggtt
actggcgccgataaggacaatactagccttgtaaaactatcgtttgaggat
aaaaacggtaaggttattgatggtggctatgcagtgaaaatgggcgacgat
ttctatgccgctacatatgatgagaaaacaggtgcaattactgctaaaacc
actacttatacagatggtactggcgttgctcaaactggagctgtgaaattt
ggtggcgcaaatggtaaatctgaagttgttactgctaccgatggtaagact
tacttagcaagcgaccttgacaaacataacttcagaacaggcggtgagctt
aaagaggttaatacagataagactgaaaacccactgcagaaaattgatgct
gccttggcacaggttgatacacttcgttctgacctgggtgcggttcagaac
cgtttcaactccgctatcaccaacctgggcaataccgtaaataacctgtct
tctgcccgtagccgtatcgaagattccgactacgcaaccgaagtctccaac
atgtctcgcgcgcagattctgcagcaggccggtacctccgttctggcgcag
gcgaaccaggttccgcaaaacgtcctctctttactgcgttaa
```

SEQ ID NO: 2 (*S. paratyphi* A fliC Cistron)

```

-continued accggtgctgtgaaatttggcggtgcgaatggtaaaactgaagttgtgacc accgttgatggtaatacttatcaggctagtgatgtaaaagggcataatttc cagagtggtggcgctttaagcgaggctgtaaccactaaaactgaaaacccg ctggctaaaattgatgccgcgctggcgcaagttgatgcgctgcgttctgac ttgggtgcggttcagaaccgtttcaactccgctatcaccaacctgggcaat accgtaaacaacctgtctgaagcccgtagccgtatcgaagattccgactac gcgaccgaagtctccaacatgtcccgcgcgcagattctgcagcaggccggt acctccgttctggcgcaggcgaaccaggttccgcaaaacgtcctctcttta ctgcgttaa SEQ ID NO: 4 (*S. paratyphi* B fljB Cistron)

(*S. Paratyphi* B fljB cistron)

SEQ ID NO: 4 atggcacaagtaatcaacactaacagtctgtcgctgctgacccagaataac ctgaacaaatcccagtccgcactgggcaccgctatcgagcgtctgtcttct ggtctgcgtatcaacagcgcgaaagacgatgcggcaggtcaggcaattgct aaccgtttcaccgcgaacatcaaaggcctgactcaggcttcccgtaacgct aacgacggtatctccattgcgcagaccactgaaggcgcgctgaacgaaatc aacaacaacctgcagcgtgtgcgtgaactggcggttcagtctgctaacagc actaactcccagtctgacctcgactctatccaggctgaaattacccagcgt ctgaacgaaatcgaccgtgtatccggccagactcagttcaacggcgtgaaa gtcctggcgcaggacaacaccctgaccatccaggttggtgccaacgacggt gaaactatcgatatcgatctgaagcagatcaactctcagaccctgggtctg gactcactgaacgtgcagaaagcgtatgatgtgaaagatacagcagtaaca acgaaagcttatgccaataatggtactacactggatgtatcgggtcttgat gatgcagctattaaagcggctacgggggggtacgaatggtacggcttctgta accggtggtgcggttaaatttgacgcagataataacaagtactttgttact attggtggctttactggtgctgatgccgccaaaaatggcgattatgaagtt aacgttgctactgacggtacagtaacccttgcggctggcgcaactaaaacc acaatgcctgctggtgcgacaactaaaacagaagtacaggagttaaaagat acaccggcagttgfficagcagatgctaaaaatgccttaattgctggcggc gttgacgctaccgatgctaatggcgctgagttggtcaaaatgtcttatacc gataaaaatggtaagacaattgaaggcggttatgcgcttaaagctggcgat aagtattacgccgcagattacgatgaagcgacaggagcaattaaagctaaa accacaagttatactgctgctgacggcactaccaaaacagcagctaaccaa ctgggtggcgtagacggtaaaaccgaagtcgttactatcgacggtaaaacc tacaatgccagcaaagccgctggtcatgatttcaaagcacaaccagagctg gcggaagcagccgctaaaaccaccgaaaacccgctgcagaaaattgatgcc gcgctggcgcaggtggatgcgctgcgctctgatctgggtgcggtacaaaac cgtttcaactccgctatcaccaacctgggcaataccgtaaacaacctgtct gaagcgcgtagccgtatcgaagattccgactacgcgaccgaagtttccaac -continued atgtctcgcgcgcagattctgcagcaggccggtacttccgttctggcgcag gctaaccaggtcccgcagaacgtgctgtctctgttacgttaa SEQ ID NO: 5 (*S. paratyphi* C fliC Cistron)

(*S. Paratyphi* C fliC cistron)

SEQ ID NO: 5 atggcacaagtcattaatacaaacagcctgtcgctgttgacccagaataac ctgaacaaatcccagtctgctctgggtaccgctatcgagcgtctgtcttcc ggtctgcgtatcaacagcgcgaaagacgatgcggcaggtcaggcgattgct aaccgtttcaccgcgaacatcaaaggtctgactcaggcttcccgtaacgct aacgacggtatctccattgcgcagaccactgaaggcgcgctgaacgaaatc aacaacaacctgcagcgtgtgcgtgaactggcggttcagtctgctaacagc accaactcccagtctgacctcgactccatccaggctgaaatcacccagcgt ctgaacgaaatcgaccgtgtatccggtcagactcagttcaacggcgtgaaa gtcctggcgcaggacaacactctgaccatccaggttggtgccaacgacggt gaaactatcgatatcgatctgaagcagatcaactctcagaccctgggccta gatacgctgaatgtgcagaaaaaatatgatgtgagcgatactgctgtagct gcttcctattccgactcgaaacagaatattgctgttcctgataaaacagct attactgcaaaaattggtgcagcaaccagtggtggtgctggtataaaagca gatattagctttaaagatggcaagtattacgcgactgtcagtggatacgat gatgccgcagatacagataaaaatggaacctatgaagtcactgttgccgca gatacaggagcagttacttttgcgactacaccaacagtggttgacttacca actgatgcaaaagcagtttcaaaagttcaacagaatgatactgaaatagca gcaacaaatgcgaaagctgcattaaaagctgcaggagttgcagatgcagaa gctgatacagctactttagtgaaaatgtcttatacagataataatggcaaa gttattgatggtgggttcgcatttaagacctccggtggttattatgcagca tctgttgataaatctggcgcagctagcttgaaagttactagctacgttgac gctaccactggtaccgaaaaaaactgctgcgaataaattaggtggcgcagac ggtaaaaccgaagttgttactatcgacggtaaaacctacaatgccagcaaa gccgctgggcacaacttcaaagcacagccagagctggcggaagcggctgct acaaccactgaaaacccgctgcagaaaattgatgctgctttggcgcaggtg gatgcgctgcgttctgacctgggtgcggttcagaaccgtttcaactccgct atcaccaacctgggcaataccgtaaataacctgtcttctgcccgtagccgt atcgaagattccgactacgcgaccgaagtttccaacatgtctcgcgcgcag attctgcagcaggccggtacctccgttctggcgcaggcgaaccaggttccg caaaacgtcctctctttactgcgttaa SEQ ID NO: 6 (*S. paratyphi* C fliC Cistron)

(*S. Paratyphi* C fljB cistron)

SEQ ID NO: 6 atggcacaagtaatcaacactaacagtctgtcgctgctgacccagaataac ctgaacaaatcccagtccgcactgggcaccgctatcgagcgtctgtcttcc ggtctgcgtatcaacagcgcgaaagacgatgcggcaggtcaggcgattgct

SEQ ID NO: 7 (*S. typhimurium* fliC Cistron)

(*S. Typhimurium* fliC cistron)

SEQ ID NO: 7 atggcacaagtcattaatacaaacagcctgtcgctgttgacccagaataac
ctgaacaaatcccagtccgctctgggcaccgctatcgagcgtctgtcttcc
ggtctgcgtatcaacagcgcgaaagacgatgcggcaggtcaggcgattgct
aaccgttttaccgcgaacatcaaaggtctgactcaggcttcccgtaacgct
aacgacggtatctctattgcgcagaccactgaaggcgcgctgaacgaaatc
aacaacaacctgcagcgtgtgcgtgaactggcggttcagtctgctaacagc
actaactcacagtctgacctcgactctatccaggctgaaatcacccagcgt
ctgaacgaaatcgaccgtgtatccggtcagactcagttcaacggcgtgaaa
gtcctggcgcaggacaacaccctgaccatccaggttggtgccaacgacggt
gaaactatcgatatcgatctgaagcagatcaactctcagaccctgggtctg
gactcactgaacgtgcagaaagcgtatgatgtgaaagatacagcagtaaca
acgaaagcttatgccaataatggtactacactggatgtatcgggtcttgat
gatacagctatcaaagcggctataggtggtacgactggtacggctgctgta
accggtagtgcggttaaatttgacgcagataataacaagtactttgttact
attggtggctttactggtgctgatgccgccaaaaatggcgattatgaagtt
aacgttgctactgacggtacagtaaccttgcggctggcgcaactaaaacc
acaatgcctgctggtgcgacaactaaaacagaagtacaggagttaaaagat
acaccggcagttgfficagcagatgctaaaaatgcctaattgctggcggc
gttgacgctaccgatgctaatggcgctgagttggtcaaaatgtcttatacc
gataaaaatggtaagacaattgaaggcggttatgcgcttaaagctggcgat
aagtattacgccgcagattacgatgaagcgacaggagcaattaaagctaaa
accacaagttatactgctgctgacggcactaccaaaacagcagctaaccaa
ctgggtggcgtagacggtaaaaccgaagtcgttactatcgacggtaaaacc
tacaatgccagcaaagccgctggtcatgatttcaaagcacaaccagagctg
gcggaagcagccgctaaaaccaccgaaaaccgctgcagaaaattgatgcc
gcgctggcgcaggtggatgcgctgcgctctgatctgggtgcggtacaaaac
cgtttcaactccgctatcaccaacctgggcaataccgtaaacaacctgtct
gaagcgcgtagccgtatcgaagattccgactacgcgaccgaagtttccaac
atgtctcgcgcgcagattctgcagcaggccggtacttccgttctggcgcag
gctaaccaggtcccgcagaacgtgctgtctcttgttacgttaa

SEQ ID NO: 8 (*S. typhimurium* fljB Cistron)

(*S. Typhimurium* fljB cistron)

SEQ ID NO: 8 atggcacaagtaatcaacactaacagtctgtcgctgctgacccagaataac
ctgaacaaatcccagtccgcactgggcaccgctatcgagcgtctgtcttct
ggtctgcgtatcaacagcgcgaaagacgatgcggcaggtcaggcgattgct
aaccgttttaccgcgaacatcaaaggtctgactcaggcttcccgtaacgct
aacgacggtatctccattgcgcagaccactgaaggcgcgctgaacgaaatc
aacaacaacctgcagcgtgtgcgtgaactggcggttcagtctgctaacagc
accaactcccagtctgacctcgactccatccaggctgaaatcacccagcgc
ctgaacgaaatcgaccgtgtatccggccagactcagttcaacggcgtgaaa
gtcctggcgcaggacaacaccctgaccatccaggttggcgccaacgacggt
gaaactatcgatatcgatctgaagcagatcaactctcagaccctgggtctg
gactcactgaacgtgcagaaagcgtatgatgtgaaagatacagcagtaaca
acgaaagcttatgccaataatggtactacactggatgtatcgggtcttgat
gatgcagctattaaagcggctacgggtggtacgaatggtacggcttctgta
accggtggtgcggttaaatttgacgcagataataacaagtactttgttact
attggtggctttactggtgctgatgccgccaaaaatggcgattatgaagtt
aacgttgctactgacggtacagtaaccttgcggctggcgcaactaaaacc
acaatgcctgctggtgcgacaactaaaacagaagtacaggagttaaaagat
acaccggcagttgthcagcagatgctaaaaatgcctaattgctggcggcg
gttacaggatatgccgatactacgattgctttagacaatagtactttaaa
gcctcggctactggtcttggtggtactgaccagaaaattgatggcgattta
aaatttgatgatacgactggaaaatattacgccaaagttaccgttacgggg
ggaactggtaaagatggctattatgaagtttccgttgataagacgaacggt
gaggtgactcttgctggcggtgcgacttccccgcttacaggtggactacct
gcgacagcaactgaggatgtgaaaaatgtacaagttgcaaatgctgatttg
acagaggctaaagccgcattgacagcagcaggtgttaccggcacagcatct
gttgttaagatgtcttatactgataataacggtaaaactattgatggtggt
ttagcagttaaggtaggcgatgattactattctgcaactcaaaataaagat
ggttccataagtattaatactacgaaatacactgcagatgacggtacatcc
aaaactgcactaaacaaactggggtggcgcagacggcaaaaccgaagttgtt
tctattggtggtaaaacttacgctgcaagtaaagccgaaggtcacaacttt
aaagcacagcctgatctggcggaagcggctgctacaaccaccgaaaacccg
ctgcagaaaattgatgctgctttggcacaggttgacacgttacgttctgac
ctgggtgcggtacagaaccgtttcaactccgctattaccaacctgggcaac
accgtaaacaacctgacttctgcccgtagccgtatcgaagattccgactac
gcgaccgaagtttccaacatgtctcgcgcgcagattctgcagcaggccggt
acctccgttctggcgcaggcgaaccaggttccgcaaaacgtcctctcttta
ctgcgttaa -continued

```
ttgacgctaccgatgctaatggcgctgagttggtcaaaatgtcttataccg
ataaaaatggtaagacaattgaaggcggttatgcgcttaaagctggcgata
agtattacgccgcagattacgatgaagcgacaggagcaattaaagctaaaa
ctacaagttatactgctgctgacggcactaccaaaacagcggctaaccaac
tgggtggcgtagacggtaaaaccgaagtcgttactatcgacggtaaaacct
acaatgccagcaaagccgctggtcatgatttcaaagcacaaccagagctgg
cggaagcagccgctaaaaccaccgaaaacccgctgcagaaaattgatgccg
cgctggcgcaggtggatgcgctgcgctctgatctgggtgcggtacaaaacc
gtttcaactctgctatcaccaacctgggcaataccgtaaacaatctgtctg
aagcgcgtagccgtatcgaagattccgactacgcgaccgaagtttccaaca
tgtctcgcgcgcagattctgcagcaggccggtacttccgttctggcgcagg
ctaaccaggtcccgcagaacgtgctgtctctgttacgttaa
```

SEQ ID NO: 9 (*S. Enteritidis* fliC Cistron)

(*S. Enteritidis* fliC cistron)

SEQ ID NO: 9

```
atggcacaagtcattaatacaaacagcctgtcgctgttgacccagaataac
ctgaacaaatctcagtcctcactgagttccgctattgagcgtctgtcctct
ggtctgcgtatcaacagcgcgaaagacgatgcggcaggccaggcgattgct
aaccgcttcacttctaatatcaaaggtctgactcaggcttcccgtaacgct
aacgacggcatttctattgcgcagaccactgaaggtgcgctgaatgaaatc
aacaacaacctgcagcgtgtgcgtgagttgtctgttcaggccactaacggg
actaactctgattccgatctgaaatctatccaggatgaaattcagcaacgt
ctggaagaaatcgatcgcgtttctaatcagactcaatttaacggtgttaaa
gtcctgtctcaggacaaccagatgaaaatccaggttggtgctaacgatggt
gaaaccattaccatcgatctgcaaaaaattgatgtgaaaagccttggcctt
gatgggttcaatgttaatgggccaaaagaagcgacagtgggtgatctgaaa
tccagcttcaagaatgttacgggttacgacacctatgcagcgggtgccgat
aaatatcgtgtagatattaattccggtgctgtagtgactgatgcagcagca
ccggataaagtatatgtaaatgcagcaaacggtcagttaacaactgacgat
gcggaaaataacactgcggttgatctctttaagaccactaaatctactgct
ggtaccgctgaagccaaagcgatagctggtgccattaaaggtggtaaggaa
ggagatacctttgattataaaggcgtgacttttactattgatacaaaaact
ggtgatgacggtaatggtaaggtttctactaccatcaatggtgaaaaagtt
acgttaactgtcgctgatattgccactggcgcgacggatgttaatgctgct
accttacaatcaagcaaaaatgtttatacatctgtagtgaacggtcagttt
acttttgatgataaaaccaaaaacgagagtgcgaaactttctgatttggaa
gcaaacaatgctgttaagggcgaaagtaaaattacagtaaatggggctgaa
tatactgctaacgccacgggtgataagatcaccttagctggcaaaaccatg
tttattgataaaacagcttctggcgtaagtacattaatcaatgaagacgct
gccgcagccaagaaaagtaccgctaacccactggcttcaattgattctgca
ttgtcaaaagtggacgcagttcgttcttctctgggggcaattcaaaaccgt
tttgattcagccattaccaaccttggcaatacggtaaccaatctgaactcc
gcgcgtagccgtatcgaagatgctgactatgcaacggaagtttctaatatg
tctaaagcgcagattctgcagcaggctggtacttccgttctggcgcaggct
aaccaggttccgcaaaacgtcctctctttactgcgttaa
```

SEQ ID NO: 10 (*S. Typhi* tviA Cistron)

(*S. Typhi* tviA cistron)

SEQ ID NO: 10

```
Atgaggtttcatcatttctggcctccgaatgatatctatttcggggttgga
gctgctggcattattgaagaagtgtcactgataacaaatgacagaaattat
ttgtttgtgaacctaaatcgctacagcctgttaaatgccctgaatttttc
acgcgaatgagtgatattaataaaataatcgttatcatttcaagttcgcga
ctaatgccccttgcacgtttttggttgacagagtgcaaaaatgttattgct
gttttcgatgcggcaacatcagtccaggatattatcagaaatgtcagtcaa
caccaaagtggtgaaaagatcttgacggagcagagagattatcgtttcaga
attaaccgtaaggatatagtaaagatgaaatatttcctttcggaaagtggt
atggaagagcttcaggatagatttatgaactcatcatcgactatgtatcgc
tggagaaaagaattggcagtaaaatttggagtacgtgagccgcgctatctg
ttattgccggattcagttactttactgtaa
```

SEQ ID NO: 11 (*S. Typhimurium* fepE)

(*S. Typhimurium* fepE)

SEQ ID NO: 11

```
Atgccatctcttaatgtaaaacaagaaaaaaatcagtcatttgcaggttat
tcactgccgcccgccaacagtcatgaaatcgatttgtttagccttatagag
gtgttatggcaggcgaaacgtcgtattcttgctaccgttttcgcctttgcg
tgcgtggggttgcttctgtcctttctgctgccgcaaaaatggaccagccag
gcgattgtcacaccggcggagtcggtacagtggcaggggctggagagaacg
ttgaccgcgctgcgcgtgttggatatggaggtaagcgttgatcggggcagc
gtatttaatctgtttattaaaaagtttagctcgccctcgctgctggaagaa
tatcttcgttcttctccgtatgtcatggatcaattaaaaggcgcgcaaata
gacgagcaggatcttcaccgggcgattgtcctgctgagcgaaaaaatgaaa
gcggtggacagtaatgtcggcaagaaaaatgaaacgtcgttattcacgtcg
tggacattgagttttaccgcgccgacgcgggaagaagcgcaaaaagtgctg
gctggctatattcagtacatctccgatatcgtcgtgaaagagacgctggaa
aatattcgtaaccagctggaaatcaaaacccgctatgagcaggaaaagctg
gcgatggatcgggtgcgtctcaaaaatcagcttgatgccaatattcaacgt
cttcattattcgctggaaatcgccaacgccgccggtattaagagaccggtt
tacagcaatggtcaggcggtaaaagatgatccggatttttctatttctctc
ggcgcggatggtatttcccgcaaactggaaattgaaaaaggggtaacggac
gtggccgagatcgacggtgatttgcgtaaccgtcaataccatgttgaacaa
ctggcggcaatgaatgtgagtgacgtgaagtttaccccgtttaaatatcaa
```

-continued ctgtcgccgtctctgccagtgaaaaaagatggcccgggtaaagccatcatt
attatcctggcggcgttgattggcggtatgatggcctgcggcggcgtatta
ctgcgtcacgcgatggtctcgcgtaaaatggaaaacgcgctggcgatagat
gaacggttagtctga SEQ ID NO: 12 (*S. Typhi* rfbE Cistron)

(*S. Typhi* rfbE cistron)

SEQ ID NO: 12

Atgaagcttttaattaccggtggatgtggcttccttgggagtaatcttgcc
tcctttgctttaagtcaagggattgatttaattgtattcgataatctatca
cgtaaaggtgcaacagataatttacattggttatcctccttaggaaacttt
gagtttgtacatggtgatattcgcaacaaaaatgatgttacaagattaata
actaagtatatgcctgatagctgttttcatcttgcaggtcaagtggcaatg
actacatctattgacaatccttgtatggattttgaaattaatgtaggtgga
actttaaatttacttgaggcagtacggcagtataattcaaattgtaatata
atttattcatcaacaaataaagtatacggcgatcttgagcaatataaatac
aatgaaacagaaactagatacacttgtgtagataagcctaatggatatgat
gagagcacacaattagatttccactcaccatatggttgttcaaaaggtgct
gcagaccaatacatgcttgattatgcaaggatttttggtttgaatacagtg
gtgttcaggcattcatcaatgtatggtgggagacagtttgctacttatgat
caaggctgggtaggttggttttgtcaaaaagcggttgaaattaaaaatggt
attaataaacccttcactatttctggtaatggtaagcaagttagggatgtt
ttgcatgctgaagatatgatttcgttatatttcactgccttggcaaatgta
tcaaaaattagggggaacgcttttaatattggtggtaccattgtcaacagc
ctatcattacttgaattattcaaattgcttgaagattattgcaacatagat
atgaggttcactaatttacctgtaagggaaagtgatcagcgtgatttgttg
cagatattaaaaaaatcactaatgcaattgactggagcccgaaagtctcgg
caaaagatggtgtccagaaaatgtatgattggactagttctatatga SEQ ID NO: 13 (*E. coli* O157:H7 wbdR Cistron)

(*E. coli* O157:H7 wbdR cistron)

SEQ ID NO: 13

Atgaatttgtatggtatttttggtgctggaagttatggtagagaaacaata
cccattctaaatcaacaaataaagcaagaatgtggttctgactatgctctg
gtttttgtggatgatgttttggcaggaaagaaagttaatggttttgaagtg
ctttcaaccaactgctttctaaaagccccttatttaaaaaagtattttaat
gttgctattgctaatgataagatacgacagagagtgtctgagtcaatatta
ttacacggggttgaaccaataactataaaacatccaaatagcgttgtttat
gatcatactatgataggtagtggcgctattatttctccctttgttacaata
tctactaatactcatatagggaggtttttcatgcaaacatatactcatac
gttgcacatgattgtcaaataggagactatgttacatttgctcctggggct
aaatgtaatggatatgttgttattgaagacaatgcatatataggctcgggt
gcagtaattaagcagggtgttcctaatcgcccacttattattggcgcggga -continued gccattataggtatgggggctgttgtcactaaaagtgttcctgccggtata
actgtgtgcggaaatccagcaagagaaatgaaaagatcgccaacatctatt
taa SEQ ID NO: 14 (*S. Typhi* rfbS Cistron)

(*S. Typhi* rfbS cistron)

SEQ ID NO: 14

Atgaaaattctaataatgggagcgtttgggttccttggatcacgacttaca
tcctacttcgaaagtcgacatactgtgattggcttagcaaggaagaggaac
aatgaagctaccataaataatattatttacacgacagaaaataattggatc
gaaaaaatactagaatttgaaccgaatattattattaacactattgcttgc
tatggaagacataacgaacctgcaacagctttaatagaaagcaatattctt
atgcctatcagagtattagaatctatctcatcacttgatgcagtattcata
aattgtggaacatcactgccaccaaatacgagtttatatgcatatactaaa
caaaaagcaaatgaactcgccgccgccattatagataaagtttgcggtaaa
tatatagagttaaaattggagcatttctatggagcttttgatggagacgat
aagtttaccagtatggttattagacgttgtttaagtaaccagccagtaaag
ttaacatctggtttgcaacagagagatttcttgtatataaaagatctacta
acagcgttcgattgtattataagtaatgttaataatttccccaaatttcat
agtattgaagttggtagtggagaggcgatatcaattcgtgaatatgtagat
actgttaaaaatatcacaaaaagcaattctataattgaatttggcgtggtc
aaagaaagagtaaatgaattgatgtatagttgtgctgatatagcagaactt
gaaaaaataggatggaaaagagagttctctcttgttgatgcattaactgaa
ataattgaagaggaagggaaatga SEQ ID NO: 15 (*S. Typhimurium* rfbJ Cistron)

(*S. Typhimurium* rfbJ cistron)

SEQ ID NO: 15

Atgacctttttgaaagaatatgtaattgtcagtggggcttccggctttatt
ggtaagcatttactcgaagcgctaaaaaaatcggggatttcagttgtcgca
atcactcgagatgtaataaaaaataatagtaatgcattagctaatgttaga
tggtgcagttgggataatatcgaattattagtcgaggagttatcaattgat
tctgcattaattggtatcattcatttggcaacagaatatgggcataaaaca
tcatctctcataaatattgaagatgcaaatgttataaaaccattaaagctt
cttgatttggcaataaaatatcgggcggatatctttttaaatacagatagt
ttttttgccaagaaagattttaattatcaacatatgcggccttatataatt
actaaaagacactttgatgaaattgggcattattatgctaatatgcatgac
atttcatttgtaaacatgcgattagagcatgtatatgggcctggggatggt
gaaaataaatttattccatacattatcgactgcttaaataaaaaacagagt
tgcgtgaaatgtacaacaggcgaacagataagagactttatttttgtagat
gatgtggtaaatgcttatttaactatattagaaaatagaaaagaagtacct
tcatatactgagtatcaagttggaactggtgctggggtaagtttgaaagat
tttctggtttatttgcaaaatactatgatgccaggttcatcgagtatattt -continued gaatttggtgcgatagagcaaagagataatgaaataatgttctctgtagca
aataataaaaatttaaaagcaatgggctggaaaccaaatttcgattataaa
aaaggaattgaagaactactgaaacggttatga SEQ ID NO: 16 (*S. Typhimurium* $P_{ssaG}$ Promoter Region)

(*S. Typhimurium* $P_{ssaG}$ promoter region)

SEQ ID NO: 16

Tattgccatcgcggatgtcgcctgtcttatctaccatcataaacatcat
ttgcctatggctcacgacagtataggcaatgccgtttttatattgcta
attgtttcgccaatcaacgcaaaagtatggcgattgctaaagccgtctc
cctgggcggtagattagccttaaccgcgacggtaatgactcattcatac
tggagtggtagtttgggactacagcctcatttattagagcgtcttaatg
atattacctatggactaatgagttttactcgcttcggtatggatgggat
ggcaatgaccggtatgcaggtcagcagcccattatatcgtttgctggct
caggtaacgccagaacaacgtgcgccggagtaatcgttttcaggtatat
accggatgttcattgctttctaaattttgctatgttgccagtatcctta
cgatgtatttattttaaggaaaagc SEQ ID NO: 17 (*E. coli* araC Repressor and $P_{araBAD}$ Promoter)

(*E. coli* araC repressor and $P_{araBAD}$ promoter)

SEQ ID NO: 17 ttatgacaacttgacggctacatcattcactttttcttcacaaccggca
cggaactcgctcgggctggccccggtgcatttttaaatacccgcgaga
aatagagttgatcgtcaaaaccaacattgcgaccgacggtggcgatagg
catccgggtggtgctcaaaagcagcttcgcctggctgatacgttggtcc
tcgcgccagcttaagacgctaatccctaactgctggcggaaaagatgtg
acagacgcgacggcgacaagcaaacatgctgtgcgacgctggcgatatc
aaaattgctgtctgccaggtgatcgctgatgtactgacaagcctcgcgt
acccgattatccatcggtggatggagcgactcgttaatcgcttccatgc
gccgcagtaacaattgctcaagcagatttatcgccagcagctccgaata
gcgcccttccccttgcccggcgttaatgatttgcccaaacaggtcgctg
aaatgcggctggtgcgcttcatccgggcgaaagaaccccgtattggcaa
atattgacggccagttaagccattcatgccagtaggcgcgcggacgaaa
gtaaacccactggtgataccattcgcgagcctccggatgacgaccgtag
tgatgaatctctcctggcgggaacagcaaaatatcacccggtcggcaaa
caaattctcgtccctgatttttcaccaccccctgaccgcgaatggtgag
attgagaatataacctttcattcccagcggtcggtcgataaaaaaatcg
agataaccgttggcctcaatcggcgttaaacccgccaccagatgggcat
taaacgagtatcccggcagcaggggatcattttgcgcttcagccatact
tttcatactcccgccattcagagaagaaaccaattgtccatattgcatc
agacattgccgtcactgcgtcttttactggctcttctcgctaaccaaac
cggtaaccccgcttattaaaagcattctgtaacaaagcgggaccaaagc
catgacaaaaacgcgtaacaaaagtgtctataatcacggcagaaaagtc -continued cacattgattatttgcacggcgtcacactttgctatgccatagcatttt
tatccataagattagcggatcctacctgacgctttttatcgcaactctc
tactgtttctccatacccgtttttttgggctagcgaattgaggaggaga
tataca SEQ ID NO: 18 (*S. Paratyphi* A rfbE Pseudogene)

(*S. Paratyphi* A rfbE pseudogene)

SEQ ID NO: 18

Ttgaagaggaagagaaatgaagctttaattaccggtggatgtggcttcc
ttgggagtaatcttgcctcctttgctttaagtcaagggattgatttaat
tgtattcgataatctatcacgtaaaggtgcaacagataatttacattgg
ttatcctccttaggaaactttgagtttgtacatggtgatattcgcaaca
aaaatgatgttacaagattaataactaagtatatgcctgatagctgttt
tcatcttgcaggtcaagtggcaatgactacatctattgacaatccttgt
atggattttgaaattaatgtaggtggaactttaaatttacttgaggcag
tacggcagtataattcaaattgtaatataatttattcatcaacaaataa
agtatacggcgatcttgagcaatataaatacaatgaaacagaaactaga
tacacttgtgtagataagcctaatggatatgatgagagcacacaattag
atttccactcaccatatggttgttcaaaaggtgctgcagaccaatacat
gcttgattatgcaaggattttggtttgaatacagtggtgttcaggcat
tcatcaatgtatggtgggagacagtttgctacttatgatcaaggctggg
taggttggttttgtcaaaaagcggttgaaattaaaaatggtattaataa
acccttcactatttctggtaatggtaagcaagttagggatgttttgcat
gctgaagatatgatttcgttatatttcactgccttggcaaatgtatcaa
aaattagggggaacgcttttaatattggtggtaccattgtcaacagcct
atcattacttgaattattcaaattgcttgaagattattgcaacatagat
atgaggttcactaatttacctgtaagggaaagtgatcagcgtgtttttg
ttgcagatattaaaaaaatcactaatgcaattgactggagcccgaaagt
ctcggcaaaagatggtgtccagaaaatgtatgattggactagttctata
tga SEQ ID NO: 19 (*S. typhi* rfbE Locus with a Partial Deletion of rfbE)

(*S. Typhi* rfbE locus with a partial deletion of rfbE)

SEQ ID NO: 19 tcacgacttacatcctacttcgaaagtcgacatactgtgattggcttag
caaggaagaggaacaatgaagctaccataaataatattatttacacgac
agaaaataattggatcgaaaaaatactagaatttgaaccgaatattatt
attaacactattgcttgctatggaagacataacgaacctgcaacagctt
taatagaaagcaatattcttatgcctatcagagtattagaatctatctc
atcacttgatgcagtattcataaattgtggaacatcactgccaccaaat
acgagtttatatgcatatactaaacaaaaagcaatgaactcgccgccg
ccattatagataaagtttgcggtaaatatatagagttaaaattggagca -continued

```
tttctatggagcttttgatggagacgataagtttaccagtatggttatt
agacgttgtttaagtaaccagccagtaaagttaacatctggtttgcaac
agagagatttcttgtatataaaagatctactaacagcgttcgattgtat
tataagtaatgttaataatttccccaaatttcatagtattgaagttggt
agtggagaggcgatatcaattcgtgaatatgtagatactgttaaaaata
tcacaaaaagcaattctataattgaatttggcgtggtcaaagaaagagt
aaatgaattgatgtatagttgtgctgatatagcagaacttgaaaaaata
ggatggaaaagagagttctctcttgttgatgcattaactgaaataattg
aagaggaagggaaatgaaaagcttggtaccgagctcggatccactagta
acggccgccagtgtgctggaattcgccctttaagcggccgcatttaaca
taatatacattatgcgcaccgcggccgcggaaagggcgaattctgcaga
tatccatcacactggcggccgctcgagcatgcatctagagtgaggaaac
tgaggttggttagaattccaagacatcttattattgccgcttcctcttg
gctttcaaagataataattgccggtgttcagttagtaagtgttaaattt
cttttagaaattcttggcgaagaatcatacgctgtatttactcttttaa
ctggattattggtctggtttagcattgcagatattgggattggtagtag
tctacaaaattatatatctgagttgaaagctgatagaaaatcatatgat
gcatatatcaaggccgcagttcatattctattcgcatccttaatcattt
taagctctacattattcttcttatcagataaattatcgtcactatatct
tacttcatttagcgatgaattgaaaaacaactcaggaagttattttttt
atagcaagtatattatttatattcatcggcgttgggagtgtggtctata
aaatattatttgcggaactgttagggtggaaagctaatataattaatgc
attatcttatcttttaggtttttagatgtagttgcgatccattattta
atgccagattcgagtattaccttcgctttagtagcattgtatgctccgg
tagcaatactgcccattatatatatatcgtttcggtatatatatgttct
taaagcgaaagtaaactttaacacctataaattattactatcacgttca
tcagggtttctgatttttttcgtccttatcgataatagttttacaaactg
attatattgtgatgtctcagaaattatctgctgcagatattataaaata
tactgtaacgatgaaaatatttggtttaatgtttttatttatactgcg
gtattacaagcattatggccagtatgtgct
```

SEQ ID NO: 20 (*S. Typhi* rfbE Locus with rfbE Disrupted by wbdR)

(*S. Typhi* rfbE locus with rfbE disrupted by wbdR)

SEQ ID NO: 20

```
aggcttgactacagagcatttagattatgtagttagcaagtttgaagag
ttctttggtttgaatttctaattttgagggggggggattcccctctatg
atttcatgaaaattctaataatgggagcgtttgggttccttggatcacg
acttacatcctacttcgaaagtcgacatactgtgattggcttagcaagg
aagaggaacaatgaagctaccataaataatattatttacacgacagaaa
ataattggatcgaaaaaatactagaatttgaaccgaatattattattaa
cactattgcttgctatggaagacataacgaacctgcaacagctttaata
gaaagcaatattcttatgcctatcagagtattagaatctatctcatcac
ttgatgcagtattcataaattgtggaacatcactgccaccaaatacgag
tttatatgcatatactaaacaaaaagcaaatgaactcgccgccgccatt
atagataaagtttgcggtaaatatatagagttaaaattggagcatttct
atggagcttttgatggagacgataagtttaccagtatggttattagacg
ttgtttaagtaaccagccagtaaagttaacatctggtttgcaacagaga
gatttcttgtatataaaagatctactaacagcgttcgattgtattataa
gtaatgttaataatttccccaaatttcatagtattgaagttggtagtgg
agaggcgatatcaattcgtgaatatgtagatactgttaaaaatatcaca
aaaagcaattctataattgaatttggcgtggtcaaagaaagagtaaatg
aattgatgtatagttgtgctgatatagcagaacttgaaaaaataggatg
gaaaagagagttctctcttgttgatgcattaactgaaataattgaagag
gaagggaaatgaatttgtatggtatttttggtgctggaagttatggtag
agaaacaatacccattctaaatcaacaaataaagcaagaatgtggttct
gactatgctctggtttttgtggatgatgttttggcaggaaagaaagtta
atggttttgaagtgctttcaaccaactgctttctaaaagccccttattt
aaaaaagtattttaatgttgctattgctaatgataagatacgacagaga
gtgtctgagtcaatattattacacggggttgaaccaataactataaaac
atccaaatagcgttgtttatgatcatactatgataggtagtggcgctat
tatttctccctttgttacaatatctactaatactcatatagggaggttt
tttcatgcaaacatatactcatacgttgcacatgattgtcaaataggag
actatgttacatttgctcctggggctaaatgtaatggatatgttgttat
tgaagacaatgcatatataggctcgggtgcagtaattaagcagggtgtt
cctaatcgcccacttattattggcgcgggagccattataggtatggggg
ctgttgtcactaaaagtgttcctgccggtataactgtgtgcggaaatcc
agcaagagaaatgaaaagatcgccaacatctatttaatgcggccgcatt
taacataatatacattatgcgcaccgcggccgccagtgtgaggatcctg
tttctgcccgcgaaagcgggcataattaaagaatgaaatatttttata
attaaaagatgaagctgacgtgaggaaactgaggttggttagaattcca
agacatcttattattgccgcttcctcttggctttcaaagataataattg
ccggtgttcagttagtaagtgttaaatttcttttagaaattcttggcga
agaatcatacgctgtatttactcttttaactggattattggtctggttt
agcattgcagatattgggattggtagtagtctacaaaattatatatctg
agttgaaagctgatagaaaatcatatgatgcatatatcaaggccgcagt
tcatattctattcgcatccttaatcattttaagctctacattattcttc
ttatcagataaattatcgtcactatatcttacttcatttagcgatgaat
tgaaaaacaactcaggaagttatttttttatagcaagtatattatttat
attcatcggcgttgggagtgtggtctataaaatattatttgcggaactg
ttagggtggaaagctaatataattaatgcattatcttatcttttaggtt
tttagatgtagttgcgatccattatttaatgccagattcgagtattac
``` cttcgctttagtagcattgtatgctccggtagcaatactgcccattata
tatatatcgtttcggtatatatatgttcttaaagcgaaagtaaacttta
acacctataaattattactatcacgttcatcagggtttctgattttttc
gtccttatcgataatagttttacaaactgattatatattgtgatgtctcag
aaattatctgctgcagatattataaaatatactgtaacgatgaaaatat
ttggtttaatgttttttatttatactgcggtattacaagcattatggcc
agtatgtgctgaattacgagtgaaaatgcagtggagaaagctgcataga
atcattttcctaaatattattggtggggtattttttattggtcttgta
cgttatttatttatgttttaaaggattatatctatagcataattgctaa
cggtatagattataatattagtgggttgttttttgtttactggctgtg
tattttagtataagagtttggtgtgatacatttgctatgttacttcaaa
gtatgaaccaattaaaaattctttggctcatagttccgtgtcaggcatt
aattggtggtgtgactcaatggtatttttgcagagcattatgaatagtt
ggtattttatacggactaattttatcgttctcgctaactgttttttggg
gattgccagtgtattatatgtataagagtaaaaggctagcataatatga
aggtatcattttgtatcccaacgtataatcgagtaaaattcattgaaga
ccttcttgaaagtattaataatcaatcttctcactccttaattgtagaa
gtatgt SEQ ID NO: 21 (*S. Typhi* fepE Pseudogene)

(*S. Typhi* fepE pseudogene)
SE

-continued ttgttggttggatttatttattccaggatgattacaaattacttggtaa
gcatgttttagtggctcattcttatatcaaactttactctttggagt
gagtctggctattttgattcaaaatcataccttaaacctttactacatt
tgtggtcgctgggaattgaagagcaattttatataatatggccagtagt
tatattgctatgctttagaagcaaaaaccataacagaaacatagtatta
tcatgcgcaactatatttataattagctatgcgattagcatttttacaa
tggcatctgatggcggagctaattactactctcccgcatcaagattttg
ggagttaatggctggagcgattatatccacattgagatttataggaata
aacacttcgttatcaaaattaatgtccctgttaggaattatactaatcg
cattatcaataaccatgatagatgaaaagatgtcatttcctggatatat
agcaataatcccaatacttggcgcctctcttataatagcatctaatggt
aatgatttagttgtgtcgaaattgcttagtgttaggcctgttgttttct
ttggtcttattagctatcctctttatttgtggcattggcctatttattc
attctatcgttcaatatttgctggctcaccagactaccatgaattaact
cttcttttattattatcgttcttttttggcgatattaacttattatttaa
ttgaaaaaccactgagaaattccagaagtaaatatatcacagcaatatt
attagcattatctgtatttgggacgggtttaattggcgcatttattttt
catataaatggagttaaagacagggaaatcaataaatcagcaagtgaat
atgcttctgttactgacgtgtacaattattataaatatggagaactact
ccgtggagggatatgtcactcagtacaacttactgctgccatatccaat
ggatgtataaaaaatggcaagcataatatatttatcattggtgattctt
atgcggcggctcttttcaatgggcttctcattatatagataataaagg
ttctgattatataagccaaatgacagatggtaatgctcctcctcta
tttgttgacggtaaagatgatttacagagaagtgtcatcactctaaaca
ataatagaattaatgaaattaaacgtgttcagcctgaggtggttctgct
gacatggtcagttcgaggaacaaatggagtacatgataaaaagttagca
attgatgcgttatcattaaccattaaaaaaattaaagaggcatcccctg
actcaaggattgttttcattggaccagtcccggaatggaatgcaaattt
agttaaaataatatctaactacctgagtgagtttaaaaaaactccacca
ttgtatatgacatatggattaaatagtgaaataagcgagtgggactctt
actttagtaacaatgttccaaaaatgggaattgaatatatcagcata
caaagcattatgtaacgaaagtggatgtcttacaagagttggtaatggt
cctgattttatcactgccgttgattggggacatttaacaaagcctggtt
ctgatttccttttttaataaaattggaaataaaataatcaaatagatagg
ctgttactattacatataaatccaatatggaacatgccagtcatactgt
gtaactgccactatattaacggtgatcgctcaggcggtcaccgaactcg
ataataaagcgaa

SEQ ID NO: 23 (*S. Typhimurium* hin-fljBA Locus)

(*S. Typhimurium* hin-fljBA locus)

SEQ ID NO: 23 tgttgtaattttttatttttaattcattcgtttttttatgcggcttgccgg
aaaatatctgtataaggtagatacgccaataccaaaaataatagctagt -continued tgctgccgaggatggccttctctaatagccgactaatctgttcctgtt
catgtttgttgatcgcccgagggcgccctcccagtcgtccttgcgctct
ggcggcagccagtccggcaagggttcgctcgacaattaattctcgctcc
atctcggccagtgctgacattacatgaaaaaagaatcgcccatcgcgc
tactggtatcaatactatcggttaaagaatggaagtgagctccacgttc
atgtaattctgatattaacgccaccaggttttcacgctgcggcccagt
ctgtctaatttccagacgacaagagtatcgcctttatttacatacttta
acgtcgtttcaggccggggcggtttgcaatcttgccactgatacggtc
ctcaaaaatgcggtcacaatttgcactagtaagcgcattacgctgtaaa
tcgatattttggtcaattgttgacacccgaatatacccaatagtagcca
tgattttctcctttacatcagataaggaagaattttagtcgcttttctc
atggaggattgctttatcaaaaaccttccaaaaggaaaattttatggca
caagtaatcaacactaacagtctgtcgctgctgacccagaataacctga
acaaatcccagtccgcactgggcaccgctatcgagcgtctgtcttctgg
tctgcgtatcaacagcgcgaaagacgatgcggcaggtcaggcgattgct
aaccgtttcaccgcgaacatcaaaggtctgactcaggcttcccgtaacg
ctaacgacggtatctccattgcgcagaccactgaaggcgcgctgaacga
aatcaacaacaacctgcagcgtgtgcgtgaactggcggttcagtctgct
aacagcaccaactcccagtctgacctcgactccatccaggctgaaatca
cccagcgcctgaacgaaatcgaccgtgtatccggccagactcagttcaa
cggcgtgaaagtcctggcgcaggacaacaccctgaccatccaggttggc
gccaacgacggtgaaactatcgatatcgatctgaagcagatcaactctc
agaccctgggtctggactcactgaacgtgcagaaagcgtatgatgtgaa
agatacagcagtaacaacgaaagcttatgccaataatggtactacactg
gatgtatcgggtcttgatgatgcagctattaaagcggctacgggtggta
cgaatggtacggcttctgtaaccggtggtgcggttaaatttgacgcaga
taataacaagtactttgttactattggtggctttactggtgctgatgcc
gccaaaaatggcgattatgaagttaacgttgctactgacggtacagtaa
cccttgcggctggcgcaactaaaaccacaatgcctgctggtgcgacaac
taaaacagaagtacaggagttaaaagatacaccggcagttgtttcagca
gatgctaaaaatgccttaattgctggcggcgttgacgctaccgatgcta
atggcgctgagttggtcaaaatgtcttataccgataaaaatggtaagac
aattgaaggcggttatgcgcttaaagctggcgataagtattacgccgca
gattacgatgaagcgacaggagcaattaaagctaaaactacaagttata
ctgctgctgacggcactaccaaaacagcggctaaccaactgggtggcgt
agacggtaaaaccgaagtcgttactatcgacggtaaaaacctacaatgcc
agcaaagccgctggtcatgatttcaaagcacaaccagagctggcggaag
cagccgctaaaaccaccgaaaacccgctgcagaaaattgatgccgcgct
ggcgcaggtggatgcgctgcgctctgatctgggtgcggtacaaaaccgt
ttcaactctgctatcaccaacctgggcaataccgtaaacaatctgtctg

```
aagcgcgtagccgtatcgaagattccgactacgcgaccgaagtttccaa
catgtctcgcgcgcagattctgcagcaggccggtacttccgttctggcg
caggctaaccaggtcccgcagaacgtgctgtctctgttacgttaattta
tttcgttttattcagccccgtgaattcggggcttttttcatttagcatag
atgaatatatatttatggaatgtatggctgtaaatgatatttcctacgg
gcgagaagctgaaatatggccgcgggattattctatgcttgctcgtcga
gttcaatttctacgttttaatgatatccctgttcgattggtgagtaata
atgcccggataatcacaggctacattgcgaagtttaatccgaaggaaaa
tttgattctggcttcggataaacctaaaggaaataagcgcattgaagtt
aaactagagtctctggcaattcttgaagaattatcaggtaatgacgctt
ttaatctttcgctggtgccggctgacggatttaatcttcagcaatatac
tccatcaagaagagattatttctcgatttgcaataagtgctataaacag
ggagtcggtatcaaaatctatatgaagtatggacaggttttgactggca
aaacgacaggcgtaaatgcgtgtcaggttggtgtgaggacatccaatgg
caatcatatgcaagttatgtttgactgggtgagcaggatcacgtcttcg
gactacgctgaataacgcctacggtaataaaaaaattccgtgagaaagt
aaaacttaggggctaccggaggggacctaatgaacggaggtcatggaa
ggtattcatcgtgccagactcttgctcttgtcagaagaaggtaaaagta
```

SEQ ID NO: 24 (Bacteriophage Lambda Tandem $P_R$ and $P_L$ Promoters)

```
(Bacteriophage lambda tandem P_R and P_L promoters)
                                    SEQ ID NO: 24
Acgttaaatctatcaccgcaagggataaatatctaacaccgtgcgtgtt
gactattttacctctggcggtgataatggttgcatgtactaaggaggtt
gtatggaacaacgcataaccctgaaagattatgcaatgcgctttgggca
aaccaagacagctaaagatctctcacctaccaaacaatgccccctgca
aaaaataaattcatataaaaaacatacagataaccatctgcggtgataa
attatctctggcggtgttgacataaataccactggcggtgatactgagc
acatcagcaggacgcactgaccaccatgaaggtgacgctcttaaaaatt
aagccctgaagaagggcagcattcaaagcagaaggctttggggtgtgtg
atacgaaacgaagcattgggatctatcgatgcatgccatggtacccggg
agctcgaattaattctagaaataattttgtttaactttaagaaggagat
ata
```

SEQ ID NO: 25 (Bacteriophage Lambda Thermo-Labile Repressor cI857 Cistron)

```
(Bacteriophage lambda thermo-labile repressor
cI857 cistron)
                                    SEQ ID NO: 25
Atgagcacaaaaaagaaaccattaacacaagagcagcttgaggacgcac
gtcgccttaaagcaatttatgaaaaaagaaaaatgaacttggcttatc
ccaggaatctgtcgcagacaagatggggatggggcagtcaggcgttggt
gctttatttaatggcatcaatgcattaaatgcttataacgccgcattgc
```

```
ttgcaaaaattctcaaagttagcgttgaagaatttagcccttcaatcgc
cagagaaatctacgagatgtatgaagcggttagtatgcagccgtcactt
agaagtgagtatgagtaccctgttttttctcatgttcaggcagggatgt
tctcacctaagcttagaacctttaccaaaggtgatgcggagagatgggt
aagcacaaccaaaaaagccagtgattctgcattctggcttgaggttgaa
ggtaattccatgaccgcaccaacaggctccaagccaagctttcctgacg
gaatgttaattctcgttgaccctgagcaggctgttgagccaggtgattt
ctgcatagccagacttgggggtgatgagtttaccttcaagaaactgatc
agggatagcggtcaggtgtttttacaaccactaaacccacagtacccaa
tgatcccatgcaatgagagttgttccgttgtggggaaagttatcgctag
tcagtggcctgaagagacgtttggctaa
```

SEQ ID NO: 26 (pUCpW_difCAT rfbE Deletion Cassette)

```
(pUCpW_difCAT rfbE deletion cassette)
                                    SEQ ID NO: 26
tcgacatactgtgattggcttagcaaggaagaggaacaatgaagctacc
ataaataatattatttacacgacagaaaataattggatcgaaaaaatac
tagaatttgaaccgaatattattattaacactattgcttgctatggaag
acataacgaacctgcaacagctttaatagaaaagcaatattcttatgcct
atcagagtattagaatctatctcatcacttgatgcagtattcataaatt
gtggaacatcactgccaccaaatacgagtttatatgcatatactaaaca
aaaagcaaatgaactcgccgccgccattatagataaagtttgcggtaaa
tatatagagttaaaattggagcatttctatggagcttttgatggagacg
ataagtttaccagtatggttattagacgttgtttaagtaaccagccagt
aaagttaacatctggtttgcaacagagagatttcttgtatataaagat
ctactaacagcgttcgattgtattataagtaatgttaataatttcccca
aatttcatagtattgaagttggtagtggagaggcgatatcaattcgtga
atatgtagatactgttaaaaatatcacaaaaagcaattctataattgaa
tttggcgtggtcaaagaaagagtaaatgaattgatgtatagttgtgctg
atatagcagaacttgaaaaaataggatggaaaagagagttctctcttgt
tgatgcattaactgaaataattgaagaggaagggaaatgaatttgtatg
gtattttggtgctggaagttatggtagagaaacaataccccattctaaa
tcaacaaataaagcaagaatgtggttctgactatgctctggttttttgtg
gatgatgttttggcaggaaagaaagttaatggttttgaagtgctttcaa
ccaactgctttctaaaagccccttatttaaaaaagtattttaatgttgc
tattgctaatgataagatacgacagagagtgtctgagtcaatattatta
cacggggttgaaccaataactataaaacatccaaatagcgttgtttatg
atcatactatgataggtagtggcgctattatttctcccctttgttacaat
atctactaatactcatatagggaggttttttcatgcaaacatatactca
tacgttgcacatgattgtcaaataggagactatgttacatttgctcctg
gggctaaatgtaatggatatgttgttattgaagacaatgcatatatagg
```

-continued ctcgggtgcagtaattaagcagggtgttcctaatcgcccacttattatt ggcgcgggagccattataggtatgggggctgttgtcactaaaagtgttc ctgccggtataactgtgtgcggaaatccagcaagagaaatgaaaagatc gccaacatctatttaatgcggccgcatttaacataatatacattatgcg caccgcccgaacaccactcgccacaaaaaaccgccggaacgtccaaaag tacgggttttgctgcccgcaaacgggctgttctggtgttgctagtttgt tatcagaatcgcagatccggcttcagccggtttgccggctgaaagcgct atttcttccagaattgccatgattttttccccacgggaggcgtcactgg ctcccgtgttgtcggcagctttgattcgataagcagcatcgcctgtttc aggctgtctatgggccggccaaatcagtaagttggcagcatcacccgac gcactttgcgccgaataaatacctgtgacggaagatcacttcgcagaat aaataaatcctggtgtccctgttgataccgggaagccctgggccaactt ttggcgaaaatgagacgttgatcggcacgtaagaggttccaactttcac cataatgaaataagatcactaccgggcgtattttttgagttatcgagat tttcaggagctaaggaagctaaaatggagaaaaaaatcactggatatac caccgttgatatatcccaatggcatcgtaaagaacattttgaggcattt cagtcagttgctcaatgtacctataaccagaccgttcagctggatatta cggcctttttaaagaccgtaaagaaaaataagcacaagttttatccggc ctttattcacattcttgcccgcctgatgaatgctcatccggaattccgt atggcaatgaaagacggtgagctggtgatatgggatagtgttcacccctt gttacaccgttttccatgagcaaactgaaacgttttcatcgctctggag tgaataccacgacgatttccggcagtttctacacatatattcgcaagat gtggcgtgttacggtgaaacctgcctatttccctaaagggtttattg agaatatgttttcgtctcagccaatccctgggtgagtttcaccagttt tgatttaaacgtggccaatatggacaacttcttcgccccccgttttcacc atgggcaaatattatacgcaaggcgacaaggtgctgatgccgctggcga ttcaggttcatcatgccgtttgtgatggcttccatgtcggcagaatgct taatgaattacaacagtactgcgatgagtggcagggcggggcgtaattt ttttaaggcagttattggtgcccttaaacgcctggttgctacgcctgaa taagtgataataagcggatcctaggatggtgttaagcgggcggttttga gatgtaaactcgcccatttaacataatatacattatgcgcaccgcggcc gccagtgtgaggatcctgtttctgcccgcgaaagcgggcataattaaag aatgaaatatttttataattaaaagatgaagctgacgtgaggaaactg aggttggttagaattccaagacatcttattattgccgcttcctcttggc tttcaaagataataattgccggtgttcagttagtaagtgttaaatttct tttagaaaattcttggcgaagaatcatacgctgtatttactcttttaact ggattattggtctggtttagcattgcagatattgggattggtagtagtc tacaaaattatatatctgagttgaaagctgatagaaaatcatatgatgc atatatcaaggccgcagttcatattctattcgcatccttaatcattta agctctacattattcttcttatcagataaattatcgtcactatatctta ctttcatttagcgatgaattgaaaaacaactcaggaagttatttttttat -continued agcaagtatattatttatattcatcggcgttgggagtgtggtctataaa atattatttgcggaactgttagggtggaaagctaatataattaatgcat tatcttatcttttaggttttttagatgtagttgcgatccattatttaat gccagattcgagtattaccttcgctttagtagcattgtatgctccggta gcaatactgcccattatatatatcgtttcggtatatatatgttctta aagcgaaagtaaactttaacacctataaattattactatcacgttcatc agggtttctgattttttcgtccttatcgataatagttttacaaactgat tatattgtgatgtctcagaaattatctggagct SEQ ID NO: 27 (PL rfbE Deletion Cassette)

(PL rfbE deletion cassette)
SEQ ID NO: 27
aataggatggaaaagagagttctctcttgttgatgcattaactgaaata attgaagaggaagggaaatgaaaagcttggtaccgagctcggatccact agtaacggccgccagtgtgctggaattcgccctttaagcggccgcattt aacataatatacattatgcgcaccatccgcttattatcacttattcagg cgtagcaccaggcgtttaagggcaccaataactgccttaaaaaaattac gccccgccctgccactcatcgcagtactgttgtaattcattaagcattc tgccgacatggaagccatcacaaacggcatgatgaacctgaatcgccag cggcatcagcaccttgtcgccttgcgtataatatttgcccatggtgaaa acgggggcgaagaagttgtccatattggccacgtttaaatcaaaactgg tgaaactcacccagggattggctgagacgaaaaacatattctcaataaa ccctttagggaaataggccaggttttcaccgtaacacgccacatcttgc gaatatatgtgtagaaactgccggaaatcgtcgtggtattcactccaga gcgatgaaaacgtttcagtttgctcatggaaaacggtgtaacaagggtg aacactatcccatatcaccagctcaccgtctttcattgccatacggaat tccggatgagcattcatcaggcgggcaagaatgtgaataaaggccgat aaaacttgtgcttattttctttacggtctttaaaaaggccgtaatatc cagctgaacggtctggttataggtacattgagcaactgactgaaatgcc tcaaaatgttctttacgatgccattgggatatatcaacggtggtatatc cagtgatttttttctccatttagcttccttagctcctgaaaatctcga taactcaaaaaatacgcccggtagtgatcttatttcattatggtgaaag ttggaacctcttacgtgccgatcaacgtctcattttcgccaaaagttgg cccagggcttcccggtatcaacagggacaccaggatttatttattctgc gaagtgatcttccgtcacaggtatttattcgaagacgaaagggatgcag gagtcgcataagggatttaacataatatacattatgcgcaccgcggccg cggaaagggcgaattctgcagatatccatcacactggcggccgctcgag catgcatctagagtgaggaaactgaggttggttagaattccaagacatc ttattattgccgcttcctcttggctttcaaa SEQ ID NO: 28 (pUCpF_difCAT fliC Replacement Cassette)

```
(pUCpF_difCAT fliC replacement cassette)
                                         SEQ ID NO: 28
cattccctgaggggcgtcggttacggtattgctctgacgctcaatgtcg atgccgtttacgttcagcttcgcgttttctgctttcaccagctcttgca tattgccggtattggtggtgctgtcataagcgagtagatcgttaagttt tgtatcgccttccaccgtgatcttcatcgtattgtcggtaccgctattg gcggtaagcaccaactggaattcgttctctttgaccttaacgatactgg cggcgataccgctgtcggcgtcattaatggcgtcacggatcgcctccat ggaggtgtcgcctttatccagcttaatttccagcggctctttacgtccc ggctgttcaattttaattgtccgggatgtgaccgacgtatcgcccaact gctctttggtggttgcgaaggtggttttttgtcgccagcgactgcgcggc ggcaagctgggttacgctaatcttataagtccctgcggcagcgcctgcg gtagtactgactttgaggtcctctgtcgtgctggacgccacggtagact taaataaatccgctttatttaacgcggtatttgccgtctggaatttttc taatgcgcttttcaatgtgccataggcggttagctttgccgaattcgcg ctctgctgtttggtaattggcgttaagcgtccttttttcgttctttgtca ggtctgtcaacaactggtctaacggtaagtttgatcccacacctaatga tgaaattgaagccatgccttcttccttttttgattgcaaacagtagttaa gcgcgttatcggcaatctggaggcaaagtttaatgataattttgcaaaa ataatgcgcggaataatgatgcataaagcggctatttcgccgcctaaga aaaagatcgggggaagtgaaaaattttctaaagttcgaaattcaggtgc cgatacaaggggttacggtgagaaaccgtgggcaacagcccaataacatc aagttgtaattgataaggaaaagatcatggcacaagtcattaatacaaa cagcctgtcgctgttgacccagaataacctgaacaaatcccagtccgct ctgggcaccgctatcgagcgtctgtcttccggtctgcgtatcaacagcg cgaaagacgatgcggcaggtcaggcaattgctaaccgtttcaccgcgaa catcaaggtctgactcaggcttcccgtaacgctaacgacggtatctcc attgcgcagaccactgaaggcgcgctgaacgaaatcaacaacaacctgc agcgtgtgcgtgaactggcggttcagtctgctaacagcaccaactccca gtctgacctcgactccatccaggctgaaatcacccagcgcctgaacgaa atcgaccgtgtatccggtcagactcagttcaacggcgtgaaagtcctgg cgcaggacaacaccctgaccatccaggttggtgccaacaacggtgaaac cattgatatcgatctgaaacagatcaactctcagacccctgggtctggat acgctgaatgtgcagaaaaatatgatgtgaagagcgaagcggtcacgc cttcggctacattaagcactactgcacttgatggtgctggcctcaaaac cggaaccggttctacaactgatactggttcaattaaggatggtaaggtt tactataacagcacctctaaaaattattatgttgaagtagaatttaccg atgcgaccgatcaaaccaacaaaggcggattctataaagttaatgttgc tgatgatggtgcagtcacaatgactgcggctaccaccaaagaggctaca actcctacaggtattactgaagttactcaagtccaaaaacctgtggctg
```

```
ctccagctgctatccaggctcagttgactgctgcccatgtgaccggcgc tgatactgctgaaatggttaagatgtcttatacggataaaaacggtaag actattgatggcggtttcggtgttaaagttggggctgatatttatgctg caacaaaaaataaagatggatcgttcagcattaacaccactgaatatac cgataaagacggcaacactaaaactgcactaaaccaactgggtggcgca gacggtaaaactgaagttgtttctatcgacggtaaaacctacaatgcca gcaaagccgctggtcacaactttaaagcacagccagagctggctgaagc ggctgctgcaaccaccgaaaacccgctggctaaaattgatgccgcgctg gcgcaggttgatgcgctgcgttctgacttgggtgcggttcagaaccgtt tcaactccgctatcaccaacctgggcaataccgtaaataacctgtcttc tgcccgtagccgtatcgaagattccgactacgcgaccgaagtttccaac atgtctcgcgcgcagatcctgcagcaggccggtacctccgttctggcgc aggcgaaccaggttccgcaaaacgtcctctcttttactgcgttaatgcgg ccgcatttaacataatatacattatgcgcaccgcccgaacaccactcgc cacaaaaaaccgccggaacgtccaaaagtacgggttttgctgcccgcaa acgggctgttctggtgttgctagtttgttatcagaatcgcagatccggc ttcagccggtttgccggctgaaagcgctatttcttccagaattgccatg attttttcccacgggaggcgtcactggctcccgtgttgtcggcagctt tgattcgataagcagcatcgcctgtttcaggctgtctatgggccggca aatcagtaagttggcagcatcacccgacgcactttgcgccgaataaata cctgtgacggaagatcacttcgcagaataaataaatcctggtgtccctg ttgataccgggaagccctgggccaacttttggcgaaaatgagacgttga tcggcacgtaagaggttccaacttcaccataatgaaataagatcacta ccgggcgtatttttgagttatcgagattttcaggagctaaggaagcta aaatggagaaaaaatcactggatataccaccgttgatatatcccaatg gcatcgtaaagaacattttgaggcatttcagtcagttgctcaatgtacc tataaccagaccgttcagctggatattacggcctttttaaagaccgtaa agaaaaataagcacaagttttatccggcctttattcacattcttgcccg cctgatgaatgctcatccggaattccgtatggcaatgaaagacggtgag ctggtgatatgggatagtgttcacccttgttacaccgttttccatgagc aaactgaaacgttttcatcgctctggagtgaataccacgacgatttccg gcagtttctacacatatattcgcaagatgtggcgtgttacggtgaaaac ctggcctatttccctaaagggtttattgagaatatgttttttcgtctcag ccaatccctgggtgagtttcaccagttttgatttaaacgtggccaatat ggacaacttcttcgcccccgttttcaccatgggcaaatattatacgcaa ggcgacaaggtgctgatgccgctggcgattcaggttcatcatgccgttt gtgatggcttccatgtcggcagaatgcttaatgaattacaacagtactg cgatgagtggcagggcggggcgtaattttttttaaggcagttattggtgc ccttaaacgcctggttgctacgcctgaataagtgataataagcggatcc taggatggtgttaagcgggcggttttgagatgtaaactcgcccatttaa
```

-continued cataatatacattatgcgcaccgcggccgccagtgtgaggatccccggc
gattgattcaccgacacgtggtacacaatcaaggcagcgaaagctgcct
tttttaattccggagcctgtgtaatgaaagaaatcaccgtcactgaacc
tgcctttgtcacccgcttttcctgttctggctcggcctgtcgcgaccat
tgttgtaagggctggaaaatcacgctggataagacgacggttaaaaagt
atctcgccagtaaagacacgacgattcgtaccatcgcgcaagaccatat
tattctgctgaaaaagaacaataatcattgggggggaaattaaactgcct
tcggcgctgggaagttgcccttatctggatgaggaccgtttgtgccggg
tacaaaaacgttaggcgcaaaggcattaagtcatacctgttcctctttc
ccacgggcgcaccatacctataaaaatgaggtacgtaactccctgagtc
ttgcctgtccggaggtaacgtcccgcattttaaacgatcctgacgcaat
ggcgctcggcgaaaaacaatcattcagcagacattcaatactgcgccg
ttattctcaccgcagcaaaagttactcaatctgtttttgcctgagtctga
tcaaccatgccaacagcagtacggaaacggcgctctatgggttgattaa
attcgtcatgtatgcacataaatttgccaaaattgatgatgccgcgctg
ggtgaactggaacaggtgtatgccgcgttacttgagcagttgcagaccg
gcgtgctggcgcaggaattgatgaatatcgcgccggacagcaaggtaaa
aacctcgctggtattgcagatgcagaactatttccgctcgctcccgctt
agtcgtggcagtgttatcctcgatcactatatccagtgtcttctgcggg
tgctgacggcggaagagggcgtttcaatggagcagaaggttagcgatat
tgagtcctcattagcgcgctgtttacaggcggatgagcagcagaagaac
tgggctttcagaaatttaattctctataaaatttgggaaaataatttcc
ccaaccagccgaatg

SEQ ID NO: 29 (tviA Expression Plasmid pBRT4tviA)

(tviA expression plasmid pBRT4tviA)

SEQ ID NO: 29 aacatcgatattgccatcgcggatgtcgcctgtcttatctaccatcata
aacatcatttgcctatggctcacgacagtataggcaatgccgtttttta
tattgctaattgtttcgccaatcaacgcaaaagtatggcgattgctaaa
gccgtctccctgggcggtagattagccttaaccgcgacggtaatgactc
attcatactggagtggtagtttgggactacagcctcatttattagagcg
tcttaatgatattacctatggactaatgagttttactcgcttcggtatg
gatgggatggcaatgaccggtatgcaggtcagcagcccattatatcgtt
tgctggctcaggtaacgccagaacaacgtgcgccggagtaatcgtttc
aggtatataccggatgttcattgctttctaaattttgctatgttgccag
tatccttacgatgtatttattttaaggaaaagccatatgaggtttcatc
atttctggcctccgaatgatatctatttcggggttggagctgctggcat
tattgaagaagtgtcactgataacaaatgacagaaattatttgtttgtg
aacctaaatcgctacagcctgttaaatgccctgaattttttcacgcgaa
tgagtgatattaataaaataatcgttatcatttcaagttcgcgactaat
gccccttgcacgttttttggttgacagagtgcaaaaatgttattgctgtt
ttcgatgcggcaacatcagtccaggatattatcagaaatgtcagtcaac
accaaagtggtgaaaagatcttgacggagcagagagattatcgtttcag
aattaaccgtaaggatatagtaaagatgaaatatttcctttcggaaagt
ggtatggaagagcttcaggatagatttatgaactcatcatcgactatgt
atcgctggagaaaagaattggcagtaaaatttggagtacgtgagccgcg
ctatctgttattgccggattcagttactttactgtaatgtcgacataaa
acgaaaggctcagtcgaaagactgggcctttcgttttatctgttgtttg
tcggtgaacgctctcctgagtaggacaaatccgccgggagcggatttga
acgttgcgaagcaacggcccggagggtggcgggcaggacgcccgccata
aactgccaggcatcaaattaagcagaaggccatcctgacggatggcctt
ttctgcagataaaaggatctaggtgaagatccttttttgataatctcatg
accaaaatcccttaacgtgagttttcgttccactgagcgtcagaccccg
tagaaaagatcaaaggatcttcttgagatcctttttttctgcgcgtaat
ctgctgcttgcaaacaaaaaaaccaccgctaccagcggtggtttgtttg
ccggatcaagagctaccaactcttttccgaaggtaactggcttcagca
gagcgcagataccaaatactgtccttctagtgtagccgtagttaggcca
ccacttcaagaactctgtagcaccgcctacatacctcgctctgctaatc
ctgttaccagtggctgctgccagtggcgataagtcgtgtcttaccgggt
tggactcaagacgatagttaccggataaggcgcagcggtcgggctgaac
ggggggttcgtgcacacagcccagcttggagcgaacgacctacaccgaa
ctgagatacctacagcgtgagctatgagaaagcgccacgcttcccgaag
ggagaaaggcggacaggtatccggtaagcggcagggtcggaacaggaga
gcgcacgagggagcttccaggggaaacgcctggtatctttatagtcct
gtcgggtttcgccacctctgacttgagcgtcgatttttgtgatgctcgt
caggggggcggagcctatggaaaaacgccagcaacgcggcctttttacg
gttcctggccttttgctggccttttgctcacatgttctttcctgcgtta
tcccctgattctgtggataaccgtattaccgcctttgagtgagctgata
ccgctttttcgtgacattcagttcgctgcgctcacggctctggcagtga
atggggtaaatggcactacaggcgccttttatggattcatgcaaggaa
actacccataatacaagaaaagcccgtcacgggcttctcagggcgtttt
atggcgggtctgctatgtggtgctatctgacttttgctgttcagcagt
tcctgccctctgattttccagtctgaccacttcggattatcccgtgaca
ggtcattcagactggctaatgcacccagtaaggcagcggtatcatcaac
aggcttaccgtcttactgtcaaccagacccgccaggataagcaatccg
gcagactggtacagagcatggtcacgggcttacgggcggctctggctt
cggctcgcttttctgcctgtatcaggttcatgagcggccgcggcgcgcc
agcttatcattgataagcttcttgaactctttatcactgataaagacgc
gtcatagacagcctgaaacaggcgatgctgcttatcgaatcaaagctgc
cgacaacacgggagccagtgacgcctcccgtggggaaaaaatcatggca
attctggaagaaatagcgctttcagccggcaaaccggctgaagccggat -continued
ctgcgattctgataacaaactagcaacaccagaacagcccgtttgcggg cagcaaaacccgtacttttggacgttccggcggttttttgtggcgagtg gtgttcgggcggtgcgcgcaagatccattatgttaaacgggcgagttta catctcaaaaccgcccgcttaacaccattcatgagcggccgccagtgtg ctggaattcggcttcatgattttttattcaacgaagagtt SEQ ID NO: 30 (fepE Expression Plasmid pBAD2fepE)

(fepE expression plasmid pBAD2fepE)
SEQ ID NO: 30
gtgcctgtcaaatggacgaagcagggattctgcaaaccctatgctactc cgtcaagccgtcaattgtctgattcgttaccaattatgacaacttgacg gctacatcattcactttttcttcacaaccggcacggaactcgctcgggc tggccccggtgcattttttaaatacccgcgagaaatagagttgatcgtc aaaaccaacattgcgaccgacggtggcgataggcatccgggtggtgctc aaaagcagcttcgcctggctgatacgttggtcctcgcgccagcttaaga cgctaatccctaactgctggcggaaaagatgtgacagacgcgacggcga caagcaaacatgctgtgcgacgctggcgatatcaaaattgctgtctgcc aggtgatcgctgatgtactgacaagcctcgcgtaccgattatccatcg gtggatggagcgactcgttaatcgcttccatgcgccgcagtaacaattg ctcaagcagatttatcgccagcagctccgaatagcgcccttcccctgc ccggcgttaatgatttgcccaaacaggtcgctgaaatgcggctggtgcg cttcatccgggcgaaagaaccccgtattggcaaatattgacggccagtt aagccattcatgccagtaggcgcgcggacgaaagtaaacccactggtga taccattcgcgagcctccggatgacgaccgtagtgatgaatctctcctg gcgggaacagcaaaatatcacccggtcggcaaacaaattctcgtccctg attttttcaccaccccctgaccgcgaatggtgagattgagaatataacct ttcattcccagcggtcggtcgataaaaaaatcgagataaccgttggcct caatcggcgttaaacccgccaccagatgggcattaaacgagtatcccgg cagcaggggatcattttgcgcttcagccatacttttcatactcccgcca ttcagagaagaaaccaattgtccatattgcatcagacattgccgtcact gcgtctttactggctcttctcgctaaccaaaccggtaacccgcttat taaaagcattctgtaacaaagcgggaccaaagccatgacaaaaacgcgt aacaaaagtgtctataatcacggcagaaaagtccacattgattatttgc acggcgtcacactttgctatgccatagcatttttatccataagattagc ggatcctacctgacgcttttatcgcaactctctactgtttctccatac ccgttttttttgggctagcgaattgaggaggagatatacaTatgccatct cttaatgtaaaacaagaaaaaaatcagtcatttgcaggttattcactgc cgcccgccaacagtcatgaaatcgatttgtttagccttatagaggtgtt atggcaggcgaaacgtcgtattcttgctaccgttttcgcctttgcgtgc gtgggggttgcttctgtcctttctgctgccgcaaaaatggaccagccagg cgattgtcacaccggcggagtcggtacagtggcagggggctggagagaac gttgaccgcgctgcgcgtgttggatatggaggtaagcgttgatcggggc -continued
agcgtatttaatctgtgtttattaaaaagtttagctcgccctcgctgctgg aagaatatcttcgttcttctccgtatgtcatggatcaattaaaaggcgc gcaaatagacgagcaggatcttcaccgggcgattgtcctgctgagcgaa aaaatgaaagcggtggacagtaatgtcggcaagaaaaatgaaacgtcgt tattcacgtcgtggacattgagttttaccgcgccgacgcgggaagaagc gcaaaaagtgctggctggctatattcagtacatctccgatatcgtcgtg aaagagacgctggaaaatattcgtaaccagctggaaatcaaacccgct atgagcaggaaaagctggcgatggatcgggtgcgtctcaaaaatcagct tgatgccaatattcaacgtcttcattattcgctggaaatcgccaacgcc gccggtattaagagaccggtttacagcaatggtcaggcggtaaaagatg atccggattttctatttctctcggcgcggatggtatttcccgcaaact ggaaattgaaaaaggggtaacggacgtggccgagatcgacggtgatttg cgtaaccgtcaataccatgttgaacaactggcggcaatgaatgtgagtg acgtgaagtttaccccgtttaaatatcaactgtcgccgtctctgccagt gaaaaaagatggcccgggtaaagccatcattattatcctggcggcgttg attggcggtatgatggcctgcggcggcgtattactgcgtcacgcgatgg tctcgcgtaaaatggaaaacgcgctggcgatagatgaacggttagtctg aGtcgacctgcaggcatgcaagcttggctgttttggcggatgagagaag attttcagcctgatacagattaaatcagaacgcagaagcggtctgataa aacagaatttgcctggcggcagtagcgcggtggtcccacctgaccccat gccgaactcagaagtgaaacgccgtagcgccgatggtagtgtggggtct ccccatgcgagagtagggaactgccaggcatcaaataaaaacgaaaggct cagtcgaaagactgggcctttcgttttatctgttgtttgtcggtgaacg ctctcctgagtaggacaaatccgccgggagcggatttgaacgttgcgaa gcaacggcccggagggtggcgggcaggacgcccgccataaactgccagg catcaaattaagcagaaggccatcctgacggatggccttttgcgtttc tacaaactcttttgtttattttctaaatacattcaaatatgtatccg ctcatgtggccggcccggcctaggaaagccacgttgtgtctcaaaatct ctgatgttacattgcacaagataaaaatatatcatcatgaacaataaaa ctgtctgcttacataaacagtaatacaaggggtgttatgagccatattc aacgggaaacgtcttgctcgaggccgcgattaaattccaacatggatgc tgatttatatgggtataaatgggctcgcgataatgtcgggcaatcaggt gcgacaatctatcgattgtatgggaagcccgatgcgccagagttgtttc tgaaacatggcaaaggtagcgttgccaatgatgttacagatgagatggt cagactaaactggctgacggaatttatgcctcttccgaccatcaagcat tttatccgtactcctgatgatgcatggttactcaccactgcgatcccg ggaaaacagcattccaggtattagaagaatatcctgattcaggtgaaaa tattgttgatgcgctggcagtgttcctgcgccggttgcattcgattcct gtttgtaattgtccttttaacagcgatcgcgtatttcgtctcgctcagg cgcaatcacgaatgaataacggtttggttgatgcgagtgattttgatga

```
cgagcgtaatggctggcctgttgaacaagtctggaaagaaatgcataag
cttttgccattctcaccggattcagtcgtcactcatggtgatttctcac
ttgataaccttattttttgacgaggggaaattaataggttgtattgatgt
tggacgagtcggaatcgcagaccgataccaggatcttgccatcctatgg
aactgcctcggtgagttttctccttcattacagaaacggcttttttcaaa
aatatggtattgataatcctgatatgaataaaattgcagtttcatttgat
gctcgatgagttttctaatcagaattggttaattggttgtaacactgg
cagagcattacgctgacttgacgggacggcggctttgttgaataaatcg
aacttttcctaggccgggccggccacatgaccaaaatcccttaacgtga
gttttcgttccactgagcgtcagacccgtagaaaagatcaaaggatct
tcttgagatcctttttttctgcgcgtaatctgctgcttgcaaacaaaaa
aaccaccgctaccagcggtggtttgtttgccggatcaagagctaccaac
tctttttccgaaggtaactggcttcagcagagcgcagataccaaatact
gtccttctagtgtagccgtagttaggccaccacttcaagaactctgtag
caccgcctacatacctcgctctgctaatcctgttaccagtggctgctgc
cagtggcgataagtcgtgtcttaccgggttggactcaagacgatagtta
ccggataaggcgcagcggtcgggctgaacggggggttcgtgcacacagc ccagcttggagcgaacgacctacaccgaactgagatacctacagcgtga
gctatgagaaagcgccacgcttcccgaagggagaaaggcggacaggtat
ccggtaagcggcagggtcggaacaggagagcgcacgagggagcttccag
ggggaaacgcctggtatctttatagtcctgtcgggtttcgccacctctg
acttgagcgtcgattttttgtgatgctcgtcaggggggcggagcctatgg
aaaaacgccagcaacgcggcctttttacggttcctggccttttgctggc
cttttgctcacttttacggttcctggccttttgctggccttttgctcac
atgtatggtgttaagcgggcggttttgagatgtaaactcgcccgtttaa
cataatggatcttgcgcgcaccgcccgaacaccactcgccacaaaaaac
cgccggaacgtccaaaagtacgggttttgctgcccgcaaacgggctgtt
ctggtgttgctagtttgttatcagaatcgcagatccggcttcagccggt
ttgccggctgaaagcgctatttcttccagaattgccatgatttttttccc
cacgggaggcgtcactggctcccgtgttgtcggcagctttgattcgata
agcagcatcgcctgtttcaggctgtctatgacatgttctttcctgcgtt
atccccaattgtgagcgctcacaatttgctgcggtaagtcgcataaaaa
ccattcttcataattcaatccatttactatgttatgttctgag

The invention claimed is:

1. An attenuated strain of *Salmonella enterica* serovar *Typhi* wherein said strain is modified to express the lipopolysaccharide O2 O-antigens and the flagella proteins of *Salmonella enterica* serovar *Paratyphi* A, wherein the modification of said strain comprises (i) the inactivation of the native rfbE gene of *Salmonella enterica* serovar *Typhi* by the insertion of a spacer region of DNA into the rfbE gene wherein the spacer maintains the reading frame; and ii wherein the native fliC gene of *Salmonella enterica* serovar *Typhi* is substituted with the fliC gene of *Salmonella enterica* serovar *Paratyphi* A or wherein a fliC gene of *Salmonella enterica* serovar *Paratyphi* A is expressed in trans, such that the conferred serotype is altered from an Hd serotype to a Ha serotype.

2. The attenuated strain of claim 1, wherein the spacer region of DNA is the cistron of the *Escherichia coli* gene wbdR.

3. The attenuated strain of claim 1, wherein the strain is further modified to contain a functional fepE gene.

4. The attenuated strain according to claim 1, wherein said strain is ZH9PA.

5. The attenuated strain of claim 1, wherein said strain is further modified to express gtrC.

6. The attenuated strain of claim 1, wherein said strain is further modified to contain an additional copy of the tviA gene under the control of a phagosomally induced promoter.

7. An immunogenic composition comprising the attenuated strain of claim 1.

8. The immunogenic composition of claim 7, further comprising *Salmonella enterica* serovar *Typhi* ZH9 strain.

9. A method of inducing an immune response in a subject to *Salmonella enterica* serovar *Typhi* or *Paratyphi* A comprising administering the immunogenic composition of claim 7.

* * * * *

```

SEQUENCE LISTING

<160> NUMBER OF SEQ ID NOS: 30

<210> SEQ ID NO 1
<211> LENGTH: 1521
<212> TYPE: DNA
<213> ORGANISM: Salmonella typhi

<400> SEQUENCE: 1

```
atggcacaag tcattaatac aaacagcctg tcgctgttga cccagaataa cctgaacaaa      60
tcccagtccg cactgggcac tgctatcgag cgtttgtctt ccggtctgcg tatcaacagc     120
gcgaaagacg atgcggcagg acaggcgatt gctaaccgtt ttaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgcg     300
aatggtacta actcccagtc tgacctcgac tccatccagg ctgaaatcac ccagcgcctg     360
aacgaaatcg accgtgtatc cggccagact cagttcaacg gcgtgaaagt cctggcgcag     420
gacaacaccc tgaccatcca ggttggtgcc aacgacggtg aaactatcga tattgattta     480
aaagaaatca gctctaaaac actgggactt gataagctta atgtccaaga tgcctacacc     540
ccgaaagaaa ctgctgtaac cgttgataaa actacctata aaaatggtac agatcctatt     600
acagcccaga gcaatactga tatccaaact gcaattggcg gtggtgcaac ggggggttact     660
ggggctgata tcaaatttaa agatggtcaa tactatttag atgttaaagg cggtgcttct     720
gctggtgttt ataaagccac ttatgatgaa actcaaaga aagttaatat tgatacgact     780
gataaaactc cgttggcaac tgcggaagct acagctattc ggggaacggc cactataacc     840
cacaaccaaa ttgctgaagt aacaaaagag ggtgttgata cgaccacagt tgcggctcaa     900
cttgctgcag cagggggttac tggcgccgat aaggacaata ctagccttgt aaaactatcg     960
```

```
tttgaggata aaaacggtaa ggttattgat ggtggctatg cagtgaaaat gggcgacgat    1020
ttctatgccg ctacatatga tgagaaaaca ggtgcaatta ctgctaaaac cactacttat    1080
acagatggta ctggcgttgc tcaaactgga gctgtgaaat ttggtggcgc aaatggtaaa    1140
tctgaagttg ttactgctac cgatggtaag acttacttag caagcgacct tgacaaacat    1200
aacttcagaa caggcggtga gcttaaagag gttaatacag ataagactga aacccactg     1260 cagaaaattg atgctgcctt ggcacaggtt gatacacttc gttctgacct gggtgcggtt    1320
cagaaccgtt tcaactccgc tatcaccaac ctgggcaata ccgtaaataa cctgtcttct    1380
gcccgtagcc gtatcgaaga ttccgactac gcaaccgaag tctccaacat gtctcgcgcg    1440
cagattctgc agcaggccgg tacctccgtt ctggcgcagg cgaaccaggt tccgcaaaac    1500
gtcctctctt tactgcgtta a                                              1521

<210> SEQ ID NO 2
<211> LENGTH: 1488
<212> TYPE: DNA
<213> ORGANISM: Salmonella Paratyphi

<400> SEQUENCE: 2
atggcacaag tcattaatac aaacagcctg tcgctgttga cccagaataa cctgaacaaa      60
tcccagtccg ctctgggcac cgctatcgag cgtctgtctt ccggtctgcg tatcaacagc     120
gcgaaagacg atgcggcagg tcaggcaatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgcctg     360
aacgaaatcg accgtgtatc cggtcagact cagttcaacg gcgtgaaagt cctggcgcag     420
gacaacaccc tgaccatcca ggttggtgcc aacaacggtg aaaccattga tatcgatctg     480
aaacagatca actctcagac cctgggtctg gatacgctga atgtgcagaa aaatatgat     540 gtgaagagcg aagcggtcac gccttcggct acattaagca ctactgcact tgatggtgct     600
ggcctcaaaa ccggaaccgg ttctacaact gatactggtt caattaagga tggtaaggtt     660
tactataaca gcacctctaa aaattattat gttgaagtag aatttaccga tgcgaccgat     720
caaaccaaca aaggcggatt ctataaagtt aatgttgctg atgatggtgc agtcacaatg     780
actgcggcta ccaccaaaga ggctacaact cctacaggta ttactgaagt tactcaagtc     840
caaaaacctg tggctgctcc agctgctatc caggctcagt tgactgctgc ccatgtgacc     900
ggcgctgata ctgctgaaat ggttaagatg tcttatacgg ataaaaacgg taagactatt     960
gatggcggtt tcggtgttaa agttgggggct gatatttatg ctgcaacaaa aatataaagat    1020 ggatcgttca gcattaacac cactgaatat accgataaag acggcaacac taaaactgca    1080
ctaaaccaac tgggtggcgc agacggtaaa actgaagttg tttctatcga cggtaaaacc    1140
tacaatgcca gcaaagccgc tggtcacaac tttaaagcac agccagagct ggctgaagcg    1200
gctgctgcaa ccaccgaaaa cccgctggct aaaattgatg ccgcgctggc gcaggttgat    1260
gcgctgcgtt ctgacttggg tgcggttcag aaccgtttca actccgctat caccaacctg    1320
ggcaataccg taaataacct gtcttctgcc cgtagccgta tcgaagattc cgactacgcg    1380
accgaagttt ccaacatgtc tcgcgcgcag atcctgcagc aggccggtac ctccgttctg    1440
gcgcaggcga accaggttcc gcaaaacgtc ctctctttac tgcgttaa                 1488
```

<210> SEQ ID NO 3
<211> LENGTH: 1488
<212> TYPE: DNA
<213> ORGANISM: Salmonella paratyphi

<400> SEQUENCE: 3

```
atggcacaag tcattaatac aaacagcctg tcgctgttga cccagaataa cctgaacaaa     60
tcccagtccg ctctgggcac cgctatcgag cgtctgtctt ctggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacca actcccagtc tgacctcgac tccatccagg ctgaaatcac ccagcgcctg    360
aacgaaatcg accgtgtatc cggccagact cagttcaacg gcgtgaaagt cctggcgcag    420
gacaacaccc tgaccatcca ggttggcgcg aacgacggtg aaactatcga tatcgatctg    480
aagcagatca actctcagac cctgggtctg gatactttaa gtgtacagga tgcctatacg    540
ccaaaaggta ccgctgttac cagagatgtt accacctata aaaatggtgg tactactctt    600
acagcaccta acgcagcagc aattgatacc gctttaggta cgactggtgc ggcgggtact    660
gcggctgtga aatttaaaga cggtaactac ttcgttgagg tgaccggtac aactaaagat    720
ggtctgtatg aagcgacagt tgatgcagct ggcgcggtga caatgaccgc aaataaagca    780
acagtaactg ggctagtac agttactgaa aaccaaattg tagacgctgt tacaccgacg    840
ccagttgata cagtcgcagc agctactgca ttgaccaatg caggtgtgac aggtgcgaca    900
ggtaatacca gcttggttaa aatgtcattt gaagataaaa atggcaaagt tactgatgcg    960
ggttacgcgc ttaaagttgg aaatgattat tatgccgctg attacgatga aaaaactggt   1020
gagataaaag ctaaaactgt aaattatact gacgctactg gtgcgacaaa aaccggtgct   1080
gtgaaatttg gcggtgcgaa tggtaaaact gaagttgtga ccaccgttga tggtaatact   1140
tatcaggcta gtgatgtaaa agggcataat ttccagagtg gtggcgcttt aagcgaggct   1200
gtaaccacta aaactgaaaa cccgctggct aaaattgatg ccgcgctggc gcaagttgat   1260
gcgctgcgtt ctgacttggg tgcggttcag aaccgtttca actccgctat caccaacctg   1320
ggcaataccg taaacaacct gtctgaagcc cgtagccgta tcgaagattc cgactacgcg   1380
accgaagtct ccaacatgtc ccgcgcgcag attctgcagc aggccggtac ctccgttctg   1440
gcgcaggcga accaggttcc gcaaaacgtc ctctctttac tgcgttaa                1488
```

<210> SEQ ID NO 4
<211> LENGTH: 1521
<212> TYPE: DNA
<213> ORGANISM: Salmonella paratyphi

<400> SEQUENCE: 4

```
atggcacaag taatcaacac taacagtctg tcgctgctga cccagaataa cctgaacaaa     60
tcccagtccg cactgggcac cgctatcgag cgtctgtctt ctggtctgcg tatcaacagc    120
gcgaaagacg atgcggcagg tcaggcaatt gctaaccgtt tcaccgcgaa catcaaaggc    180
ctgactcagg cttcccgtaa cgctaacgac ggtatctcca ttgcgcagac cactgaaggc    240
gcgctgaacg aaatcaacaa caacctgcag cgtgtgcgtg aactggcggt tcagtctgct    300
aacagcacta actcccagtc tgacctcgac tctatccagg ctgaaattac ccagcgtctg    360
aacgaaatcg accgtgtatc cggccagact cagttcaacg gcgtgaaagt cctggcgcag    420
```

-continued

```
gacaacaccc tgaccatcca ggttggtgcc aacgacggtg aaactatcga tatcgatctg      480
aagcagatca actctcagac cctgggtctg gactcactga acgtgcagaa agcgtatgat      540
gtgaaagata cagcagtaac aacgaaagct tatgccaata atggtactac actggatgta     600
tcgggtcttg atgatgcagc tattaaagcg gctacggggg gtacgaatgg tacggcttct     660
gtaaccggtg gtgcggttaa atttgacgca gataataaca agtactttgt tactattggt     720
ggctttactg gtgctgatgc cgccaaaaat ggcgattatg aagttaacgt tgctactgac     780
ggtacagtaa cccttgcggc tggcgcaact aaaaccacaa tgcctgctgg tgcgacaact     840 aaaacgaag tacaggagtt aaaagataca ccggcagttg tttcagcaga tgctaaaaat      900
gccttaattg ctggcggcgt tgacgctacc gatgctaatg gcgctgagtt ggtcaaaatg     960
tcttataccg ataaaaatgg taagacaatt gaaggcggtt atgcgcttaa agctggcgat     1020
aagtattacg ccgcagatta cgatgaagcg acaggagcaa ttaaagctaa aaccacaagt    1080
tatactgctg ctgacggcac taccaaaaca gcagctaacc aactgggtgg cgtagacggt     1140
aaaaccgaag tcgttactat cgacggtaaa acctacaatg ccagcaaagc cgctggtcat    1200
gatttcaaag cacaaccaga gctggcggaa gcagccgcta aaaccaccga aaacccgctg    1260
cagaaaattg atgccgcgct ggcgcaggtg gatgcgctgc gctctgatct gggtgcggta    1320
caaaaccgtt tcaactccgc tatcaccaac ctgggcaata ccgtaaacaa cctgtctgaa    1380
gcgcgtagcc gtatcgaaga ttccgactac gcgaccgaag tttccaacat gtctcgcgcg    1440
cagattctgc agcaggccgg tacttccgtt ctggcgcagg ctaaccaggt cccgcagaac    1500
gtgctgtctc tgttacgtta a                                              1521
```

<210> SEQ ID NO 5
<211> LENGTH: 1506
<212> TYPE: DNA
<213> ORGANISM: Salmonella paratyphi

<400> SEQUENCE: 5

```
atggcacaag tcattaatac aaacagcctg tcgctgttga cccagaataa cctgaacaaa      60
tcccagtctg ctctgggtac cgctatcgag cgtctgtctt ccggtctgcg tatcaacagc     120
gcgaaagacg atgcggcagg tcaggcgatt gctaaccgtt tcaccgcgaa catcaaaggt     180
ctgactcagg cttcccgtaa cgctaacgac ggtatctcca ttgcgcagac cactgaaggc     240
gcgctgaacg aaatcaacaa caacctgcag cgtgtgcgtg aactggcggt tcagtctgct     300
aacagcacca actcccagtc tgacctcgac tccatccagg ctgaaatcac ccagcgtctg     360
aacgaaatcg accgtgtatc cggtcagact cagttcaacg gcgtgaaagt cctggcgcag     420
gacaacactc tgaccatcca ggttggtgcc aacgacggtg aaactatcga tatcgatctg     480
aagcagatca actctcagac cctgggccta gatacgctga atgtgcagaa aaatatgat    540 gtgagcgata ctgctgtagc tgcttcctat tccgactcga aacagaatat tgctgttcct    600
gataaaacag ctattactgc aaaaattggt gcagcaacca gtggtggtgc tggtataaaa    660
gcagatatta gctttaaaga tggcaagtat tacgcgactg tcagtggata cgatgatgcc    720
gcagatacag ataaaaatgg aacctatgaa gtcactgttg ccgcagatac aggagcagtt    780
acttttgcga ctacaccaac agtggttgac ttaccaactg atgcaaaagc agtttcaaaa    840
gttcaacaga tgatactga atagcagca acaaatgcga aagctgcatt aaaagctgca    900
ggagttgcag atgcagaagc tgatacagct actttagtga aaatgtctta tacagataat    960
aatggcaaag ttattgatgg tgggttcgca tttaagacct ccggtggtta ttatgcagca   1020
```

```
tctgttgata aatctggcgc agctagcttg aaagttacta gctacgttga cgctaccact    1080
ggtaccgaaa aaactgctgc gaataaatta ggtggcgcag acggtaaaac cgaagttgtt    1140
actatcgacg gtaaaaccta caatgccagc aaagccgctg gcacaacttc aaagcacag     1200 ccagagctgg cggaagcggc tgctacaacc actgaaaacc cgctgcagaa aattgatgct    1260
gctttggcgc aggtggatgc gctgcgttct gacctgggtg cggttcagaa ccgtttcaac    1320
tccgctatca ccaacctggg caataccgta ataaacctgt cttctgcccg tagccgtatc    1380
gaagattccg actacgcgac cgaagtttcc aacatgtctc gcgcgcagat tctgcagcag    1440
gccggtacct ccgttctggc gcaggcgaac caggttccgc aaaacgtcct ctctttactg    1500
cgttaa                                                               1506

<210> SEQ ID NO 6
<211> LENGTH: 1521
<212> TYPE: DNA
<213> ORGANISM: Salmonella paratyphi

<400> SEQUENCE: 6
atggcacaag taatcaacac taacagtctg tcgctgctga cccagaataa cctgaacaaa     60
tcccagtccg cactgggcac cgctatcgag cgtctgtctt ccggtctgcg tatcaacagc    120
gcgaaagacg atgcggcagg tcaggcgatt gctaaccgtt ttaccgcgaa catcaaaggt    180
ctgactcagg cttcccgtaa cgctaacgac ggtatttcta ttgcgcagac cactgaaggc    240
gcgctgaacg aaatcaacaa caacctgcag cgtgtgcgtg aactggcggt tcagtctgct    300
aacagcacta actcacagtc tgacctcgac tctatccagg ctgaaatcac ccagcgtctg    360
aacgaaatcg accgtgtatc cggtcagact cagttcaacg gcgtgaaagt cctggcgcag    420
gacaacaccc tgaccatcca ggttggtgcc aacgacggtg aaactatcga tatcgatctg    480
aagcagatca actctcagac cctgggtctg gactcactga cgtgcagaa agcgtatgat    540 gtgaaagata cagcagtaac aacgaaagct tatgccaata atggtactac actggatgta    600
tcgggtcttg atgatacagc tatcaaagcg ctataggtg gtacgactgg tacggctgct    660
gtaaccggta gtgcggttaa atttgacgca gataataaca agtactttgt tactattggt    720
ggctttactg gtgctgatgc cgccaaaaat ggcgattatg aagttaacgt tgctactgac    780
ggtacagtaa cccttgcggc tggcgcaact aaaaccacaa tgcctgctgg tgcgacaact    840
aaaacagaag tacaggagtt aaaagataca ccggcagttg tttcagcaga tgctaaaaat    900
gccttaattg ctggcggcgt tgacgctacc gatgctaatg gcgctgagtt ggtcaaaatg    960
tcttataccg ataaaaatgg taagacaatt gaaggcggtt atgcgcttaa agctggcgat    1020
aagtattacg ccgcagatta cgatgaagcg acaggagcaa ttaaagctaa aaccacagt     1080 tatactgctg ctgacggcac taccaaaaca gcagctaacc aactgggtgg cgtagacggt    1140
aaaaccgaag tcgttactat cgacggtaaa acctacaatg ccagcaaagc cgctggtcat    1200
gatttcaaag cacaaccaga gctggcggaa gcagccgcta aaccaccga aaacccgctg     1260 cagaaaattg atgccgcgct ggcgcaggtg gatgcgctgc gctctgatct gggtgcggta    1320
caaaaccgtt tcaactccgc tatccccaac ctgggcaata ccgtaaacaa cctgtctgaa    1380
gcgcgtagcc gtatcgaaga ttccgactac gcgaccgaag tttccaacat gtctcgcgcg    1440
cagattctgc agcaggccgg tacttccgtt ctggcgcagg ctaaccaggt cccgcagaac    1500
gtgctgtctc tgttacgtta a                                              1521
```

<210> SEQ ID NO 7
<211> LENGTH: 1488
<212> TYPE: DNA
<213> ORGANISM: Salmonella typhimurium

<400> SEQUENCE: 7

| | |
|---|---:|
| atggcacaag tcattaatac aaacagcctg tcgctgttga cccagaataa cctgaacaaa | 60 |
| tcccagtccg ctctgggcac cgctatcgag cgtctgtctt ccggtctgcg tatcaacagc | 120 |
| gcgaaagacg atgcggcagg tcaggcgatt gctaaccgtt ttaccgcgaa catcaaaggt | 180 |
| ctgactcagg cttcccgtaa cgctaacgac ggtatctcca ttgcgcagac cactgaaggc | 240 |
| gcgctgaacg aaatcaacaa caacctgcag cgtgtgcgtg aactggcggt tcagtctgct | 300 |
| aacagcacca actcccagtc tgacctcgac tccatccagg ctgaaatcac ccagcgcctg | 360 |
| aacgaaatcg accgtgtatc cggccagact cagttcaacg gcgtgaaagt cctggcgcag | 420 |
| gacaacaccc tgaccatcca ggttggtgcc aacgacggtg aaactatcga tatcgatctg | 480 |
| aagcagatca actctcagac cctgggtctg atacgctga atgtgcaaca aaaatataag | 540 |
| gtcagcgata cggctgcaac tgttacagga tatgccgata ctacgattgc tttagacaat | 600 |
| agtactttta aagcctcggc tactggtctt ggtggtactg accagaaaat tgatggcgat | 660 |
| ttaaaatttg atgatacgac tggaaaatat tacgccaaag ttaccgttac ggggggaact | 720 |
| ggtaaagatg gctattatga agtttccgtt gataagacga acggtgaggt gactcttgct | 780 |
| ggcggtgcga cttccccgct tacaggtgga ctacctgcga cagcaactga ggatgtgaaa | 840 |
| aatgtacaag ttgcaaatgc tgatttgaca gaggctaaag ccgcattgac agcagcaggt | 900 |
| gttaccggca cagcatctgt tgttaagatg tcttatactg ataataacgg taaaactatt | 960 |
| gatggtggtt tagcagttaa ggtaggcgat gattactatt ctgcaactca aaataaagat | 1020 |
| ggttccataa gtattaatac tacgaaatac actgcagatg acggtacatc caaaactgca | 1080 |
| ctaaacaaac tgggtggcgc agacggcaaa accgaagttg tttctattgg tggtaaaact | 1140 |
| tacgctgcaa gtaaagccga aggtcacaac tttaaagcac agcctgatct ggcggaagcg | 1200 |
| gctgctacaa ccaccgaaaa cccgctgcag aaaattgatg ctgctttggc acaggttgac | 1260 |
| acgttacgtt ctgacctggg tgcggtacag aaccgtttca actccgctat taccaacctg | 1320 |
| ggcaacaccg taaacaacct gacttctgcc cgtagccgta tcgaagattc cgactacgcg | 1380 |
| accgaagttt ccaacatgtc tcgcgcgcag attctgcagc aggccggtac ctccgttctg | 1440 |
| gcgcaggcga accaggttcc gcaaaacgtc ctctctttac tgcgttaa | 1488 |

<210> SEQ ID NO 8
<211> LENGTH: 1521
<212> TYPE: DNA
<213> ORGANISM: Salmonella typhimurium

<400> SEQUENCE: 8

| | |
|---|---:|
| atggcacaag taatcaacac taacagtctg tcgctgctga cccagaataa cctgaacaaa | 60 |
| tcccagtccg cactgggcac cgctatcgag cgtctgtctt ctggtctgcg tatcaacagc | 120 |
| gcgaaagacg atgcggcagg tcaggcgatt gctaaccgtt tcaccgcgaa catcaaaggt | 180 |
| ctgactcagg cttcccgtaa cgctaacgac ggtatctcca ttgcgcagac cactgaaggc | 240 |
| gcgctgaacg aaatcaacaa caacctgcag cgtgtgcgtg aactggcggt tcagtctgct | 300 |
| aacagcacca actcccagtc tgacctcgac tccatccagg ctgaaatcac ccagcgcctg | 360 |
| aacgaaatcg accgtgtatc cggccagact cagttcaacg gcgtgaaagt cctggcgcag | 420 |

```
gacaacaccc tgaccatcca ggttggcgcc aacgacggtg aaactatcga tatcgatctg      480
aagcagatca actctcagac cctgggtctg gactcactga acgtgcagaa agcgtatgat      540
gtgaaagata cagcagtaac aacgaaagct tatgccaata atggtactac actggatgta      600
tcgggtcttg atgatgcagc tattaaagcg gctacgggtg gtacgaatgg tacggcttct      660
gtaaccggtg gtgcggttaa atttgacgca gataataaca agtactttgt tactattggt      720
ggctttactg gtgctgatgc cgccaaaaat ggcgattatg aagttaacgt tgctactgac      780
ggtacagtaa cccttgcggc tggcgcaact aaaaccacaa tgcctgctgg tgcgacaact      840
aaaacagaag tacaggagtt aaaagataca ccggcagttg tttcagcaga tgctaaaaat      900
gccttaattg ctggcggcgt tgacgctacc gatgctaatg gcgctgagtt ggtcaaaatg      960
tcttataccg ataaaaatgg taagacaatt gaaggcggtt atgcgcttaa agctggcgat      1020
aagtattacg ccgcagatta cgatgaagcg acaggagcaa ttaaagctaa aactacaagt      1080
tatactgctg ctgacggcac taccaaaaca gcggctaacc aactgggtgg cgtagacggt      1140
aaaaccgaag tcgttactat cgacggtaaa acctacaatg ccagcaaagc cgctggtcat      1200
gatttcaaag cacaaccaga gctggcggaa gcagccgcta aaaccaccga aaacccgctg      1260
cagaaaattg atgccgcgct ggcgcaggtg gatgcgctgc gctctgatct gggtgcggta      1320
caaaaccgtt tcaactctgc tatcaccaac ctgggcaata ccgtaaacaa tctgtctgaa      1380
gcgcgtagcc gtatcgaaga ttccgactac gcgaccgaag tttccaacat gtctcgcgcg      1440
cagattctgc agcaggccgg tacttccgtt ctggcgcagg ctaaccaggt cccgcagaac      1500
gtgctgtctc tgttacgtta a                                               1521
```

<210> SEQ ID NO 9
<211> LENGTH: 1518
<212> TYPE: DNA
<213> ORGANISM: Salmonella enteritidis

<400> SEQUENCE: 9

```
atggcacaag tcattaatac aaacagcctg tcgctgttga cccagaataa cctgaacaaa      60
tctcagtcct cactgagttc cgctattgag cgtctgtcct ctggtctgcg tatcaacagc      120
gcgaaagacg atgcggcagg ccaggcgatt gctaaccgct tcacttctaa tatcaaaggt      180
ctgactcagg cttcccgtaa cgctaacgac ggcatttcta ttgcgcagac cactgaaggt      240
gcgctgaatg aaatcaacaa caacctgcag cgtgtgcgtg agttgtctgt tcaggccact      300
aacgggacta ctctgattc cgatctgaaa tctatccagg atgaaattca gcaacgtctg      360
gaagaaatcg atcgcgtttc taatcagact caatttaacg gtgttaaagt cctgtctcag      420
gacaaccaga tgaaaatcca ggttggtgct aacgatggtg aaaccattac catcgatctg      480
caaaaaattg atgtgaaaag ccttggcctt gatgggttca atgttaatgg ccaaaagaa      540 gcgacagtgg gtgatctgaa atccagcttc aagaatgtta cggttacga cacctatgca      600 gcgggtgccg ataaatatcg tgtagatatt aattccggtg ctgtagtgac tgatgcagca      660
gcaccggata agtatatgt aaatgcagca aacggtcagt taacaactga cgatgcggaa      720
aataacactg cggttgatct cttaagacc actaaatcta ctgctggtac cgctgaagcc      780
aaagcgatag ctggtgccat taaaggtggt aaggaaggag atacctttga ttataaaggc      840
gtgactttta ctattgatac aaaaaactggt gatgacggta atggtaaggt ttctactacc      900
atcaatggtg aaaaagttac gttaactgtc gctgatattg ccactggcgc gacggatgtt      960
```

```
aatgctgcta ccttacaatc aagcaaaaat gtttatacat ctgtagtgaa cggtcagttt    1020
acttttgatg ataaaaccaa aaacgagagt gcgaaacttt ctgatttgga agcaaacaat    1080
gctgttaagg gcgaaagtaa aattacagta aatggggctg aatatactgc taacgccacg    1140
ggtgataaga tcaccttagc tggcaaaacc atgtttattg ataaaacagc ttctggcgta    1200
agtacattaa tcaatgaaga cgctgccgca gccaagaaaa gtaccgctaa cccactggct    1260
tcaattgatt ctgcattgtc aaagtggac gcagttcgtt cttctctggg ggcaattcaa    1320
aaccgttttg attcagccat taccaacctt ggcaatacgg taaccaatct gaactccgcg    1380
cgtagccgta tcgaagatgc tgactatgca acggaagttt ctaatatgtc taaagcgcag    1440
attctgcagc aggctggtac ttccgttctg gcgcaggcta accaggttcc gcaaaacgtc    1500
ctctctttac tgcgttaa                                                  1518

<210> SEQ ID NO 10
<211> LENGTH: 540
<212> TYPE: DNA
<213> ORGANISM: Salmonella typhi

<400> SEQUENCE: 10
atgaggtttc atcatttctg gcctccgaat gatatctatt tcggggttgg agctgctggc     60
attattgaag aagtgtcact gataacaaat gacagaaatt atttgtttgt gaacctaaat    120
cgctacagcc tgttaaatgc cctgaatttt tcacgcgaa tgagtgatat taataaaata    180
atcgttatca tttcaagttc gcgactaatg ccccttgcac gttttggtt gacagagtgc    240 aaaaatgtta ttgctgtttt cgatgcggca acatcagtcc aggatattat cagaaatgtc    300
agtcaacacc aaagtggtga aaagatcttg acggagcaga gagattatcg tttcagaatt    360
aaccgtaagg atatagtaaa gatgaaatat ttcctttcgg aaagtggtat ggaagagctt    420
caggatagat ttatgaactc atcatcgact atgtatcgct ggagaaaaga attggcagta    480
aaatttggag tacgtgagcc gcgctatctg ttattgccgg attcagttac tttactgtaa    540

<210> SEQ ID NO 11
<211> LENGTH: 1137
<212> TYPE: DNA
<213> ORGANISM: Salmonella typhimurium

<400> SEQUENCE: 11
atgccatctc ttaatgtaaa acaagaaaaa aatcagtcat ttgcaggtta ttcactgccg     60
cccgccaaca gtcatgaaat cgatttgttt agccttatag aggtgttatg gcaggcgaaa    120
cgtcgtattc ttgctaccgt tttcgccttt gcgtgcgtgg ggttgcttct gtcctttctg    180
ctgccgcaaa aatggaccag ccaggcgatt gtcacaccgg cggagtcggt acagtggcag    240
gggctggaga gaacgttgac cgcgctgcgc gtgttggata tggaggtaag cgttgatcgg    300
ggcagcgtat ttaatctgtt tattaaaaag tttagctcgc cctcgctgct ggaagaatat    360
cttcgttctt ctccgtatgt catggatcaa ttaaaaggcg cgcaaataga cgagcaggat    420
cttcaccggg cgattgtcct gctgagcgaa aaaatgaaag cggtggacag taatgtcggc    480
aagaaaaatg aaacgtcgtt attcacgtcg tggacattga gttttaccgc gccgacgcgg    540
gaagaagcgc aaaaagtgct ggctggctat attcagtaca tctccgatat cgtcgtgaaa    600
gagacgctgg aaaatattcg taaccagctg gaaatcaaaa cccgctatga gcaggaaaag    660
ctggcgatgg atcgggtgcg tctcaaaaat cagcttgatg ccaatattca acgtcttcat    720
tattcgctgg aaatcgccaa cgccgccggt attaagagac cggtttacag caatggtcag    780
```

| | | |
|---|---|---|
| gcggtaaaag atgatccgga ttttctatt tctctcggcg cggatggtat tcccgcaaa | 840 | |
| ctggaaattg aaaaggggt aacggacgtg gccgagatcg acggtgattt gcgtaaccgt | 900 | |
| caataccatg ttgaacaact ggcggcaatg aatgtgagtg acgtgaagtt taccccgttt | 960 | |
| aaatatcaac tgtcgccgtc tctgccagtg aaaaagatg gcccgggtaa agccatcatt | 1020 | |
| attatcctgg cggcgttgat tggcggtatg atggcctgcg gcggcgtatt actgcgtcac | 1080 | |
| gcgatggtct cgcgtaaaat ggaaaacgcg ctggcgatag atgaacggtt agtctga | 1137 | |

<210> SEQ ID NO 12
<211> LENGTH: 1017
<212> TYPE: DNA
<213> ORGANISM: Salmonella typhi

<400> SEQUENCE: 12

| | | |
|---|---|---|
| atgaagcttt taattaccgg tggatgtggc ttccttggga gtaatcttgc ctcctttgct | 60 | |
| ttaagtcaag ggattgattt aattgtattc gataatctat cacgtaaagg tgcaacagat | 120 | |
| aatttacatt ggttatcctc cttaggaaac tttgagtttg tacatggtga tattcgcaac | 180 | |
| aaaaatgatg ttacaagatt aataactaag tatatgcctg atagctgttt tcatcttgca | 240 | |
| ggtcaagtgg caatgactac atctattgac aatccttgta tggattttga aattaatgta | 300 | |
| ggtggaactt taaatttact tgaggcagta cggcagtata attcaaattg taatataatt | 360 | |
| tattcatcaa caaataaagt atacggcgat cttgagcaat ataaatacaa tgaaacagaa | 420 | |
| actagataca cttgtgtaga taagcctaat ggatatgatg agagcacaca attagatttc | 480 | |
| cactcaccat atggttgttc aaaaggtgct gcagaccaat acatgcttga ttatgcaagg | 540 | |
| atttttggtt tgaatacagt ggtgttcagg cattcatcaa tgtatggtgg agacagttt | 600 | |
| gctacttatg atcaaggctg gtaggttgg ttttgtcaaa aagcggttga aattaaaaat | 660 | |
| ggtattaata aacccttcac tatttctggt aatggtaagc aagttaggga tgttttgcat | 720 | |
| gctgaagata tgatttcgtt atatttcact gccttggcaa atgtatcaaa aattaggggg | 780 | |
| aacgctttta atattggtgg taccattgtc aacagcctat cattacttga attattcaaa | 840 | |
| ttgcttgaag attattgcaa catagatatg aggttcacta atttacctgt aagggaaagt | 900 | |
| gatcagcgtg ttttgttgc agatattaaa aaaatcacta tgcaattga ctggagcccg | 960 | |
| aaagtctcgg caaagatgg tgtccagaaa atgtatgatt ggactagttc tatatga | 1017 | |

<210> SEQ ID NO 13
<211> LENGTH: 666
<212> TYPE: DNA
<213> ORGANISM: Escherichia coli

<400> SEQUENCE: 13

| | | |
|---|---|---|
| atgaatttgt atggtatttt tggtgctgga agttatggta gagaaacaat acccattcta | 60 | |
| aatcaacaaa taaagcaaga atgtggttct gactatgctc tggtttttgt ggatgatgtt | 120 | |
| ttggcaggaa agaaagttaa tggttttgaa gtgctttcaa ccaactgctt tctaaaagcc | 180 | |
| ccttatttaa aaaagtattt taatgttgct attgctaatg ataagatacg acagagagtg | 240 | |
| tctgagtcaa tattattaca cggggttgaa ccaataacta taaaacatcc aaatagcgtt | 300 | |
| gtttatgatc atactatgat aggtagtggc gctattattt ctcccttgt tacaatatct | 360 | |
| actaatactc atagggag gttttttcat gcaaacatat actcatacgt tgcacatgat | 420 | |
| tgtcaaatag gagactatgt tacatttgct cctggggcta atgtaatgg atatgttgtt | 480 | |

| | |
|---|---|
| attgaagaca atgcatatat aggctcgggt gcagtaatta agcagggtgt tcctaatcgc | 540 |
| ccacttatta ttggcgcggg agccattata ggtatggggg ctgttgtcac taaaagtgtt | 600 |
| cctgccggta taactgtgtg cggaaatcca gcaagagaaa tgaaaagatc gccaacatct | 660 |
| atttaa | 666 |

<210> SEQ ID NO 14
<211> LENGTH: 840
<212> TYPE: DNA
<213> ORGANISM: Salmonella typhi

<400> SEQUENCE: 14

| | |
|---|---|
| atgaaaattc taataatggg agcgtttggg ttccttggat cacgacttac atcctacttc | 60 |
| gaaagtcgac atactgtgat tggcttagca aggaagagga acaatgaagc taccataaat | 120 |
| aatattattt acacgacaga aaataattgg atcgaaaaaa tactagaatt tgaaccgaat | 180 |
| attattatta acactattgc ttgctatgga agacataacg aacctgcaac agctttaata | 240 |
| gaaagcaata ttcttatgcc tatcagagta ttagaatcta tctcatcact tgatgcagta | 300 |
| ttcataaatt gtggaacatc actgccacca aatacgagtt tatatgcata tactaaacaa | 360 |
| aaagcaaatg aactcgccgc cgccattata gataaagttt gcggtaaata tatagagtta | 420 |
| aaattggagc atttctatgg agcttttgat ggagacgata agtttaccag tatggttatt | 480 |
| agacgttgtt taagtaacca gccagtaaag ttaacatctg gtttgcaaca gagagatttc | 540 |
| ttgtatataa aagatctact aacagcgttc gattgtatta aagtaatgt taataatttc | 600 |
| cccaaatttc atagtattga agttggtagt ggagaggcga tatcaattcg tgaatatgta | 660 |
| gatactgtta aaaatatcac aaaaagcaat tctataattg aatttggcgt ggtcaaagaa | 720 |
| agagtaaatg aattgatgta tagttgtgct gatatagcag aacttgaaaa ataggatgg | 780 |
| aaaagagagt tctctcttgt tgatgcatta actgaaataa ttgaagagga agggaaatga | 840 |

<210> SEQ ID NO 15
<211> LENGTH: 900
<212> TYPE: DNA
<213> ORGANISM: Salmonella typhimurium

<400> SEQUENCE: 15

| | |
|---|---|
| atgaccttt tgaaagaata tgtaattgtc agtggggctt ccggctttat tggtaagcat | 60 |
| ttactcgaag cgctaaaaaa atcggggatt tcagttgtcg caatcactcg agatgtaata | 120 |
| aaaaataata gtaatgcatt agctaatgtt agatggtgca gttgggataa tatcgaatta | 180 |
| ttagtcgagg agttatcaat tgattctgca ttaattggta tcattcattt ggcaacagaa | 240 |
| tatgggcata aacatcatc tctcataaat attgaagatg caaatgttat aaaaccatta | 300 |
| aagcttcttg atttggcaat aaaatatcgg gcggatatct ttttaaatac agatagtttt | 360 |
| tttgccaaga aagattttaa ttatcaacat atgcggcctt atataattac taaaagacac | 420 |
| tttgatgaaa ttgggcatta ttatgctaat atgcatgaca tttcatttgt aaacatgcga | 480 |
| ttagagcatg tatatgggcc tggggatggt gaaaataaat ttattccata cattatcgac | 540 |
| tgcttaaata aaaaacagag ttgcgtgaaa tgtacaacag cgaacagat aagagacttt | 600 |
| atttttgtag atgatgtggt aaatgcttat ttaactatat agaaaatag aaaagaagta | 660 |
| ccttcatata ctgagtatca agttggaact ggtgctgggg taagtttgaa agattttctg | 720 |
| gtttatttgc aaaatactat gatgccaggt tcatcgagta tatttgaatt tggtgcgata | 780 |
| gagcaaagag ataatgaaat aatgttctct gtagcaaata taaaaatttt aaaagcaatg | 840 |

```
ggctggaaac caaatttcga ttataaaaaa ggaattgaag aactactgaa acggttatga    900
```

<210> SEQ ID NO 16
<211> LENGTH: 466
<212> TYPE: DNA
<213> ORGANISM: Salmonella typhimurium

<400> SEQUENCE: 16

```
tattgccatc gcggatgtcg cctgtcttat ctaccatcat aaacatcatt tgcctatggc     60
tcacgacagt ataggcaatg ccgttttttta tattgctaat tgtttcgcca atcaacgcaa   120
aagtatggcg attgctaaag ccgtctccct gggcggtaga ttagccttaa ccgcgacggt   180
aatgactcat tcatactgga gtggtagttt gggactacag cctcatttat tagagcgtct   240
taatgatatt acctatggac taatgagttt tactcgcttc ggtatggatg ggatggcaat   300
gaccggtatg caggtcagca gcccattata tcgtttgctg gctcaggtaa cgccagaaca   360
acgtgcgccg gagtaatcgt tttcaggtat ataccggatg ttcattgctt tctaaattttt   420
gctatgttgc cagtatcctt acgatgtatt tattttaagg aaaagc                  466
```

<210> SEQ ID NO 17
<211> LENGTH: 1231
<212> TYPE: DNA
<213> ORGANISM: Escherichia coli

<400> SEQUENCE: 17

```
ttatgacaac ttgacggcta catcattcac tttttcttca caaccggcac ggaactcgct    60
cgggctggcc ccggtgcatt ttttaaatac ccgcgagaaa tagagttgat cgtcaaaacc   120
aacattgcga ccgacggtgg cgataggcat ccgggtggtg ctcaaaagca gcttcgcctg   180
gctgatacgt tggtcctcgc gccagcttaa gacgctaatc cctaactgct ggcggaaaag   240
atgtgacaga cgcgacggcg acaagcaaac atgctgtgcg acgctggcga tatcaaaatt   300
gctgtctgcc aggtgatcgc tgatgtactg acaagcctcg cgtacccgat tatccatcgg   360
tggatggagc gactcgttaa tcgcttccat gcgccgcagt aacaattgct caagcagatt   420
tatcgccagc agctccgaat agcgcccttc cccttgcccg gcgttaatga tttgcccaaa   480
caggtcgctg aaatgcggct ggtgcgcttc atccgggcga agaacccccg tattggcaaa   540
tattgacggc cagttaagcc attcatgcca gtaggcgcgc ggacgaaagt aaacccactg   600
gtgataccat tcgcgagcct ccggatgacg accgtagtga tgaatctctc ctggcgggaa   660
cagcaaaata tcacccggtc ggcaaacaaa ttctcgtccc tgattttttca ccaccccctg   720
accgcgaatg gtgagattga aatataacc tttcattccc agcggtcggt cgataaaaaa    780
atcgagataa ccgttggcct caatcggcgt taaacccgcc accagatggg cattaaacga   840
gtatcccggc agcaggggat cattttgcgc ttcagccata cttttcatac tcccgccatt   900
cagagaagaa accaattgtc catattgcat cagacattgc cgtcactgcg tcttttactg   960
gctcttctcg ctaaccaaac cggtaacccc gcttattaaa agcattctgt aacaaagcgg  1020
gaccaaagcc atgacaaaaa cgcgtaacaa aagtgtctat aatcacggca gaaaagtcca  1080
cattgattat ttgcacggcg tcacactttg ctatgccata gcatttttat ccataagatt  1140
agcggatcct acctgacgct ttttatcgca actctctact gtttctccat accegttttt  1200
ttgggctagc gaattgagga ggagatatac a                                 1231
```

<210> SEQ ID NO 18

-continued

<211> LENGTH: 1032
<212> TYPE: DNA
<213> ORGANISM: Salmonella Paratyphi

<400> SEQUENCE: 18
ttgaagagga agagaaatga agctttaatt accggtggat gtggcttcct tgggagtaat 60
cttgcctcct ttgctttaag tcaagggatt gatttaattg tattcgataa tctatcacgt 120
aaaggtgcaa cagataattt acattggtta tcctccttag gaaactttga gtttgtacat 180
ggtgatattc gcaacaaaaa tgatgttaca agattaataa ctaagtatat gcctgatagc 240
tgttttcatc ttgcaggtca agtggcaatg actacatcta ttgacaatcc ttgtatggat 300
tttgaaatta atgtaggtgg aactttaaat ttacttgagg cagtacggca gtataattca 360
aattgtaata taatttattc atcaacaaat aaagtatacg gcgatcttga gcaatataaa 420
tacaatgaaa cagaaactag atacacttgt gtagataagc ctaatggata tgatgagagc 480
acacaattag atttccactc accatatggt tgttcaaaag gtgctgcaga ccaatacatg 540
cttgattatg caaggatttt tggtttgaat acagtggtgt tcaggcattc atcaatgtat 600
ggtgggagac agtttgctac ttatgatcaa ggctgggtag gttggttttg tcaaaaagcg 660
gttgaaatta aaaatggtat taataaaccc ttcactattt ctggtaatgg taagcaagtt 720
agggatgttt tgcatgctga agatatgatt tcgttatatt tcactgcctt ggcaaatgta 780
tcaaaaatta gggggaacgc ttttaatatt ggtggtacca ttgtcaacag cctatcatta 840
cttgaattat tcaaattgct tgaagattat tgcaacatag atatgaggtt cactaattta 900
cctgtaaggg aaagtgatca gcgtgttttt gttgcagata ttaaaaaaat cactaatgca 960
attgactgga gcccgaaagt ctcggcaaaa gatggtgtcc agaaaatgta tgattggact 1020
agttctatat ga 1032

<210> SEQ ID NO 19
<211> LENGTH: 1843
<212> TYPE: DNA
<213> ORGANISM: Artificial Sequence
<220> FEATURE:
<223> OTHER INFORMATION: Salmonella typhi rfbE locus with a partial deletion of rfbE

<400> SEQUENCE: 19
tcacgactta catcctactt cgaaagtcga catactgtga ttggcttagc aaggaagagg 60
aacaatgaag ctaccataaa taatattatt tacacgacag aaaataattg gatcgaaaaa 120
atactagaat ttgaaccgaa tattattatt aacactattg cttgctatgg aagacataac 180
gaacctgcaa cagctttaat agaaagcaat attcttatgc ctatcagagt attagaatct 240
atctcatcac ttgatgcagt attcataaat tgtggaacat cactgccacc aaatacgagt 300
ttatatgcat atactaaaca aaaagcaaat gaactcgccg ccgccattat agataaagtt 360
tgcggtaaat atatagagtt aaaattggag catttctatg gagcttttga tggagacgat 420
aagtttacca gtatggttat tagacgttgt ttaagtaacc agccagtaaa gttaacatct 480
ggtttgcaac agagagattt cttgtatata aaagatctac taacagcgtt cgattgtatt 540
ataagtaatg ttaataattt ccccaaattt catagtattg aagttggtag tggagaggcg 600
atatcaattc gtgaatatgt agatactgtt aaaaatatca caaaaagcaa ttctataatt 660
gaatttggcg tggtcaaaga aagagtaaat gaattgatgt atagttgtgc tgatatagca 720
gaacttgaaa aaataggatg gaaaagagag ttctctcttg ttgatgcatt aactgaaata 780

```
attgaagagg aagggaaatg aaaagcttgg taccgagctc ggatccacta gtaacggccg      840
ccagtgtgct ggaattcgcc ctttaagcgg ccgcatttaa cataatatac attatgcgca      900
ccgcggccgc ggaaagggcg aattctgcag atatccatca cactggcggc cgctcgagca      960
tgcatctaga gtgaggaaac tgaggttggt tagaattcca agacatctta ttattgccgc     1020
ttcctcttgg ctttcaaaga taataattgc cggtgttcag ttagtaagtg ttaaatttct     1080
tttagaaatt cttggcgaag aatcatacgc tgtatttact cttttaactg gattattggt     1140
ctggtttagc attgcagata ttgggattgg tagtagtcta caaaattata tatctgagtt     1200
gaaagctgat agaaaatcat atgatgcata tatcaaggcc gcagttcata ttctattcgc     1260
atccttaatc attttaagct ctacattatt cttcttatca gataaattat cgtcactata     1320
tcttacttca tttagcgatg aattgaaaaa caactcagga agttattttt ttatagcaag     1380
tatattattt atattcatcg gcgttgggag tgtggtctat aaaatattat ttgcggaact     1440
gttagggtgg aaagctaata taattaatgc attatcttat cttttaggtt ttttagatgt     1500
agttgcgatc cattatttaa tgccagattc gagtattacc ttcgctttag tagcattgta     1560
tgctccggta gcaatactgc ccattatata tatcgtttt cggtatatat atgttcttaa     1620
agcgaaagta aactttaaca cctataaatt attactatca cgttcatcag ggtttctgat     1680
tttttcgtcc ttatcgataa tagttttaca aactgattat attgtgatgt ctcagaaatt     1740
atctgctgca gatattataa aatatactgt aacgatgaaa atatttggtt taatgttttt     1800
tatttatact gcggtattac aagcattatg gccagtatgt gct                       1843
```

<210> SEQ ID NO 20
<211> LENGTH: 3142
<212> TYPE: DNA
<213> ORGANISM: Artificial Sequence
<220> FEATURE:
<223> OTHER INFORMATION: Salmonella typhi rfbE locus with rfbE disrupted by wbdR

<400> SEQUENCE: 20

```
aggcttgact acagagcatt tagattatgt agttagcaag tttgaagagt tctttggttt     60
gaatttctaa ttttgagggg gggggattcc cctctatgat ttcatgaaaa ttctaataat    120
gggagcgttt gggttccttg gatcacgact tacatcctac ttcgaaagtc gacatactgt    180
gattggctta gcaaggaaga ggaacaatga agctaccata aataatatta tttacacgac    240
agaaaataat tggatcgaaa aaatactaga atttgaaccg aatattatta ttaacactat    300
tgcttgctat ggaagacata acgaacctgc aacagcttta atagaaagca atattcttat    360
gcctatcaga gtattagaat ctatctcatc acttgatgca gtattcataa attgtggaac    420
atcactgcca ccaaatacga gtttatatgc atatactaaa caaaaagcaa atgaactcgc    480
cgccgccatt atagataaag tttgcggtaa atatatagag ttaaaattgg agcatttcta    540
tggagctttt gatggagacg ataagtttac cagtatggtt attagacgtt gtttaagtaa    600
ccagccagta aagttaacat ctggtttgca acagagagat ttcttgtata taaaagatct    660
actaacagcg ttcgattgta ttataagtaa tgttaataat ttccccaaat ttcatagtat    720
tgaagttggt agtggagagg cgatatcaat tcgtgaatat gtagatactg ttaaaaatat    780
cacaaaaagc aattctataa ttgaatttgg cgtggtcaaa gaaagagtaa atgaattgat    840
gtatagttgt gctgatatag cagaacttga aaaaatagga tggaaaagag agttctctct    900
tgttgatgca ttaactgaaa taattgaaga ggaagggaaa tgaatttgta tggtattttt    960
```

```
ggtgctggaa gttatggtag agaaacaata cccattctaa atcaacaaat aaagcaagaa    1020
tgtggttctg actatgctct ggttttgtg gatgatgttt tggcaggaaa gaaagttaat     1080
ggttttgaag tgctttcaac caactgcttt ctaaaagccc cttatttaaa aaagtatttt    1140
aatgttgcta ttgctaatga taagatacga cagagagtgt ctgagtcaat attattacac    1200
ggggttgaac caataactat aaaacatcca aatagcgttg tttatgatca tactatgata    1260
ggtagtggcg ctattatttc tcccttgtt acaatatcta ctaatactca tatagggagg     1320
ttttttcatg caaacatata ctcatacgtt gcacatgatt gtcaaatagg agactatgtt    1380
acatttgctc ctggggctaa atgtaatgga tatgttgtta ttgaagacaa tgcatatata    1440
ggctcgggtg cagtaattaa gcagggtgtt cctaatcgcc cacttattat tggcgcggga    1500
gccattatag gtatggggc tgttgtcact aaaagtgttc ctgccggtat aactgtgtgc     1560
ggaaatccag caagagaaat gaaaagatcg ccaacatcta tttaatgcgg ccgcatttaa    1620
cataatatac attatgcgca ccgcggccgc cagtgtgagg atcctgtttc tgcccgcgaa    1680
agcgggcata attaaagaat gaaatatttt ttataattaa aagatgaagc tgacgtgagg    1740
aaactgaggt tggttagaat tccaagacat cttattattg ccgcttcctc ttggctttca    1800
aagataataa ttgccggtgt tcagttagta agtgttaaat ttcttttaga aattcttggc    1860
gaagaatcat acgctgtatt tactcttta actggattat tggtctggtt tagcattgca     1920
gatattggga ttggtagtag tctacaaaat tatatatctg agttgaaagc tgatagaaaa    1980
tcatatgatg catatatcaa ggccgcagtt catattctat tcgcatcctt aatcattta     2040 agctctacat tattcttctt atcagataaa ttatcgtcac tatatcttac ttcatttagc    2100
gatgaattga aaaacaactc aggaagttat tttttatag caagtatatt atttatattc     2160
atcggcgttg ggagtgtggt ctataaaata ttatttgcgg aactgttagg gtggaaagct    2220
aatataatta atgcattatc ttatctttta ggtttttag atgtagttgc gatccattat     2280
ttaatgccag attcgagtat taccttcgct ttagtagcat tgtatgctcc ggtagcaata    2340
ctgcccatta tatatatc gtttcggtat atatatgttc ttaaagcgaa agtaaacttt      2400
aacacctata aattattact atcacgttca tcagggtttc tgattttttc gtccttatcg    2460
ataatagttt tacaaactga ttatattgtg atgtctcaga aattatctgc tgcagatatt    2520
ataaaatata ctgtaacgat gaaaatattt ggttaatgt ttttattta tactgcggta     2580 ttacaagcat tatggccagt atgtgctgaa ttacgagtga aaatgcagtg gagaaagctg    2640
catagaatca ttttcctaaa tattattggt ggggtatttt ttattggtct tggtacgtta    2700
tttatttatg ttttaaagga ttatatctat agcataattg ctaacggtat agattataat    2760
attagtgggg ttgttttgt tttactggct gtgtatttta gtataagagt ttggtgtgat     2820
acatttgcta tgttacttca aagtatgaac caattaaaaa ttctttggct catagttccg    2880
tgtcaggcat taattggtgg tgtgactcaa tggtattttg cagagcatta tggaatagtt    2940 ggtatttat acggactaat tttatcgttc tcgctaactg tttttgggg attgccagtg      3000 tattatatgt ataagagtaa aaggctagca taatatgaag gtatcatttt gtatcccaac    3060
gtataatcga gtaaaattca ttgaagacct tcttgaaagt attaataatc aatcttctca    3120
ctccttaatt gtagaagtat gt                                             3142
```

<210> SEQ ID NO 21
<211> LENGTH: 1137
<212> TYPE: DNA
<213> ORGANISM: Artificial Sequence
<220> FEATURE:
<223> OTHER INFORMATION: Salmonella typhi fepE pseudogene

<400> SEQUENCE: 21

```
atgccatctc ttaatgtaaa acaagagaaa aatcagtcat ttgcaggtta ctcactgccg      60
cccgccaaca gtcatgaaat cgatttgttt agccttatag aggtgttatg gcaggcgaaa     120
cgtcgtattc ttgctaccgt tttcgccttt gcgtgcgtgg ggttgcttct gtcctttctg     180
ctgccgcaaa aatggaccag ccaggcgatt gtcacaccgg cggagtcggt acagtagcag     240
gggctggaga gaacgttgac cgcgctgcgc gtgttggata tggaggtaag cgttgatcgg     300
gccagcgtat ttaatctgtt tattaaaaag tttagctcgc cctcgctgct ggaagaatat     360
cttcgttctt ctccgtatgt catggatcaa ttaaaaggcg cgcaaataga cgagcaggat     420
cttcaccggg cgattgtcgt gctgagcgaa aaaatgaaag cggtggacag caatgccggc     480
aagaaaaatg aaacgtcgtt attcacgtcg tggacgctga gttttaccgc gccgacgcgg     540
gaagaagcgc aaaagtgtt ggctggctat attcagtaca tctccgatat cgtcgtgaaa     600
gagacgctgg aaaatattcg taaccagctg gaaatcaaaa cccgctacga gcaggaaaag     660
ctggcgatga tcgggtgcg tctcaaaaat cagcttgatg ccaatattca acgtcttcat     720
tattcgctgg aaatcgccaa cgccgctggc attaagagac cggtttacag taatggtcag     780
gcggtaaaag atgatccgga ttttctatt tccctcggcg cggatggtat ttccgcaaa     840
ctggaaattg aaaaggggt aacggacgtg gccgagatcg acggtgattt gcgtaaccgt     900
caatactatg ttgaacaact ggcggcaatg aatgtgagcg acgtgaagtt taccccgttt     960
aaatatcaac tgtcgccgtc tctgccagtg aaaaaagatg gcccgggtaa agcgatcatt    1020
attatcctgg cggcgttgat tggcggtatg atggcctgcg cggcgtatt actgcgtcac    1080
gcgatggtct cgcgtaaaat ggaaaacgcg ctggcgatag atgaacggtt agtctga      1137
```

<210> SEQ ID NO 22
<211> LENGTH: 3394
<212> TYPE: DNA
<213> ORGANISM: Salmonella typhi

<400> SEQUENCE: 22

```
actgcactga cggtggcggt tgaaacgctg aaggcataaa gatcttcact ctcccggccg      60
atgtcctgat aactcatctc cagcgcaaac agtcgaatga tattgcgctc gatctcgtcg     120
tacaggggt ctgaagcttc ttcaccaatt atggctcaaa agtgccgtta cgattgcgcg     180
gagttgccag ttcaaaactg cctgttgggg ctttaatggc tttttgccgg aaccattttt     240
acggtttgcc tcaacatcct gagccagatg ggaatcaagt tcagcagaca gggtagagtc     300
ggttaaatac ttgattaatg gcgttaagat gccatctttg cccgtaatg cctggccgga     360
cctgaagggc tttaagtgct ttgtcgaaat cgaagggatg ggacatgtgc cattctttt     420
tattttatgt tactaaaatt atacagaatt tttaacgctc cccctctccc cagcacttcc     480
acccttcaa gtacctctct ctgaaaaaac atgcaaagcc ttgtaagacg atgtaaagct     540
ttacatgtcc cgttttttatt ccaagacgct tggcaatcag caataccaat tgatcgataa     600
catcgatcaa tatattaaaa ctcaatagct taaaactatt aaaatacaa ttattgatcg     660
cttatatcga tcaaaccaat ttgtagtgct acactccaga cctttctgaa tcggctaatt     720
ttcataatgt tgaagttatt cgctaagtac acatcgatcg gtgttcttaa cacgctcatt     780
cattggggag tatttgcttt ctgtatgtat gggatgcata cgcatcaggc gctgacgaac     840
```

```
ttttccgatt tgttatcgc tgtatcgttc agcttctatg ctaatgcgcg cttcaccttt      900
aatgccagca ctactgcaat tctctacatg atgtatatgg gattcatggg aacactgagc      960
gctgttgttg gatggatggc tgaccaatgt tctttgccac cattggttac cctcatcact     1020
ttctcggcaa ttagcctggt atgcggcttt atctattcca gattcattat cttcagggat     1080
aaaaatgaaa atctctcttg tcgtcctggt ttttaacgaa gaagacacga taccgatttt     1140
ctatagaacg gtacatgagt ttaatgaact tgaaaaatat aaagttgaga ttatttttat     1200
taatgacgga agtaaagatg tgacggagtc aataattaaa ataatagccg tatctgatcc     1260
actcgtcatt ccgttttcgt ttacacgaaa cttcgggaat gatgcaagat gcacaaccat     1320
tttattaatc tttttttaaa ttgaggtaat ttaagttgga acacttaaaa tacagacctg     1380
atatagatgg attacgcgca atagcggttt tatctgtggt aatattccat tatttcccat     1440
cattattgcc gggtgggttt gttggagtag atatattctt tgtgatatct ggatacctta     1500
taacatcaat aatattaaaa tctgcatcaa acaaatcatt ttcataccct gatttctata     1560
aaaggagagt gcttagaata tttccagcat tatccatagt tcttgtatca tgtcttattg     1620
ttggttggat ttatttattc caggatgatt acaaattact tggtaagcat gttttagtg      1680 gctcattctt tatatcaaac tttactcttt ggagtgagtc tggctatttt gattcaaaat     1740 catacctaa accttactac catttgtggt cgctgggaat tgaagagcaa ttttatataa     1800
tatggccagt agtatattg ctatgcttta gaagcaaaaa ccataacaga aacatagtat      1860
tatcatgcgc aactatattt ataattagct atgcgattag catttttaca atggcatctg     1920
atggcggagc taattactac tctcccgcat caagattttg ggagttaatg gctggagcga     1980
ttatatccac attgagattt ataggaataa acacttcgtt atcaaaatta atgtccctgt     2040
taggaattat actaatcgca ttatcaataa ccatgataga tgaaaagatg tcatttcctg     2100
gatatatagc aataatccca atacttggcg cctctcttat aatagcatct aatggtaatg     2160
atttagttgt gtcgaaattg cttagtgtta ggcctgttgt tttctttggt cttattagct     2220 atcctctta tttgtggcat tggcctattt attcattcta tcgttcaata tttgctggct     2280
caccagacta ccatgaatta actcttcttt tattattatc gttcttttg gcgatattaa      2340 cttattattt aattgaaaaa ccactgagaa attccagaag taaatatatc acagcaatat     2400
tattagcatt atctgtattt gggacgggtt taattggcgc atttattttt catataaatg     2460
gagttaaaga cagggaaatc aataaatcag caagtgaata tgcttctgtt actgacgtgt     2520
acaattatta taaatatgga gaactactcc gtggagggat atgtcactca gtacaactta     2580
ctgctgccat atccaatgga tgtataaaaa atggcaagca taatatattt atcattggtg     2640
attcttatgc ggcggctctt ttcaatgggc tttctcatta tatagataat aaaggttctg     2700
attatataat aagccaaatg acagatggta atgctcctcc tctatttgtt gacggtaaag     2760
atgatttaca gagaagtgtc atcactctaa acaataatag aattaatgaa attaaacgtg     2820
ttcagcctga ggtggttctg ctgacatggt cagttcgagg aacaaatgga gtacatgata     2880
aaaagttagc aattgatgcg ttatcattaa ccattaaaaa aattaaagag gcatcccctg     2940
actcaaggat tgtttcatt ggaccagtcc cggaatggaa tgcaaattta gttaaaataa      3000
tatctaacta cctgagtgag tttaaaaaaa ctccaccatt gtatatgaca tatggattaa     3060
atagtgaaat aagcgagtgg gactcttact ttagtaacaa tgttccaaaa atgggaattg     3120
aatatatatc agcatacaaa gcattatgta acgaaagtgg atgtcttaca agagttggta     3180
atggtcctga ttttatcact gccgttgatt ggggacattt aacaaagcct ggttctgatt     3240
```

```
tccttttttaa taaaattgga aataaaataa tcaaatagat aggctgttac tattacatat    3300
aaatccaata tggaacatgc cagtcatact gtgtaactgc cactatatta acggtgatcg    3360
ctcaggcggt caccgaactc gataataaag cgaa                                3394
```

<210> SEQ ID NO 23
<211> LENGTH: 2940
<212> TYPE: DNA
<213> ORGANISM: Salmonella typhimurium

<400> SEQUENCE: 23

```
tgttgtaatt tttattttaa ttcattcgtt tttttatgcg gcttgccgga aaatatctgt      60
ataaggtaga tacgccaata ccaaaaataa tagctagttg ctgccgagga tggcctttct     120
ctaatagccg actaatctgt tcctgttcat gtttgttgat cgcccgaggg cgccctccca     180
gtcgtccttg cgctctggcg gcagccagtc cggcaagggt tcgctcgaca attaattctc     240
gctccatctc ggccagtgct gacattacat gaaaaaagaa tcgccccatc gcgctactgg     300
tatcaatact atcggttaaa gaatggaagt gagctccacg ttcatgtaat tctgatatta     360
acgccaccag ttttttcacg ctgcggccca gtctgtctaa tttccagacg acaagagtat     420
cgcctttatt tacatacttt aacgctcgtt tcaggccggg gcggtttgca atcttgccac     480
tgatacggtc ctcaaaaatg cggtcacaat ttgcactagt aagcgcatta cgctgtaaat     540
cgatattttg gtcaattgtt gacacccgaa atacccaat agtagccatg attttctcct      600
ttacatcaga taaggaagaa ttttagtcgc ttttctcatg gaggattgct ttatcaaaaa     660
ccttccaaaa ggaaaatttt atggcacaag taatcaacac taacagtctg tcgctgctga     720
cccagaataa cctgaacaaa tcccagtccg cactgggcac cgctatcgag cgtctgtctt     780
ctggtctgcg tatcaacagc gcgaaagacg atgcggcagg tcaggcgatt gctaaccgtt     840
tcaccgcgaa catcaaggt ctgactcagg cttcccgtaa cgctaacgac ggtatctcca      900
ttgcgcagac cactgaaggc gcgctgaacg aaatcaacaa caacctgcag cgtgtgcgtg     960
aactggcggt tcagtctgct aacagcacca actcccagtc tgacctcgac tccatccagg    1020
ctgaaatcac ccagcgcctg aacgaaatcg accgtgtatc cggccagact cagttcaacg    1080
gcgtgaaagt cctggcgcag acaacaccc tgaccatcca ggttggcgcc aacgacggtg      1140
aaactatcga tatcgatctg aagcagatca actctcagac cctgggtctg gactcactga    1200
acgtgcagaa agcgtatgat gtgaaagata cagcagtaac aacgaaagct tatgccaata    1260
atggtactac actggatgta tcgggtcttg atgatgcagc tattaaagcg ctacgggtg      1320 gtacgaatgg tacggcttct gtaaccggtg gtgcggttaa atttgacgca gataataaca    1380
agtactttgt tactattggt ggctttactg gtgctgatgc cgccaaaaat ggcgattatg    1440
aagttaacgt tgctactgac ggtacagtaa cccttgcggc tggcgcaact aaaaccacaa    1500
tgcctgctgg tgcgacaact aaaacagaag tacaggagtt aaaagataca ccggcagttg    1560
tttcagcaga tgctaaaaat gccttaattg ctggcggcgt tgacgctacc gatgctaatg    1620
gcgctgagtt ggtcaaaatg tcttataccg ataaaaatgg taagacaatt gaaggcggtt    1680
atgcgcttaa agctggcgat aagtattacg ccgcagatta cgatgaagcg acaggagcaa    1740
ttaaagctaa aactacaagt tatactgctg ctgacggcac taccaaaaca gcggctaacc    1800
aactgggtgg cgtagacggt aaaaccgaag tcgttactat cgacggtaaa acctacaatg    1860
ccagcaaagc cgctggtcat gatttcaaag cacaaccaga gctggcggaa gcagccgcta    1920
```

| | |
|---|---|
| aaaccaccga aaacccgctg cagaaaattg atgccgcgct ggcgcaggtg gatgcgctgc | 1980 |
| gctctgatct gggtgcggta caaaaccgtt tcaactctgc tatcaccaac ctgggcaata | 2040 |
| ccgtaaacaa tctgtctgaa gcgcgtagcc gtatcgaaga ttccgactac gcgaccgaag | 2100 |
| tttccaacat gtctcgcgcg cagattctgc agcaggccgg tacttccgtt ctggcgcagg | 2160 |
| ctaaccaggt cccgcagaac gtgctgtctc tgttacgtta atttatttcg ttttattcag | 2220 |
| ccccgtgaat tcggggcttt ttcatttagc atagatgaat atatatttat ggaatgtatg | 2280 |
| gctgtaaatg atatttccta cgggcgagaa gctgaaatat ggccgcggga ttattctatg | 2340 |
| cttgctcgtc gagttcaatt tctacgtttt aatgatatcc ctgttcgatt ggtgagtaat | 2400 |
| aatgcccgga taatcacagg ctacattgcg aagtttaatc cgaaggaaaa tttgattctg | 2460 |
| gcttcggata aacctaaagg aaataagcgc attgaagtta actagagtc tctggcaatt | 2520 |
| cttgaagaat tatcaggtaa tgacgctttt aatctttcgc tggtgccggc tgacggattt | 2580 |
| aatcttcagc aatatactcc atcaagaaga gattatttct cgatttgcaa taagtgctat | 2640 |
| aaacagggag tcggtatcaa aatctatatg aagtatggaa aggttttgac tggcaaaacg | 2700 |
| acaggcgtaa atgcgtgtca ggttggtgtg aggacatcca atggcaatca tatgcaagtt | 2760 |
| atgtttgact gggtgagcag gatcacgtct tcggactacg ctgaataacg cctacggtaa | 2820 |
| taaaaaattc cgtgagaaaa gtaaaactta ggggctacc ggaggggacc taatgaacgg | 2880 |
| aggtcatgga aggtattcat cgtgccagac tcttgctctt gtcagaagaa ggtaaaagta | 2940 |

<210> SEQ ID NO 24
<211> LENGTH: 493
<212> TYPE: DNA
<213> ORGANISM: Bacteriophage lambda

<400> SEQUENCE: 24

| | |
|---|---|
| acgttaaatc tatcaccgca agggataaat atctaacacc gtgcgtgttg actattttac | 60 |
| ctctggcggt gataatggtt gcatgtacta aggaggttgt atggaacaac gcataaccct | 120 |
| gaaagattat gcaatgcgct ttgggcaaac caagacagct aaagatctct cacctaccaa | 180 |
| acaatgcccc cctgcaaaaa ataaattcat ataaaaaaca tacagataac catctgcggt | 240 |
| gataaattat ctctggcggt gttgacataa ataccactgg cggtgatact gagcacatca | 300 |
| gcaggacgca ctgaccacca tgaaggtgac gctcttaaaa attaagccct gaagaagggc | 360 |
| agcattcaaa gcagaaggct ttggggtgtg tgatacgaaa cgaagcattg ggatctatcg | 420 |
| atgcatgcca tggtacccgg gagctcgaat taattctaga ataaattttg tttaactta | 480 |
| agaaggagat ata | 493 |

<210> SEQ ID NO 25
<211> LENGTH: 714
<212> TYPE: DNA
<213> ORGANISM: Bacteriophage lambda

<400> SEQUENCE: 25

| | |
|---|---|
| atgagcacaa aaaagaaacc attaacacaa gagcagcttg aggacgcacg tcgccttaaa | 60 |
| gcaatttatg aaaaaagaa aaatgaactt ggcttatccc aggaatctgt cgcagacaag | 120 |
| atggggatgg ggcagtcagg cgttggtgct ttatttaatg gcatcaatgc attaaatgct | 180 |
| tataacgccg cattgcttgc aaaaattctc aaagttagcg ttgaagaatt tagcccttca | 240 |
| atcgccagag aaatctacga gatgtatgaa gcggttagta tgcagccgtc acttagaagt | 300 |
| gagtatgagt accctgtttt ttctcatgtt caggcaggga tgttctcacc taagcttaga | 360 |

| | | | |
|---|---|---|---|
| accttttacca | aaggtgatgc | ggagagatgg gtaagcacaa | ccaaaaaagc cagtgattct | 420 |
| gcattctggc | ttgaggttga | aggtaattcc atgaccgcac | caacaggctc caagccaagc | 480 |
| tttcctgacg | gaatgttaat | tctcgttgac cctgagcagg | ctgttgagcc aggtgatttc | 540 |
| tgcatagcca | gacttggggg | tgatgagttt accttcaaga | aactgatcag ggatagcggt | 600 |
| caggtgtttt | tacaaccact | aaacccacag tacccaatga | tcccatgcaa tgagagttgt | 660 |
| tccgttgtgg | ggaaagttat | cgctagtcag tggcctgaag | agacgtttgg ctaa | 714 |

<210> SEQ ID NO 26
<211> LENGTH: 3659
<212> TYPE: DNA
<213> ORGANISM: Artificial Sequence
<220> FEATURE:
<223> OTHER INFORMATION: pUCpW_difCAT rfbE deletion cassette

<400> SEQUENCE: 26

| | | | |
|---|---|---|---|
| tcgacatact | gtgattggct | tagcaaggaa gaggaacaat | gaagctacca taaataatat | 60 |
| tatttacacg | acagaaaata | attggatcga aaaaatacta | gaatttgaac cgaatattat | 120 |
| tattaacact | attgcttgct | atggaagaca taacgaacct | gcaacagctt taatagaaag | 180 |
| caatattctt | atgcctatca | gagtattaga atctatctca | tcacttgatg cagtattcat | 240 |
| aaattgtgga | acatcactgc | caccaaatac gagtttatat | gcatactacta aacaaaaagc | 300 |
| aaatgaactc | gccgccgcca | ttatagataa agtttgcggt | aaatatatag agttaaaatt | 360 |
| ggagcatttc | tatggagctt | ttgatggaga cgataagttt | accagtatgg ttattagacg | 420 |
| ttgtttaagt | aaccagccag | taaagttaac atctggtttg | caacagagag atttcttgta | 480 |
| tataaaagat | ctactaacag | cgttcgattg tattataagt | aatgttaata atttccccaa | 540 |
| atttcatagt | attgaagttg | gtagtggaga ggcgatatca | attcgtgaat atgtagatac | 600 |
| tgttaaaaat | atcacaaaaa | gcaattctat aattgaattt | ggcgtggtca agaaagagt | 660 |
| aaatgaattg | atgtatagtt | gtgctgatat agcagaactt | gaaaaaatag gatggaaaag | 720 |
| agagttctct | cttgttgatg | cattaactga aataattgaa | gaggaaggga atgaatttg | 780 |
| tatggtatt | ttggtgctgg | aagttatggt agagaaacaa | tacccattct aaatcaacaa | 840 |
| ataaagcaag | aatgtggttc | tgactatgct ctggttttg | tggatgatgt tttggcagga | 900 |
| aagaaagtta | atggttttga | agtgctttca accaactgct | ttctaaaagc cccttattta | 960 |
| aaaaagtatt | ttaatgttgc | tattgctaat gataagatac | gacagagagt gtctgagtca | 1020 |
| atattattac | acggggttga | accaataact ataaacatc | caaatagcgt tgtttatgat | 1080 |
| catactatga | taggtagtgg | cgctattatt tctcccttg | ttacaatatc tactaatact | 1140 |
| catataggga | ggttttttca | tgcaaacata tactcatacg | ttgcacatga ttgtcaaata | 1200 |
| ggagactatg | ttacatttgc | tcctggggct aaatgtaatg | gatatgttgt tattgaagac | 1260 |
| aatgcatata | taggctcggg | tgcagtaatt aagcagggtg | ttcctaatcg cccacttatt | 1320 |
| attggcgcgg | gagccattat | aggtatgggg gctgttgtca | ctaaaagtgt tcctgccggt | 1380 |
| ataactgtgt | gcggaaatcc | agcaagagaa atgaaaagat | cgccaacatc tatttaatgc | 1440 |
| ggccgcattt | aacataatat | acattatgcg caccgcccga | acaccactcg ccacaaaaaa | 1500 |
| ccgccggaac | gtccaaaagt | acgggttttg ctgcccgcaa | acgggctgtt ctggtgttgc | 1560 |
| tagtttgtta | tcagaatcgc | agatccggct tcagccggtt | tgccggctga aagcgctatt | 1620 |
| tcttccagaa | ttgccatgat | tttttcccca cgggaggcgt | cactggctcc cgtgttgtcg | 1680 |

```
gcagctttga ttcgataagc agcatcgcct gtttcaggct gtctatgggc cggccaaatc    1740
agtaagttgg cagcatcacc cgacgcactt tgcgccgaat aaatacctgt gacggaagat    1800
cacttcgcag aataaataaa tcctggtgtc cctgttgata ccgggaagcc ctgggccaac    1860
ttttggcgaa aatgagacgt tgatcggcac gtaagaggtt ccaactttca ccataatgaa    1920
ataagatcac taccgggcgt atttttttgag ttatcgagat tttcaggagc taaggaagct    1980
aaaatggaga aaaaaatcac tggatatacc accgttgata tatcccaatg gcatcgtaaa    2040
gaacattttg aggcatttca gtcagttgct caatgtacct ataaccagac cgttcagctg    2100
gatattacgg ccttttttaaa gaccgtaaag aaaaataagc acaagtttta tccggccttt    2160
attcacattc ttgcccgcct gatgaatgct catccggaat tccgtatggc aatgaaagac    2220
ggtgagctgg tgatatggga tagtgttcac ccttgttaca ccgttttcca tgagcaaact    2280
gaaacgtttt catcgctctg gagtgaatac cacgacgatt tccggcagtt tctacacata    2340
tattcgcaag atgtggcgtg ttacggtgaa aacctggcct atttccctaa agggtttatt    2400
gagaatatgt ttttcgtctc agccaatccc tgggtgagtt tcaccagttt tgatttaaac    2460
gtggccaata tggacaactt cttcgccccc gttttcacca tgggcaaata ttatacgcaa    2520
ggcgacaagg tgctgatgcc gctggcgatt caggttcatc atgccgtttg tgatggcttc    2580
catgtcggca gaatgcttaa tgaattacaa cagtactgcg atgagtggca gggcggggcg    2640 taatttttt aaggcagtta ttggtgccct taaacgcctg gttgctacgc ctgaataagt    2700
gataataagc ggatcctagg atggtgttaa gcggcggtt ttgagatgta aactcgccca    2760
tttaacataa tatacattat gcgcaccgcg gccgccagtg tgaggatcct gtttctgccc    2820
gcgaaagcgg gcataattaa agaatgaaat attttttata attaaaagat gaagctgacg    2880
tgaggaaact gaggttggtt agaattccaa gacatcttat tattgccgct tcctcttggc    2940
tttcaaagat aataattgcc ggtgttcagt tagtaagtgt taaatttctt ttagaaattc    3000
ttggcgaaga atcatacgct gtatttactc ttttaactgg attattggtc tggtttagca    3060
ttgcagatat tgggattggt agtagtctac aaaattatat atctgagttg aaagctgata    3120
gaaaatcata tgatgcatat atcaaggccg cagttcatat tctattcgca tccttaatca    3180
ttttaagctc tacattattc ttcttatcag ataaattatc gtcactatat cttacttcat    3240
ttagcgatga attgaaaaac aactcaggaa gttatttttt tatagcaagt atattattta    3300
tattcatcgg cgttgggagt gtggtctata aaatattatt tgcggaactg ttagggtgga    3360
aagctaatat aattaatgca ttatcttatc ttttaggttt tttagatgta gttgcgatcc    3420
attatttaat gccagattcg agtattacct tcgctttagt agcattgtat gctccggtag    3480
caatactgcc cattatatat atatcgtttc ggtatatata tgttcttaaa gcgaaagtaa    3540
actttaacac ctataaatta ttactatcac gttcatcagg gtttctgatt ttttcgtcct    3600
tatcgataat agttttacaa actgattata ttgtgatgtc tcagaaatta tctggagct    3659
```

<210> SEQ ID NO 27  
<211> LENGTH: 1305  
<212> TYPE: DNA  
<213> ORGANISM: Artificial Sequence  
<220> FEATURE:  
<223> OTHER INFORMATION: PL rfbE deletion cassette

<400> SEQUENCE: 27

```
aataggatgg aaaagagagt tctctcttgt tgatgcatta actgaaataa ttgaagagga     60
agggaaatga aaagcttggt accgagctcg gatccactag taacggccgc cagtgtgctg    120
```

```
gaattcgccc tttaagcggc cgcatttaac ataatataca ttatgcgcac catccgctta      180
ttatcactta ttcaggcgta gcaccaggcg tttaagggca ccaataactg ccttaaaaaa      240
attacgcccc gccctgccac tcatcgcagt actgttgtaa ttcattaagc attctgccga      300
catggaagcc atcacaaacg gcatgatgaa cctgaatcgc cagcggcatc agcaccttgt      360
cgccttgcgt ataatatttg cccatggtga aacgggggc gaagaagttg tccatattgg       420
ccacgtttaa atcaaaactg gtgaaactca cccaggcatt ggctgagacg aaaaacatat      480
tctcaataaa ccctttaggg aataggccaa ggttttcacc gtaacacgcc acatcttgcg      540
aatatatgtg tagaaactgc cggaaatcgt cgtggtattc actccagagc gatgaaaacg      600
tttcagtttg ctcatggaaa acggtgtaac aagggtgaac actatcccat atcaccagct      660
caccgtcttt cattgccata cggaattccg atgagcatt catcaggcgg gcaagaatgt       720
gaataaaggc cggataaaac ttgtgcttat ttttctttac ggtctttaaa aaggccgtaa      780
tatccagctg aacggtctgg ttataggtac attgagcaac tgactgaaat gcctcaaaat      840
gttctttacg atgccattgg gatatatcaa cggtggtata ccagtgatt ttttctcca       900 ttttagcttc cttagctcct gaaaatctcg ataactcaaa aaatacgccc ggtagtgatc      960
ttatttcatt atggtgaaag ttggaacctc ttacgtgccg atcaacgtct cattttcgcc      1020
aaaagttggc ccagggcttc ccggtatcaa caggacacc aggatttatt tattctgcga       1080
agtgatcttc cgtcacaggt atttattcga agacgaaagg gatgcaggag tcgcataagg      1140
gatttaacat aatatacatt atgcgcaccg cggccgcgga aagggcgaat tctgcagata      1200
tccatcacac tggcggccgc tcgagcatgc atctagagtg aggaaactga ggttggttag      1260
aattccaaga catcttatta ttgccgcttc ctcttggctt tcaaa                      1305
```

<210> SEQ ID NO 28
<211> LENGTH: 4915
<212> TYPE: DNA
<213> ORGANISM: Artificial Sequence
<220> FEATURE:
<223> OTHER INFORMATION: pUCpF_difCAT fliC replacement cassette

<400> SEQUENCE: 28

```
cattccctga ggggcgtcgg ttacggtatt gctctgacgc tcaatgtcga tgccgtttac       60
gttcagcttc gcgttttctg ctttcaccag ctcttgcata ttgccggtat tggtggtgct      120
gtcataagcg agtagatcgt taagttttgt atcgccttcc accgtgatct tcatcgtatt      180
gtcggtaccg ctattggcgg taagcaccaa ctggaattcg ttctctttga ccttaacgat      240
actggcggcg ataccgctgt cggcgtcatt aatggcgtca cggatcgcct ccatggaggt      300
gtcgccttta tccagcttaa tttccagcgg ctctttacgt cccggctgtt caattttaat      360
tgtccgggat gtgaccgacg tatcgcccaa ctgctctttg gtggttgcga aggtggtttt      420
tgtcgccagc gactgcgcgg cggcaagctg ggttacgcta atcttataag tccctgcggc      480
agcgcctgcg gtagtactga ctttgaggtc ctctgtcgtg ctggacgcca cggtagactt      540
aaataaatcc gctttatta acgcggtatt tgccgtctgg aatttttcta atgcgctttt       600
caatgtgcca taggcggtta gctttgccga attcgcgctc tgctgtttgg taattggcgt      660
taagcgtcct ttttcgttct tgtcaggtc tgtcaacaac tggtctaacg gtaagtttga       720
tcccacacct aatgatgaaa ttgaagccat gccttcttcc ttttttgattg caaacagtag     780 ttaagcgcgt tatcggcaat ctggaggcaa agtttaatga taatttttgca aaaataatgc    840
```

```
gcggaataat gatgcataaa gcggctattt cgccgcctaa gaaaaagatc gggggaagtg    900
aaaaattttc taaagttcga aattcaggtg ccgatacaag ggttacggtg agaaaccgtg    960
ggcaacagcc caataacatc aagttgtaat tgataaggaa aagatcatgg cacaagtcat   1020
taatacaaac agcctgtcgc tgttgaccca gaataacctg aacaaatccc agtccgctct   1080
gggcaccgct atcgagcgtc tgtcttccgg tctgcgtatc aacagcgcga aagacgatgc   1140
ggcaggtcag gcaattgcta accgtttcac cgcgaacatc aaaggtctga ctcaggcttc   1200
ccgtaacgct aacgacggta tctccattgc gcagaccact gaaggcgcgc tgaacgaaat   1260
caacaacaac ctgcagcgtg tgcgtgaact ggcggttcag tctgctaaca gcaccaactc   1320
ccagtctgac ctcgactcca tccaggctga aatcacccag cgcctgaacg aaatcgaccg   1380
tgtatccggt cagactcagt tcaacggcgt gaaagtcctg gcgcaggaca cacccctgac   1440
catccaggtt ggtgccaaca cggtgaaac cattgatatc gatctgaaac agatcaactc   1500
tcagaccctg ggtctggata cgctgaatgt gcagaaaaaa tatgatgtga gagcgaagc   1560
ggtcacgcct tcggctacat taagcactac tgcacttgat ggtgctggcc tcaaaaccgg   1620
aaccggttct acaactgata ctggttcaat taaggatggt aaggtttact ataacagcac   1680
ctctaaaaat tattatgttg aagtagaatt taccgatgcg accgatcaaa ccaacaaagg   1740
cggattctat aaagttaatg ttgctgatga tggtgcagtc acaatgactg cggctaccac   1800
caaagaggct acaactccta caggtattac tgaagttact caagtccaaa acctgtggc   1860
tgctccagct gctatccagg ctcagttgac tgctgcccat gtgaccggcg ctgatactgc   1920
tgaaatggtt aagatgtctt atacggataa aaacggtaag actattgatg gcggtttcgg   1980
tgttaaagtt ggggctgata tttatgctgc aacaaaaaat aaagatggat cgttcagcat   2040
taacaccact gaatataccg ataaagacgg caacactaaa actgcactaa accaactggg   2100
tggcgcagac ggtaaaactg aagttgttc tatcgacggt aaaacctaca atgccagcaa   2160
agccgctggt cacaactta aagcacagcc agagctggct gaagcggctg ctgcaaccac   2220
cgaaaacccg ctggctaaaa ttgatgccgc gctggcgcag gttgatgcgc tgcgttctga   2280
cttgggtgcg gttcagaacc gtttcaactc cgctatcacc aacctgggca ataccgtaaa   2340
taacctgtct tctgcccgta gccgtatcga agattccgac tacgcgaccg aagtttccaa   2400
catgtctcgc gcgcagatcc tgcagcaggc cggtacctcc gttctggcgc aggcgaacca   2460
ggttccgcaa aacgtcctct ctttactgcg ttaatgcggc cgcatttaac ataatataca   2520
ttatgcgcac cgcccgaaca ccactcgcca caaaaaaccg ccggaacgtc caaaagtacg   2580
ggttttgctg cccgcaaacg ggctgttctg tgttgctag tttgttatca gaatcgcaga   2640
tccggcttca gccggtttgc cggctgaaag cgctatttct tccagaattg ccatgatttt   2700
ttccccacgg gaggcgtcac tggctcccgt gttgtcggca gctttgattc gataagcagc   2760
atcgcctgtt tcaggctgtc tatgggccgg ccaaatcagt aagttggcag catcacccga   2820
cgcactttgc gccgaataaa tacctgtgac ggaagatcac ttcgcagaat aaataaatcc   2880
tggtgtccct gttgataccg ggaagccctg ggccaacttt tggcgaaaat gagacgttga   2940
tcggcacgta agaggttcca actttcacca taatgaaata agatcactac cgggcgtatt   3000
ttttgagtta tcgagatttt caggagctaa ggaagctaaa atggagaaaa aaatcactgg   3060
atataccacc gttgatatat cccaatggca tcgtaaagaa catttgagg catttcagtc   3120
agttgctcaa tgtacctata accagaccgt tcagctggat attacggcct ttttaaagac   3180
cgtaaagaaa aataagcaca gttttatcc ggcctttatt cacattcttg cccgcctgat   3240
```

```
gaatgctcat ccggaattcc gtatggcaat gaaagacggt gagctggtga tatgggatag    3300
tgttcaccct tgttacaccg ttttccatga gcaaactgaa acgttttcat cgctctggag    3360
tgaataccac gacgattrcc ggcagtttct acacatatat tcgcaagatg tggcgtgtta    3420
cggtgaaaac ctggcctatt tccctaaagg gtttattgag aatatgtttt tcgtctcagc    3480
caatccctgg gtgagtttca ccagttttga tttaaacgtg gccaatatgg acaacttctt    3540
cgcccccgtt ttcaccatgg gcaaatatta tacgcaaggc gacaaggtgc tgatgccgct    3600
ggcgattcag gttcatcatg ccgtttgtga tggcttccat gtcggcagaa tgcttaatga    3660
attacaacag tactgcgatg agtggcaggg cggggcgtaa ttttttttaag gcagttattg    3720 gtgcccttaa acgcctggtt gctacgcctg aataagtgat aataagcgga tcctaggatg    3780
gtgttaagcg ggcggttttg agatgtaaac tcgcccattt aacataatat acattatgcg    3840
caccgcggcc gccagtgtga ggatccccgg cgattgattc accgacacgt ggtacacaat    3900
caaggcagcg aaagctgcct tttttaattc cggagcctgt gtaatgaaag aaatcaccgt    3960
cactgaacct gcctttgtca cccgcttttc ctgttctggc tcggcctgtc gcgaccattg    4020
ttgtaagggc tggaaaatca cgctggataa gacgacggtt aaaaagtatc tcgccagtaa    4080
agacacgacg attcgtacca tcgcgcaaga ccatattatt ctgctgaaaa agaacaataa    4140
tcattggggg gaaattaaac tgccttcggc gctgggaagt tgcccttatc tggatgagga    4200
ccgtttgtgc cgggtacaaa aacgttaggc gcaaaggcat taagtcatac ctgttcctct    4260
ttcccacggg cgcaccatac ctataaaaat gaggtacgta actccctgag tcttgcctgt    4320
ccggaggtaa cgtcccgcat tttaaacgat cctgacgcaa tggcgctcgg cgaaaaaaca    4380
atcattcagc agacattcaa tactgcgccg ttattctcac cgcagcaaaa gttactcaat    4440
ctgttttgcc tgagtctgat caaccatgcc aacagcagta cggaaacggc gctctatggg    4500
ttgattaaat tcgtcatgta tgcacataaa tttgccaaaa ttgatgatgc cgcgctgggt    4560
gaactggaac aggtgtatgc cgcgttactt gagcagttgc agaccggcgt gctggcgcag    4620
gaattgatga atatcgcgcc ggacagcaag gtaaaaacct cgctggtatt gcagatgcag    4680
aactatttcc gctcgctccc gcttagtcgt ggcagtgtta cctcgatca ctatatccag    4740 tgtcttctgc gggtgctgac ggcggaagag ggcgtttcaa tggagcagaa ggttagcgat    4800
attgagtcct cattagcgcg ctgtttacag gcggatgagc agcagaagaa ctgggctttc    4860
agaaatttaa ttctctataa aatttgggaa ataatttcc ccaaccagcc gaatg          4915
```

<210> SEQ ID NO 29
<211> LENGTH: 2931
<212> TYPE: DNA
<213> ORGANISM: Artificial Sequence
<220> FEATURE:
<223> OTHER INFORMATION: tviA expression plasmid pBRT4tviA

<400> SEQUENCE: 29

```
aacatcgata ttgccatcgc ggatgtcgcc tgtcttatct accatcataa acatcatttg      60
cctatggctc acgacagtat aggcaatgcc gttttttata ttgctaattg tttcgccaat    120
caacgcaaaa gtatggcgat tgctaaagcc gtctccctgg gcgtagatt agccttaacc    180 gcgacggtaa tgactcattc atactggagt ggtagtttgg gactacagcc tcatttatta    240
gagcgtctta atgatattac ctatggacta atgagttta ctcgcttcgg tatggatggg    300
atggcaatga ccggtatgca ggtcagcagc ccattatatc gtttgctggc tcaggtaacg    360
```

```
ccagaacaac gtgcgccgga gtaatcgttt tcaggtatat accggatgtt cattgctttc    420
taaattttgc tatgttgcca gtatccttac gatgtatttta ttttaaggaa aagccatatg    480
aggtttcatc atttctggcc tccgaatgat atctatttcg gggttggagc tgctggcatt    540
attgaagaag tgtcactgat aacaaatgac agaaattatt tgtttgtgaa cctaaatcgc    600
tacagcctgt taaatgccct gaattttttc acgcgaatga gtgatattaa taaaataatc    660
gttatcattt caagttcgcg actaatgccc cttgcacgtt tttggttgac agagtgcaaa    720
aatgttattg ctgttttcga tgcggcaaca tcagtccagg atattatcag aaatgtcagt    780
caacaccaaa gtggtgaaaa gatcttgacg gagcagagag attatcgttt cagaattaac    840
cgtaaggata tagtaaagat gaaatatttc ctttcggaaa gtggtatgga agagcttcag    900
gatagattta tgaactcatc atcgactatg tatcgctgga gaaaagaatt ggcagtaaaa    960
tttggagtac gtgagccgcg ctatctgtta ttgccggatt cagttacttt actgtaatgt   1020
cgacataaaa cgaaaggctc agtcgaaaga ctgggccttt cgttttatct gttgtttgtc   1080
ggtgaacgct ctcctgagta ggacaaatcc gccgggagcg gatttgaacg ttgcgaagca   1140
acggcccgga gggtggcggg caggacgccc gccataaact gccaggcatc aaattaagca   1200
gaaggccatc ctgacggatg ccttttctg cagataaaag gatctaggtg aagatccttt    1260
ttgataatct catgaccaaa atcccttaac gtgagttttc gttccactga gcgtcagacc   1320
ccgtagaaaa gatcaaagga tcttcttgag atcctttttt tctgcgcgta atctgctgct   1380
tgcaaacaaa aaaaccaccg ctaccagcgg tggtttgttt gccggatcaa gagctaccaa   1440
ctctttttcc gaaggtaact ggcttcagca gagcgcagat accaaatact gtccttctag   1500
tgtagccgta gttaggccac cacttcaaga actctgtagc accgcctaca tacctcgctc   1560
tgctaatcct gttaccagtg gctgctgcca gtggcgataa gtcgtgtctt accgggttgg   1620
actcaagacg atagttaccg gataaggcgc agcggtcggg ctgaacgggg ggttcgtgca   1680
cacagcccag cttggagcga acgacctaca ccgaactgag atacctacag cgtgagctat   1740
gagaaagcgc cacgcttccc gaagggagaa aggcggacag gtatccggta agcggcaggg   1800
tcggaacagg agagcgcacg agggagcttc caggggggaaa cgcctggtat ctttatagtc   1860
ctgtcgggtt tcgccacctc tgacttgagc gtcgattttt gtgatgctcg tcagggggc    1920
ggagcctatg gaaaaacgcc agcaacgcgg cctttttacg gttcctggcc ttttgctggc   1980
cttttgctca catgttcttt cctgcgttat ccctgattc tgtggataac cgtattaccg    2040
cctttgagtg agctgatacc gctttttcgt gacattcagt tcgctgcgct cacggctctg   2100
gcagtgaatg ggggtaaatg cactacagg cgcctttat ggattcatgc aaggaaacta    2160
cccataatac aagaaaagcc cgtcacgggc ttctcagggc gttttatggc gggtctgcta   2220
tgtggtgcta tctgactttt tgctgttcag cagttcctgc cctctgattt tccagtctga   2280
ccacttcgga ttatcccgtg acaggtcatt cagactggct aatgcaccca gtaaggcagc   2340
ggtatcatca acaggcttac ccgtcttact gtcaaccaga cccgccagga taagcaatcc   2400
ggcagactgg tacagagcat ggtcacgggc tttacgggcg ctctggctt cggctcgctt    2460
ttctgcctgt atcaggttca tgagcggccg cggcgcgcca gcttatcatt gataagcttc   2520
ttgaactctt tatcactgat aaagacgcgt catagacagc ctgaaacagg cgatgctgct   2580
tatcgaatca aagctgccga caacacggga gccagtgacg cctcccgtgg ggaaaaaatc   2640
atggcaattc tggaagaaat agcgctttca gccggcaaac cggctgaagc cggatctgcg   2700
attctgataa caaactagca acaccagaac agcccgtttg cggcagcaa aacccgtact    2760
```

```
tttggacgtt ccggcggttt tttgtggcga gtggtgttcg ggcggtgcgc gcaagatcca    2820
ttatgttaaa cgggcgagtt tacatctcaa aaccgcccgc ttaacaccat tcatgagcgg    2880
ccgccagtgt gctggaattc ggcttcatga ttttttattc aacgaagagt t             2931
```

<210> SEQ ID NO 30
<211> LENGTH: 5188
<212> TYPE: DNA
<213> ORGANISM: Artificial Sequence
<220> FEATURE:
<223> OTHER INFORMATION: fepE expression plasmid pBAD2fepE

<400> SEQUENCE: 30

```
gtgcctgtca aatggacgaa gcagggattc tgcaaaccct atgctactcc gtcaagccgt      60
caattgtctg attcgttacc aattatgaca acttgacggc tacatcattc acttttttctt   120 cacaaccggc acggaactcg ctcgggctgg ccccggtgca ttttttaaat acccgcgaga    180
aatagagttg atcgtcaaaa ccaacattgc gaccgacggt ggcgataggc atccgggtgg    240
tgctcaaaag cagcttcgcc tggctgatac gttggtcctc gcgccagctt aagacgctaa    300
tccctaactg ctggcggaaa agatgtgaca acgcgacgg cgacaagcaa acatgctgtg    360
cgacgctggc gatatcaaaa ttgctgtctg ccaggtgatc gctgatgtac tgacaagcct    420
cgcgtacccg attatccatc ggtggatgga gcgactcgtt aatcgcttcc atgcgccgca    480
gtaacaattg ctcaagcaga tttatcgcca gcagctccga atagcgccct tccccttgcc    540
cggcgttaat gatttgccca aacaggtcgc tgaaatgcgg ctggtgcgct tcatccgggc    600
gaaagaaccc cgtattggca aatattgacg gccagttaag ccattcatgc cagtaggcgc    660
gcggacgaaa gtaaacccac tggtgatacc attcgcgagc ctccggatga cgaccgtagt    720
gatgaatctc tcctggcggg aacagcaaaa tatcacccgg tcggcaaaca aattctcgtc    780
cctgattttt caccaccccc tgaccgcgaa tggtgagatt gagaatataa cctttcattc    840
ccagcggtcg gtcgataaaa aaatcgagat aaccgttggc ctcaatcggc gttaaacccg    900
ccaccagatg gcattaaaac gagtatcccg gcagcagggg atcattttgc gcttcagcca    960
tacttttcat actcccgcca ttcagagaag aaaccaattg tccatattgc atcagacatt   1020
gccgtcactg cgtctttac tggctcttct cgctaaccaa accggtaacc ccgcttatta   1080
aaagcattct gtaacaaagc gggaccaaag ccatgacaaa aacgcgtaac aaaagtgtct   1140
ataatcacgg cagaaaagtc cacattgatt atttgcacgg cgtcacactt gctatgcca    1200 tagcattttt atccataaga ttagcggatc ctacctgacg cttttttatcg caactctcta   1260 ctgtttctcc atacccgttt ttttgggcta gcgaattgag gaggagatat acatatgcca   1320
tctcttaatg taaaacaaga aaaaaatcag tcatttgcag ttattcact gccgcccgcc    1380 aacagtcatg aaatcgattt gtttagcctt atagaggtgt tatggcaggc gaaacgtcgt   1440
attcttgcta ccgttttcgc ctttgcgtgc gtggggttgc ttctgtcctt tctgctgccg    1500
caaaaatgga ccagccaggc gattgtcaca ccggcggagt cggtacagtg cagggctg     1560 gagagaacgt tgaccgcgct gcgcgtgttg gatatggagg taagcgttga tcggggcagc   1620
gtatttaatc tgtttattaa aaagtttagc tcgccctcgc tgctggaaga atatcttcgt   1680
tcttctccgt atgtcatgga tcaattaaaa ggcgcgcaaa tagacgagca ggatcttcac   1740
cgggcgattg tcctgctgag cgaaaaaatg aaagcggtgg acagtaatgt cggcaagaaa    1800
aatgaaacgt cgttattcac gtcgtggaca ttgagtttta ccgcgccgac gcgggaagaa   1860
```

```
gcgcaaaaag tgctggctgg ctatattcag tacatctccg atatcgtcgt gaaagagacg   1920
ctggaaaata ttcgtaacca gctggaaatc aaaacccgct atgagcagga aaagctggcg   1980
atggatcggg tgcgtctcaa aaatcagctt gatgccaata ttcaacgtct tcattattcg   2040
ctggaaatcg ccaacgccgc cggtattaag agaccggttt acagcaatgg tcaggcggta   2100
aaagatgatc cggattttc tatttctctc ggcgcggatg gtatttcccg caaactggaa   2160
attgaaaaag gggtaacgga cgtggccgag atcgacggtg atttgcgtaa ccgtcaatac   2220
catgttgaac aactggcggc aatgaatgtg agtgacgtga agtttacccc gtttaaatat   2280
caactgtcgc cgtctctgcc agtgaaaaaa gatggcccgg gtaaagccat cattattatc   2340
ctggcggcgt tgattggcgg tatgatggcc tgcggcggcg tattactgcg tcacgcgatg   2400
gtctcgcgta aaatgaaaa cgcgctggcg atagatgaac ggttagtctg agtcgacctg   2460
caggcatgca agcttggctg ttttggcgga tgagagaaga ttttcagcct gatacagatt   2520
aaatcagaac gcagaagcgg tctgataaaa cagaatttgc ctggcggcag tagcgcggtg   2580
gtcccacctg accccatgcc gaactcagaa gtgaaacgcc gtagcgccga tggtagtgtg   2640
gggtctcccc atgcgagagt agggaactgc caggcatcaa ataaaacgaa aggctcagtc   2700
gaaagactgg gcctttcgtt ttatctgttg tttgtcggtg aacgctctcc tgagtaggac   2760
aaatccgccg ggagcggatt tgaacgttgc gaagcaacgg cccggagggt ggcgggcagg   2820
acgcccgcca taaactgcca ggcatcaaat taagcagaag gccatcctga cggatggcct   2880
ttttgcgttt ctacaaactc ttttgttta ttttctaaa tacattcaaa tatgtatccg   2940
ctcatgtggc cggcccggcc taggaaagcc acgttgtgtc tcaaaatctc tgatgttaca   3000
ttgcacaaga taaaaatata tcatcatgaa cataaaaact gtctgcttac ataaacagta   3060
atacaagggg tgttatgagc catattcaac gggaaacgtc ttgctcgagg ccgcgattaa   3120
attccaacat ggatgctgat ttatatgggt ataaatgggc tcgcgataat gtcgggcaat   3180
caggtgcgac aatctatcga ttgtatggga agcccgatgc gccagagttg tttctgaaac   3240
atggcaaagg tagcgttgcc aatgatgtta cagatgagat ggtcagacta aactggctga   3300
cggaatttat gcctcttccg accatcaagc attttatccg tactcctgat gatgcatggt   3360
tactcaccac tgcgatcccc gggaaaacag cattccaggt attagaagaa tatcctgatt   3420
caggtgaaaa tattgttgat gcgctggcag tgttcctgcg ccggttgcat tcgattcctg   3480
tttgtaattg tccttttaac agcgatcgcg tatttcgtct cgctcaggcg caatcacgaa   3540
tgaataacgg tttggttgat gcgagtgatt ttgatgacga gcgtaatggc tggcctgttg   3600
aacaagtctg gaaagaaatg cataagcttt tgccattctc accggattca gtcgtcactc   3660
atggtgattt ctcacttgat aaccttattt ttgacgaggg gaaattaata ggttgtattg   3720
atgttggacg agtcggaatc gcagaccgat accaggatct tgccatccta tggaactgcc   3780
tcggtgagtt ttctccttca ttacagaaac ggcttttca aaaatatggt attgataatc   3840
ctgatatgaa taaattgcag tttcatttga tgctcgatga gttttctaa tcagaattgg   3900 ttaattggtt gtaacactgg cagagcatta cgctgacttg acgggacggc ggctttgttg   3960
aataaatcga acttttccta ggccgggccg gccacatgac caaatcccct aacgtgagt   4020 tttcgttcca ctgagcgtca gaccccgtag aaaagatcaa aggatcttct tgagatcctt   4080
ttttcctgcg cgtaatctgc tgcttgcaaa caaaaaaacc accgctacca gcggtggttt   4140
gtttgccgga tcaagagcta ccaactcttt ttccgaaggt aactggcttc agcagagcgc   4200
agataccaaa tactgtcctt ctagtgtagc cgtagttagg ccaccacttc aagaactctg   4260
```

-continued

```
tagcaccgcc tacatacctc gctctgctaa tcctgttacc agtggctgct gccagtggcg   4320
ataagtcgtg tcttaccggg ttggactcaa gacgatagtt accggataag gcgcagcggt   4380
cgggctgaac ggggggttcg tgcacacagc ccagcttgga gcgaacgacc tacaccgaac   4440
tgagatacct acagcgtgag ctatgagaaa gcgccacgct tcccgaaggg agaaaggcgg   4500
acaggtatcc ggtaagcggc agggtcggaa caggagagcg cacgagggag cttccagggg   4560
gaaacgcctg gtatctttat agtcctgtcg ggtttcgcca cctctgactt gagcgtcgat   4620
ttttgtgatg ctcgtcaggg gggcggagcc tatggaaaaa cgccagcaac gcggcctttt   4680
tacggttcct ggccttttgc tggccttttg ctcacttta cggttcctgg cctttgctg    4740 gccttttgct cacatgtatg gtgttaagcg ggcggtttg agatgtaaac tcgcccgttt    4800
aacataatgg atcttgcgcg caccgcccga acaccactcg ccacaaaaaa ccgccggaac   4860
gtccaaaagt acgggttttg ctgcccgcaa acgggctgtt ctggtgttgc tagtttgtta   4920
tcagaatcgc agatccggct tcagccggtt tgccggctga aagcgctatt tcttccagaa   4980
ttgccatgat tttttcccca cgggaggcgt cactggctcc cgtgttgtcg gcagctttga   5040
ttcgataagc agcatcgcct gtttcaggct gtctatgaca tgttctttcc tgcgttatcc   5100
ccaattgtga gcgctcacaa tttgctgcgg taagtcgcat aaaaaccatt cttcataatt   5160
caatccattt actatgttat gttctgag                                      5188
```